United States Patent
Bartels et al.

(10) Patent No.: US 12,344,614 B2
(45) Date of Patent: Jul. 1, 2025

(54) BENZODIAZEPINE DERIVATIVES AS GABA A GAMMA1 PAM

(71) Applicant: Hoffmann-La Roche Inc., Little Falls, NJ (US)

(72) Inventors: Bjoern Bartels, Schopfheim (DE); Giuseppe Cecere, Basel (CH); Luca Gobbi, Buus (CH); Maria-Clemencia Hernandez, Delémont (CH); Roland Humm, Auggen (DE); Andrés Miguel Olivares Morales, Binningen (CH); Angélique Patiny-Adam, Kembs (FR); Valerie Runtz-Schmitt, Rixheim (FR); Christian Schnider, Biel-Benken (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 137 days.

(21) Appl. No.: 17/938,000

(22) Filed: Oct. 4, 2022

(65) Prior Publication Data

US 2023/0142171 A1    May 11, 2023

(30) Foreign Application Priority Data

Oct. 6, 2021    (EP) ..................... 21201128

(51) Int. Cl.
| | |
|---|---|
| *C07D 487/04* | (2006.01) |
| *A61K 9/00* | (2006.01) |
| *A61K 9/08* | (2006.01) |
| *A61K 9/20* | (2006.01) |
| *A61K 9/48* | (2006.01) |
| *A61K 47/10* | (2017.01) |

(Continued)

(52) U.S. Cl.
CPC .......... *C07D 487/04* (2013.01); *A61K 9/0019* (2013.01); *A61K 9/08* (2013.01); *A61K 9/2013* (2013.01); *A61K 9/2018* (2013.01); *A61K 9/2054* (2013.01); *A61K 9/485* (2013.01); *A61K 9/4858* (2013.01); *A61K 9/4866* (2013.01); *A61K 47/10* (2013.01); *A61K 47/12* (2013.01); *C07D 243/24* (2013.01)

(58) Field of Classification Search
CPC .. C07D 487/04; C07D 243/24; A61K 9/0019; A61K 9/08; A61K 9/2013; A61K 9/2018; A61K 9/2054; A61K 9/485; A61K 9/4858; A61K 9/4866; A61K 47/10; A61K 47/12

See application file for complete search history.

(56) References Cited

U.S. PATENT DOCUMENTS

| | | | |
|---|---|---|---|
| 3,681,343 A | 8/1972 | Hester, Jr. | |
| 3,734,922 A | 5/1973 | Hester, Jr. | |

(Continued)

FOREIGN PATENT DOCUMENTS

| | | |
|---|---|---|
| DE | 2533924 | 2/1977 |
| DE | 3724031 | 1/1988 |

(Continued)

OTHER PUBLICATIONS

Khanna, Arjun et al. "Limitations of Current GABA Agonists in Neonatal Seizures: Toward GABA Modulation Via the Targeting of Neuronal Cl(-) Transport." Frontiers in neurology vol. 4 78. Jun. 25, 2013, doi:10.3389/fneur.2013.00078 (Year: 2013).*

(Continued)

*Primary Examiner* — Danah Al-Awadi
*Assistant Examiner* — Donna M Nestor
(74) *Attorney, Agent, or Firm* — Robert C. Hall

(57) ABSTRACT

The invention provides novel heterocyclic compounds having the general formula (I) or (II), and pharmaceutically acceptable salts thereof, wherein the variables are as described herein.

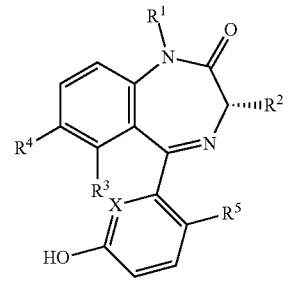

(I)

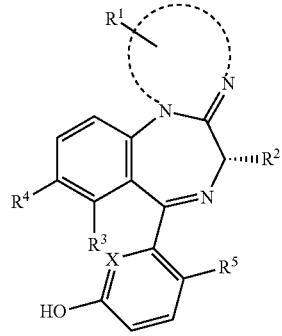

(II)

Further provided are pharmaceutical compositions including the compounds, processes of manufacturing the compounds and methods of using the compounds as medicaments, in particular methods of using the compounds for the treatment or prevention of acute neurological disorders, chronic neurological disorders and/or cognitive disorders.

8 Claims, No Drawings

(51) Int. Cl.
 *A61K 47/12* (2006.01)
 *C07D 243/24* (2006.01)

(56) References Cited

U.S. PATENT DOCUMENTS

| | | | |
|---|---|---|---|
| 3,987,052 | A | 10/1976 | Hester, Jr. |
| 4,201,712 | A | 5/1980 | Weber et al. |
| 4,621,083 | A | 11/1986 | Casals-Stenzel et al. |
| 5,185,442 | A | 2/1993 | Weber et al. |
| 5,532,233 | A | 7/1996 | Weber et al. |
| 10,259,815 | B2 * | 4/2019 | Cook ............... C07D 487/04 |
| 11,739,095 | B2 | 8/2023 | Cecere et al. |
| 2012/0295892 | A1 | 11/2012 | Cook et al. |

FOREIGN PATENT DOCUMENTS

| | | |
|---|---|---|
| EP | 0176927 A2 | 4/1986 |
| WO | 03/082832 A2 | 10/2003 |
| WO | 2015/200766 A2 | 12/2015 |
| WO | 2018/035246 A1 | 2/2018 |
| WO | 2020/198275 A1 | 10/2022 |

OTHER PUBLICATIONS

Sudhakar, Shyam Kumar. "Are GABAergic drugs beneficial in providing neuroprotection after traumatic brain injuries? A comprehensive literature review of preclinical studies." Frontiers in neurology vol. 14 1109406. Feb. 2, 2023, doi:10.3389/fneur.2023.1109406 (Year: 2023).*

Maas, Andrew I R et al. "Traumatic brain injury: progress and challenges in prevention, clinical care, and research." The Lancet. Neurology vol. 21, 11 (2022): 1004-1060. doi:10.1016/S1474-4422(22)00309-X (Year: 2022).*

Mitsika et al. 2020. "Optimized Photo-Fenton degradation of psychoactive pharmaceuticals alprazolam and diazepam using a chemometric approach—Structure and toxicity of transformation products". Journal of Hazardous Materials. DOI: 10.1016/j.jhazmat.2020.123819 (Year: 2020).*

Fiakpui, C. et al., "Synthesis and Anticonvulsant Activities of 5-(2-Chlorophenyl)-7H-pyrido[4,3-f][1,2,4]triazolo[4,3-a][1,4]diazepines" J Heterocyclic Chem 36(2):377-380 (Mar. 31, 1999).

Forkuo, G., et al., "Alleviation of Multiple Asthmatic Pathologic Features with Orally Available and Subtype Selective GABA A Receptor Modulators" Mol Pharm 14(6):2088-2098 (Jun. 5, 2017).

"International Preliminary Report on Patentability—PCT/EP2022/077509" (Report Issuance Date: Apr. 9, 2024; Chapter I),:pp. 1-6 (Apr. 18, 2024).

"International Search Report—PCT/EP2022/077509" (w/Written Opinion),:pp. 1-12 (Jan. 13, 2023).

Kolbah, D., et al., "Stereoselective in-vitro aromatic-ring oxygenations of chiral 1,4-benzodiazepin-2-ones" Hel V Chim Acta 60(1):265-283 (Jan. 26, 1977).

Kooistra, T., et al., "Triazolobenzodiazepines: a new class of stimulators of tissue-type plasminogen activator synthesis in human endothelial cells" Biochem Pharmacol 46(1):61-67 (Jul. 6, 1993).

Lee, S., et al., "Axial chirality and affinity at the GABA(A) receptor of pyrimido[1,2-a][1,4]benzodiazepines and related compounds" Bioorg Med Chem 16(21):9519-9523 (Nov. 1, 2008).

Svetlov, S., et al., "The specific binding of the platelet-activating factor (PAF) receptor antagonist WEB 2086 and the benzodiazepine flunitrazepam to rat hepatocytes" Life Sci 58(5):PL81-PL86 (Dec. 1, 1995).

Waters, L. et al., "The use of a quantitative structure-activity relationship (QSAR) model to predict GABA-A receptor binding of newly emerging benzodiazepines" Sci Justice 58(5):219-225 (May 1, 2018).

Watjen, F., et al., "Novel benzodiazepine receptor partial agonists: oxadiazolylimidazobenzodiazepines" J Med Chem 32(10):2282-2291 (Jan. 1, 1989).

* cited by examiner

BENZODIAZEPINE DERIVATIVES AS GABA A GAMMA1 PAM

CROSS-REFERENCE TO RELATED APPLICATIONS

This application claims priority to European Application No. EP21201128.2 filed on Oct. 6, 2021, the disclosure of which is incorporated herein by reference.

FIELD OF THE INVENTION

The present invention relates to organic compounds useful for therapy or prophylaxis in a mammal, and in particular to new benzodiazepine derivatives that exhibit activity as GABAA γ1 receptor positive allosteric modulators (PAMs) and are thus useful for the treatment or prophylaxis of GABAA γ1 receptor related diseases or conditions.

BACKGROUND OF THE INVENTION

Receptors for the major inhibitory neurotransmitter, gamma-aminobutyric acid (GABA), are divided into two main classes: (1) $GABA_A$ receptors, which are members of the ligand-gated ion channel superfamily and (2) $GABA_B$ receptors, which are members of the G-protein linked receptor family. The $GABA_A$ receptor complex which is a membrane-bound heteropentameric protein polymer is composed principally of α, β and γ subunits. $GABA_A$ receptors are ligand-gated chloride channels and the principal mediators of inhibitory neurotransmission in the human brain.

There are 19 genes encoding for $GABA_A$ receptor subunits that assemble as pentamers with the most common stoichiometry being two α, two β and one γ subunit. $GABA_A$ subunit combinations give rise to functional, circuit, and behavioral specificity. $GABA_A$ receptors containing the γ1 subunit ($GABA_A$ γ1) are of particular interest due to their enriched expression in the limbic system and unique physiological and pharmacological properties. The $GABA_A$ γ1 subunit-containing receptors, while less abundant (around 5-10% of total expression of $GABA_A$ receptors in the brain) than γ2 subunit-containing receptors exhibit an enriched brain mRNA and protein distribution in key brain areas such as extended amygdala (central, medial, and bed nucleus of the stria terminalis), lateral septum, hypothalamus, and pallidum/nigra. These structures form the interconnected core of a subcortical limbic circuit regulating motivated social and affective behaviors. In abnormal or disease conditions, hyper-recruitment of this circuit promotes anxiety, arousal, aggression, fear and defense while inhibiting foraging and social interactions.

Hyperactivity in limbic cortical regions (known to form a coordinated functional network with extended amygdala/hypothalamus regions) which are key areas for processing of social and emotionally relevant stimuli, is the common hallmark of a variety of psychiatric, neurological, neurodevelopmental, neurodegenerative, mood, motivational and metabolic disorders. In such a disease state, and given the characteristic anatomical distribution of the γ1 subunit-containing $GABA_A$ receptors, a $GABA_A$ γ1 positive allosteric modulator (PAM) may be an effective treatment as a symptomatic or disease-modifying agent.

Multiple lines of evidence suggest that an imbalance between excitatory/inhibitory (E/I) neurotransmission arising from dysfunction of GABAergic signaling system, the main inhibitory neurotransmitter system in the brain, to be at the core of the pathogenesis a variety of CNS disorders.

Given the distribution and function of $GABA_A$ γ1 subunit-containing receptors in the CNS, they are very attractive targets for restoring levels of inhibition within key brain circuits and consequently the E/I balance in these conditions.

A CNS disorders of particular interest in the context of the present invention is autism spectrum disorder (ASD), including its core symptoms and associated comorbidities, such as anxiety and irritability, social anxiety disorder (social phobia) and generalized anxiety disorder. ASD is a complex, heterogeneous neurodevelopmental disorder characterized by impairments in two core domains: impairments in social interaction and communication, and presence of repetitive or restricted behaviors, interests, or activities (American Psychiatric Association 2013).

No approved pharmacological treatment exists for core symptoms of social deficits and restricted/repetitive behaviour of ASD, while only inadequate therapeutic options are available for most of ASD's affective and physiological co-morbidities. As a result, this disorder continues to be an area of high unmet medical need. Current approved treatments for associated symptoms of ASD are limited to the antipsychotics (Risperidone and Aripiprazole) indicated for the treatment of irritability associated with ASD symptoms. Emerging evidence suggests that the GABAergic system, the main inhibitory neurotransmitter system in the brain, plays a key role in the pathophysiology of ASD.

Both genetic and imaging studies using positron emission tomography study (PET) and magnetic resonance spectroscopy (MRS) suggest alterations in GABAergic signaling in ASD. The gene encoding $GABA_A$ γ1, GABRG1, is located on chromosome 4 (mouse Chr.5) in a cluster with genes encoding α2, α4 and β1 $GABA_A$ receptor subunits. Rare CNVs, including inversion of chromosome 4p12 disrupting GABRG1 have been observed in autistic siblings (Horike et al., 2006), as well as GABRG1 loss in one case of ADHD. Mutations in 4p12 gene cluster have been linked to increased risk of anxiety, substance abuse and eating disorders—providing a link between GABRG1/4p12 and affective dysfunction. MRS studies found altered GABA levels in ASD and in particular some recent studies showed reduced GABA and altered somatosensory function in children with ASD. In line with these observations, a reduced number of inhibitory interneurons were found from postmortem tissues of ASD and TS patients. Furthermore, reduced GABA synthesizing enzymes, glutamic acid decarboxylase (GAD) 65 and 67 were found in parietal and cerebellar cortices of patients with autism. Strong evidence in humans points to specific dysfunction in ASD of the limbic cortical regions known to form a coordinated functional network with $GABA_A$ γ1 subunit-containing extended amygdala/hypothalamus regions. These areas: Cortical/lateral amygdala, Insula, PFC, and Cingulate are recognized key for processing of social and emotionally relevant stimuli. While subcortical subnuclei that form specific partnerships with these areas, coordinating behavioural outcomes, are often difficult to study due to spatial resolution limitations, many lines of evidence point to hyper-recruitment of these cortical- to sub cortical connections in ASD. Moreover, recent high resolution studies provide a clear link between extended amygdala activity/functional connectivity and emotional state. Targeting such highly specified limbic subcortical regions, which exhibit substantial molecular and cellular diversity compared to the neocortex, will create a precision entry point for safe and specific therapeutic modulation of ASD-affected socio-affective circuits, while avoiding broad modulation of global brain state. Enhancement of GABA$_A$ receptor activity by non-selective BZDs have been shown to ameliorate behavioral deficits in mouse models of ASD, however very narrow therapeutic margins were observed due to sedation mediated by the GABA$_A$ α1γ2 subtype. These findings support the notion that rebalancing of GABAergic transmission via GABA$_A$ γ1 receptors can improve symptoms in ASD without the side effects of non-selective benzodiazepines.

SUMMARY OF THE INVENTION

Compounds of the present invention are selective GABA$_A$ γ1 receptor positive allosteric modulators (PAMs) that selectively enhance the function of γ1-containing GABA$_A$ receptors by increasing GABAergic currents (influx of chloride) at a given concentration (e.g. EC$_{20}$) of gamma amino butyric acid (GABA). The compounds of the present invention have high PAM efficacy and binding selectivity for the γ1-containing subtypes (α5γ1, α2γ1, α1γ1) relative to the γ2-containing subtypes (e.g. α1γ2, α2γ2, α3γ2 and α5γ2). As such, compounds of the present invention are strongly differentiated from classical benzodiazepine drugs such as Alprazolam, Triazolam, Estazolam, and Midazolam, which are selective for the γ2-containing GABA$_A$ subtypes and possess low affinity for the γ1-containing subtypes. Compatible with the γ1-subtypes brain distribution, selective GABA$_A$ γ1 PAMs will restore GABAergic signaling in key brain regions (e.g. extended amygdala: central, medial, and bed nucleus of the stria terminalis, lateral septum, hypothalamus, and pallidum/nigra) without the side-effects of non-selective GABA$_A$ modulators (e.g. benzodiazepines).

In view of the above, the selective GABA$_A$ γ1 PAMs described herein and their pharmaceutically acceptable salts and esters are useful, alone or in combination with other drugs, as disease-modifying or as symptomatic agents for the treatment or prevention of acute neurological disorders, chronic neurological disorders and/or cognitive disorders, including autism spectrum disorders (ASD), Angelman syndrome, age-related cognitive decline, Rett syndrome, Prader-Willi syndrome, amyotrophic lateral sclerosis (ALS), fragile-X disorder, negative and/or cognitive symptoms associated with schizophrenia, tardive dyskinesia, anxiety, social anxiety disorder (social phobia), panic disorder, agoraphobia, generalized anxiety disorder, disruptive, impulse-control and conduct disorders, Tourette's syndrome (TS), obsessive-compulsive disorder (OCD), acute stress disorder, post-traumatic stress disorder (PTSD), attention deficit hyperactivity disorder (ADHD), sleep disorders, Parkinson's disease (PD), Huntington's chorea, Alzheimer's disease (AD), mild cognitive impairment (MCI), dementia, behavioral and psychological symptoms (BPS) in neurodegenerative conditions, multi-infarct dementia, agitation, psychosis, substance-induced psychotic disorder, aggression, eating disorders, depression, chronic apathy, anhedonia, chronic fatigue, seasonal affective disorder, postpartum depression, drowsiness, sexual dysfunction, bipolar disorders, epilepsy and pain.

In a first aspect, the present invention provides a compound of formula (I) or (II)

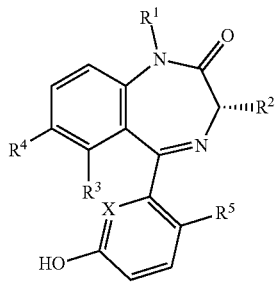

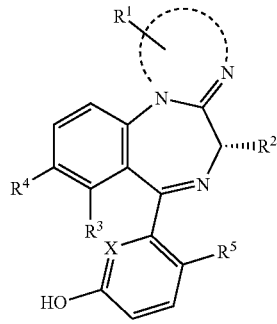

or a pharmaceutically acceptable salt thereof, wherein the variables are as defined herein.

In one aspect, the present invention provides a process of manufacturing the compounds of formula (I) or (II) described herein, wherein said process is as described in any one of Schemes 1 to 14 herein.

In a further aspect, the present invention provides a compound of formula (I) or (II) as described herein, when manufactured according to the processes described herein.

In a further aspect, the present invention provides a compound of formula (I) or (II) as described herein, or a pharmaceutically acceptable salt thereof, for use as therapeutically active substance.

In a further aspect, the present invention provides a pharmaceutical composition comprising a compound of formula (I) or (II) as described herein, or a pharmaceutically acceptable salt thereof, and a therapeutically inert carrier.

In a further aspect, the present invention provides a compound of formula (I) or (II) as described herein, or a pharmaceutically acceptable salt thereof, for use in a method for treating or preventing acute neurological disorders, chronic neurological disorders and/or cognitive disorders in a subject.

DETAILED DESCRIPTION OF THE INVENTION

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" refers to a mono- or multivalent, e.g., a mono- or bivalent, linear or branched saturated hydrocarbon group of 1 to 6 carbon atoms ("$C_1$-$C_6$-alkyl"), e.g., 1, 2, 3, 4, 5, or 6 carbon atoms. In some embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. Particularly preferred, yet non-limiting examples of alkyl include methyl and ethyl.

The term "alkoxy" refers to an alkyl group, as previously defined, attached to the parent molecular moiety via an oxygen atom. Unless otherwise specified, the alkoxy group contains 1 to 6 carbon atoms ("$C_1$-$C_6$-alkoxy"). In some preferred embodiments, the alkoxy group contains 1 to 4 carbon atoms. In still other embodiments, the alkoxy group contains 1 to 3 carbon atoms. Some non-limiting examples of alkoxy groups include methoxy, ethoxy, n-propoxy, iso-propoxy, n-butoxy, isobutoxy and tert-butoxy. A particularly preferred, yet non-limiting example of alkoxy is methoxy.

The term "halogen" or "halo" refers to fluoro (F), chloro (Cl), bromo (Br), or iodo (I). Preferably, the term "halogen" or "halo" refers to fluoro (F), chloro (Cl) or bromo (Br). Particularly preferred, yet non-limiting examples of "halogen" or "halo" are fluoro (F) and chloro (Cl).

The term "cycloalkyl" as used herein refers to a saturated monocyclic or bicyclic hydrocarbon group of 3 to 10 ring carbon atoms ("$C_3$-$C_{10}$-cycloalkyl"). In some preferred embodiments, the cycloalkyl group is a saturated monocyclic hydrocarbon group of 3 to 8 ring carbon atoms. "Bicyclic cycloalkyl" refers to cycloalkyl moieties consisting of two saturated carbocycles having two carbon atoms in common, i.e., the bridge separating the two rings is either a single bond or a chain of one or two ring atoms, and to spirocyclic moieties, i.e., the two rings are connected via one common ring atom. Preferably, the cycloalkyl group is a saturated monocyclic hydrocarbon group of 3 to 6 ring carbon atoms, e.g., of 3, 4, 5 or 6 carbon atoms. Some non-limiting examples of cycloalkyl include cyclopropyl, cyclobutyl, cyclopentyl, cyclohexyl, cycloheptyl, and spiro[2.3]hexan-5-yl.

The term "cycloalkenyl" as used herein refers to a partly unsaturated monocyclic or bicyclic hydrocarbon group of 3 to 10 ring carbon atoms ("$C_3$-$C_{10}$-cycloalkenyl"). In some preferred embodiments, the cycloalkenyl group is a partly unsaturated monocyclic hydrocarbon group of 3 to 8 ring carbon atoms. "Bicyclic cycloalkenyl" refers to cycloalkenyl moieties consisting of two carbocycles having two carbon atoms in common, i.e., the bridge separating the two rings is either a single bond or a chain of one or two ring atoms, and to spirocyclic moieties, i.e., the two rings are connected via one common ring atom, wherein at least one of the two carbocycles is partly unsaturated. Preferably, the cycloalkenyl group is a partly unsaturated monocyclic hydrocarbon group of 3 to 6 ring carbon atoms, e.g., of 3, 4, 5 or 6 carbon atoms. Some non-limiting examples of cycloalkenyl include cyclopropenyl, cyclobutenyl, cyclopentenyl, cyclohexenyl, cycloheptenyl, and spiro[2.3]hex-5-en-5-yl.

The term "heterocyclyl" or "heterocycloalkyl" refers to a saturated or partly unsaturated mono- or bicyclic, preferably monocyclic ring system of 3 to 14 ring atoms, preferably 3 to 10 ring atoms, more preferably 3 to 8, most preferably 3 to 6 ring atoms, wherein 1, 2, or 3 of said ring atoms are heteroatoms selected from N, O and S, the remaining ring atoms being carbon. Preferably, 1 to 2 of said ring atoms are selected from N and O, the remaining ring atoms being carbon. "Bicyclic heterocyclyl" refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. Some non-limiting examples of heterocyclyl groups include azetidin-3-yl; azetidin-2-yl; oxetan-3-yl; oxetan-2-yl; oxazolidinyl; piperidyl; piperazinyl; pyrrolidinyl; 2-oxopyrrolidin-1-yl; 2-oxopyrrolidin-3-yl; 5-oxopyrrolidin-2-yl; 5-oxopyrrolidin-3-yl; 2-oxo-1-piperidyl; 2-oxo-3-piperidyl; 2-oxo-4-piperidyl; 6-oxo-2-piperidyl; 6-oxo-3-piperidyl; 1-piperidinyl; 2-piperidinyl; 3-piperidinyl; 4-piperidinyl; morpholino (e.g., morpholin-2-yl or morpholin-3-yl); thiomorpholino; pyrrolidinyl (e.g., pyrrolidin-3-yl); 1-oxa-6-azaspiro[3.3]heptane; 2-oxa-6-azaspiro[3.3]heptane; 5-oxa-2-azaspiro[3.4]octane; 6-oxa-2-azaspiro[3.4]octane; 5-oxa-2-azaspiro[3.5]nonane; 6-oxa-2-azaspiro[3.5]nonane; 7-oxa-2-azaspiro[3.5]nonane; 3-oxa-6-azabicyclo[3.1.1]heptane; 3-thia-6-azabicyclo[3.1.1]heptane; 3-azabicyclo[3.1.0]hexan-6-yl; 2,5-diazabicyclo[2.2.1]heptan-2-yl; 2-azaspiro[3.3]heptan-2-yl; 2,6-diazaspiro[3.3]heptan-2-yl; and 2,3,3a,4,6,6a-hexahydro-1H-pyrrolo[3,4-c]pyrrol-5-yl. A preferred, yet non-limiting example of heterocyclyl includes azetidinyl.

The term "haloalkyl" refers to an alkyl group, wherein at least one of the hydrogen atoms of the alkyl group has been replaced by a halogen atom, preferably fluoro. Preferably, "haloalkyl" refers to an alkyl group wherein 1, 2 or 3 hydrogen atoms of the alkyl group have been replaced by a halogen atom, most preferably fluoro. Non-limiting examples of haloalkyl are fluoromethyl, difluoromethyl, trifluoromethyl, trifluoroethyl, 2-fluoroethyl, and 2,2-difluoroethyl. A particularly preferred, yet non-limiting example of haloalkyl is trifluoromethyl.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as formic acid, acetic acid, trifluoroacetic acid, propionic acid, glycolic acid, pyruvic acid, oxalic acid, maleic acid, malonic acid, succinic acid, fumaric acid, tartaric acid, lactic acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochlorides, fumarates, formates, lactates (in particular derived from L-(+)-lactic acid), tartrates (in particular derived from L-(+)-tartaric acid) and trifluoroacetates.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention, the asymmetric carbon atom can be of the "R" or "S" configuration.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" or "prevention" as used herein includes: preventing or delaying the appearance of clinical symptoms of the state, disorder or condition developing in a subject and especially a human that may be afflicted with or predisposed to the state, disorder or condition but does not yet experience or display clinical or subclinical symptoms of the state, disorder or condition.

The term "subject" as used herein includes both humans and non-humans and includes but is not limited to humans, non-human primates, canines, felines, murines, bovines, equines, and porcines.

In a particularly preferred embodiment, the term "subject" refers to humans.

The abbreviation uM means microMolar and is equivalent to the symbol μM.

The abbreviation uL means microliter and is equivalent to the symbol μL.

The abbreviation ug means microgram and is equivalent to the symbol μg.

Compounds of the Invention

In a first aspect, the present invention provides a compound of formula (I) or (II)

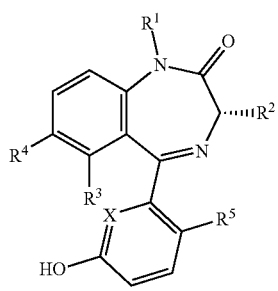

(I)

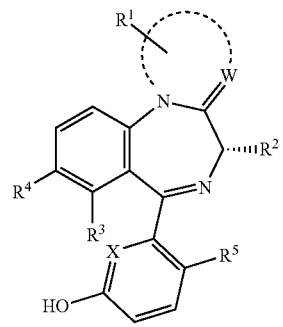

(II)

or a pharmaceutically acceptable salt thereof, wherein:

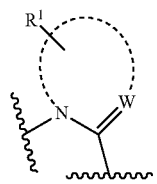

is selected from:

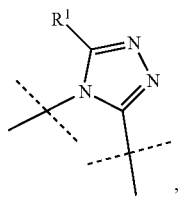

i)

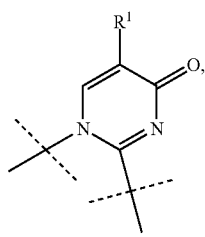

ii)

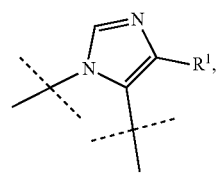

iii)

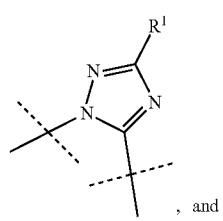

iv)

, and

-continued v)

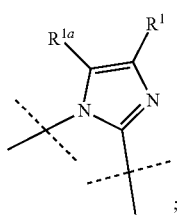

X is selected from C—R$^6$ and nitrogen;
W is C or N;
R$^1$ is selected from hydrogen, C$_1$-C$_6$-alkyl, carbamoyl, C$_1$-C$_6$-alkyl-NH—C(O)—, (C$_1$-C$_6$-alkyl)$_2$N—C(O)—, C$_3$-C$_{10}$-cycloalkyl-NH—C(O)—, and 3-14-membered heterocycloalkyl-C(O)—; wherein said 3-14-membered heterocycloalkyl is optionally substituted by 1 substituent selected from halogen and C$_1$-C$_6$-alkoxy;
R$^{1a}$ is selected from hydrogen and C$_1$-C$_6$-alkyl; or
R$^1$ and R$^{1a}$, taken together with the carbon atoms to which they are attached, form a C$_3$-C$_{10}$-cycloalkenyl;
R$^2$ is selected from hydrogen and C$_1$-C$_6$-alkyl;
R$^3$ is selected from chloro and bromo;
R$^4$ is selected from C$_1$-C$_3$-alkyl, halo-C$_1$-C$_2$-alkyl, and halogen;
R$^5$ is selected from hydrogen and halogen; and
R$^6$ is selected from hydrogen and halogen.

In one embodiment, the compound according to the present invention is a compound of formula (I)

(I)

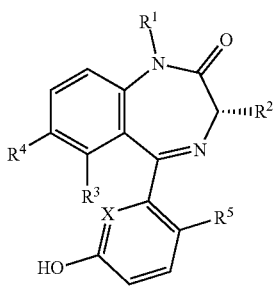

or a pharmaceutically acceptable salt thereof, wherein the variables are as described herein.

In one embodiment, the compound according to the present invention is a compound of formula (II)

(II)

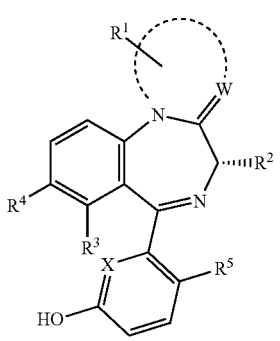

or a pharmaceutically acceptable salt thereof, wherein the variables are as described herein.

In a preferred embodiment, the compound according to the present invention is a compound of formula (II), or a pharmaceutically acceptable salt thereof, wherein:

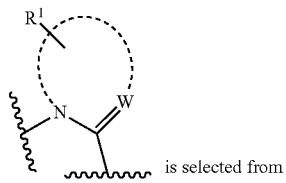 is selected from iv)

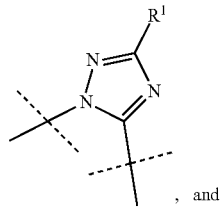

, and v)

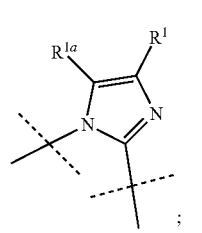

;

and the remaining variables are as described herein.

In one embodiment, the compound according to the present invention is a compound of formula (II), or a pharmaceutically acceptable salt thereof, wherein:
and the remaining variables are as described herein.

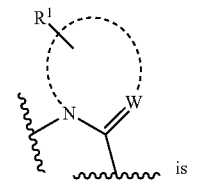 is i)

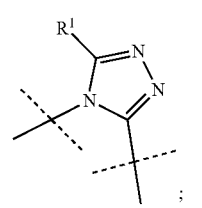

;

In one embodiment, the compound according to the present invention is a compound of formula (II), or a pharmaceutically acceptable salt thereof, wherein:

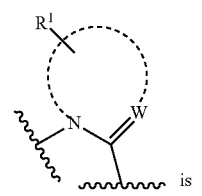 is

-continued

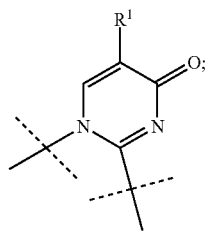
ii)

and the remaining variables are as described herein.

In one embodiment, the compound according to the present invention is a compound of formula (II), or a pharmaceutically acceptable salt thereof, wherein:

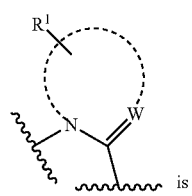
iii)

and the remaining variables are as described herein.

In one embodiment, the compound according to the present invention is a compound of formula (II), or a pharmaceutically acceptable salt thereof, wherein:

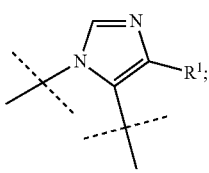
iv)

and the remaining variables are as described herein.

In one embodiment, the compound according to the present invention is a compound of formula (II), or a pharmaceutically acceptable salt thereof, wherein:

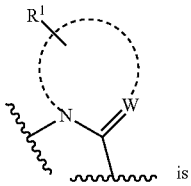
is

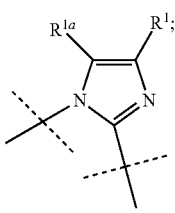
v)

and the remaining variables are as described herein.

In one embodiment, the compound according to the present invention is a compound of formula (I), or a pharmaceutically acceptable salt thereof, wherein $R^1$ is $C_1$-$C_6$-alkyl and the remaining variables are as described herein.

In one embodiment, the compound according to the present invention is a compound of formula (I), or a pharmaceutically acceptable salt thereof, wherein $R^1$ is methyl and the remaining variables are as described herein.

In one embodiment, the present invention provides a compound of formula (I) or (II) as described herein, or a pharmaceutically acceptable salt thereof, wherein

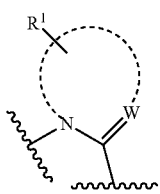

is selected from:

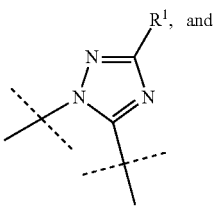
iv)

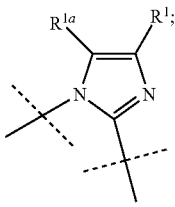
v)

$R^1$ is selected from hydrogen, $C_1$-$C_6$-alkyl, and 3-14-membered heterocycloalkyl-C(O)—; wherein said 3-14-membered heterocycloalkyl is substituted by 1 $C_1$-$C_6$-alkoxy substituent; and
$R^{1a}$ is $C_1$-$C_6$-alkyl.

In a preferred embodiment, the present invention provides a compound of formula (I) or (II) as described herein, or a pharmaceutically acceptable salt thereof, wherein

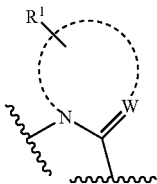

is selected from:

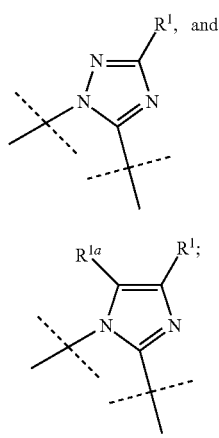

R$^1$ is selected from hydrogen, methyl, and methoxyazetidine-C(O)—; and
R$^{1a}$ is methyl.

In one embodiment, the present invention provides a compound of formula (I) as described herein, or a pharmaceutically acceptable salt thereof, wherein
R$^1$ is selected from hydrogen, C$_1$-C$_6$-alkyl, and 3-14-membered heterocycloalkyl-C(O)—; wherein said 3-14-membered heterocycloalkyl is substituted by 1 C$_1$-C$_6$-alkoxy substituent; and
R$^{1a}$ is C$_1$-C$_6$-alkyl.

In a preferred embodiment, the present invention provides a compound of formula (I) as described herein, or a pharmaceutically acceptable salt thereof, wherein
R$^1$ is selected from hydrogen, methyl, and methoxyazetidine-C(O)—; and
R$^{1a}$ is methyl.

In a preferred embodiment, the present invention provides a compound of formula (I) as described herein, or a pharmaceutically acceptable salt thereof, wherein R$^2$ is selected from hydrogen and methyl.

In a preferred embodiment, the present invention provides a compound of formula (I) as described herein, or a pharmaceutically acceptable salt thereof, wherein R$^3$ is chloro.

In a preferred embodiment, the present invention provides a compound of formula (I) as described herein, or a pharmaceutically acceptable salt thereof, wherein R$^4$ is selected from methyl, CF$_3$, and chloro.

In a particularly preferred embodiment, the present invention provides a compound of formula (I) or (II) as described herein, or a pharmaceutically acceptable salt thereof, wherein R$^4$ is selected from methyl and CF$_3$.

In one embodiment, the present invention provides a compound of formula (I) or (II) as described herein, or a pharmaceutically acceptable salt thereof, wherein R$^4$ is methyl.

In one embodiment, the present invention provides a compound of formula (I) or (II) as described herein, or a pharmaceutically acceptable salt thereof, wherein R$^4$ is CF$_3$.

In one embodiment, the present invention provides a compound of formula (I) or (II) as described herein, or a pharmaceutically acceptable salt thereof, wherein R$^4$ is chloro.

In one embodiment, the present invention provides a compound of formula (I) or (II) as described herein, or a pharmaceutically acceptable salt thereof, wherein R$^5$ is halogen.

In a preferred embodiment, the present invention provides a compound of formula (I) or (II) as described herein, or a pharmaceutically acceptable salt thereof, wherein R$^5$ is selected from chloro and fluoro.

In one embodiment, the present invention provides a compound of formula (I) or (II) as described herein, or a pharmaceutically acceptable salt thereof, wherein R$^5$ is chloro.

In one embodiment, the present invention provides a compound of formula (I) or (II) as described herein, or a pharmaceutically acceptable salt thereof, wherein R$^5$ is fluoro.

In one embodiment, the present invention provides a compound of formula (I) or (II) as described herein, or a pharmaceutically acceptable salt thereof, wherein R$^6$ is hydrogen.

In one embodiment, the present invention provides a compound of formula (I) or (II) as described herein, or a pharmaceutically acceptable salt thereof, wherein R$^6$ is halogen.

In one embodiment, the present invention provides a compound of formula (I) or (II) as described herein, or a pharmaceutically acceptable salt thereof, wherein R$^6$ is fluoro.

In one embodiment, the present invention provides a compound of formula (I) or (II) as described herein, or a pharmaceutically acceptable salt thereof, wherein R$^6$ is hydrogen or fluoro.

In one embodiment, the present invention provides a compound of formula (I) or (II) as described herein, or a pharmaceutically acceptable salt thereof, wherein:

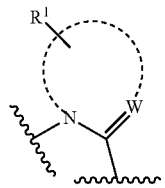

is selected from:

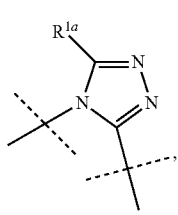

-continued ii)

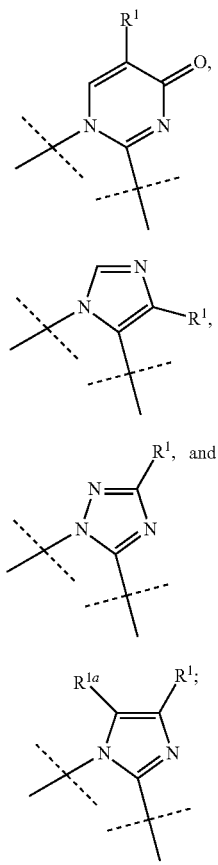

iii)

iv)

v)

X is selected from C—R⁶ and nitrogen;
R¹ is selected from hydrogen, $C_1$-$C_6$-alkyl, $C_1$-$C_6$-alkyl-NH—C(O)—, $C_3$-$C_{10}$-cycloalkyl-NH—C(O)—, and 3-14-membered heterocycloalkyl-C(O)—; wherein said 3-14-membered heterocycloalkyl is optionally substituted by 1 substituent selected from halogen and $C_1$-$C_6$-alkoxy;
$R^{1a}$ is selected from hydrogen and $C_1$-$C_6$-alkyl; or
$R^1$ and $R^{1a}$, taken together with the carbon atoms to which they are attached, form a $C_3$-$C_{10}$-cycloalkenyl;
R² is selected from hydrogen and $C_1$-$C_6$-alkyl;
R³ is chloro;
R⁴ is selected from $C_1$-$C_3$-alkyl, halo-$C_1$-$C_2$-alkyl, and halogen;
R⁵ is halogen; and
R⁶ is selected from hydrogen and halogen.

In a preferred embodiment, the present invention provides a compound of formula (I) or (II) as described herein, or a pharmaceutically acceptable salt thereof, wherein:

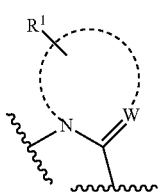

is selected from:

iv)

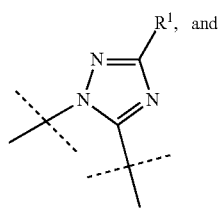

v)

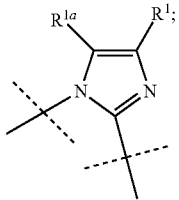
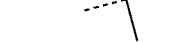

X is selected from C—R⁶ an nitrogen;
R¹ is selected from hydrogen, $C_1$-$C_6$-alkyl, and 3-14-membered heterocycloalkyl-C(O)—; wherein said 3-14-membered heterocycloalkyl is substituted by 1 $C_1$-$C_6$-alkoxy substituent;
$R^{1a}$ is $C_1$-$C_6$-alkyl;
R² is selected from hydrogen and $C_1$-$C_6$-alkyl;
R³ is chloro;
R⁴ is selected from $C_1$-$C_3$-alkyl, halo-$C_1$-$C_2$-alkyl, and halogen;
R⁵ is halogen; and
R⁶ is hydrogen.

In a particularly preferred embodiment, the present invention provides a compound of formula (I) or (II) as described herein, or a pharmaceutically acceptable salt thereof, wherein:

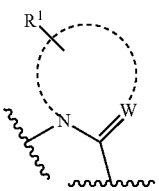

is selected from:

iv)

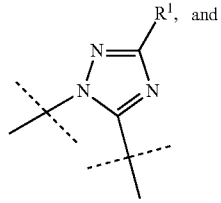

v)

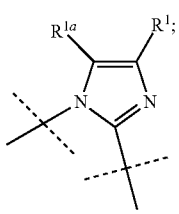

X is selected from C—R⁶ and nitrogen;
R¹ is selected from hydrogen, methyl, and methoxyazetidine-C(O)—;
R¹ᵃ is methyl;
R² is selected from hydrogen and methyl;
R³ is chloro;
R⁴ is selected from methyl, CF₃, and chloro;
R⁵ is selected from chloro and fluoro; and
R⁶ is hydrogen.

In one embodiment, the present invention provides a compound of formula (I) or (II) as described herein, or a pharmaceutically acceptable salt thereof, wherein said compound of formula (I) or (II) is selected from:

6,7-dichloro-5-(2-fluoro-5-hydroxyphenyl)-1-methyl-1,3-dihydro-2H-benzo[e][1,4]diazepin-2-one;
6-chloro-5-(2-fluoro-5-hydroxyphenyl)-1,7-dimethyl-1,3-dihydro-2H-benzo[e][1,4]diazepin-2-one;
3-(7,8-dichloro-1-methyl-4H-[1,2,4]triazolo[4,3-a][1,4]benzodiazepin-6-yl)-4-fluoro-phenol;
3-[(4S)-7,8-dichloro-1,4-dimethyl-4H-[1,2,4]triazolo[4,3-a][1,4]benzodiazepin-6-yl]-4-fluorophenol;
(5S)-8,9-dichloro-7-(2-fluoro-5-hydroxyphenyl)-5-methyl-5H-pyrimido[1,2-a][1,4]benzodiazepin-3-one;
8,9-dichloro-7-(2-fluoro-5-hydroxy-phenyl)-5H-pyrimido[1,2-a][1,4]benzodiazepin-3-one; [7,8-dichloro-6-(2-fluoro-5-hydroxy-phenyl)-4H-[1,2,4]triazolo[1,5-a][1,4]benzodiazepin-2-yl]-(3-methoxyazetidin-1-yl)methanone;
6-chloro-5-(2-fluoro-5-hydroxy-phenyl)-1-methyl-7-(trifluoromethyl)-3H-1,4-benzodiazepin-2-one;
3-[7-chloro-1-methyl-8-(trifluoromethyl)-4H-[1,2,4]triazolo[4,3-a][1,4]benzodiazepin-6-yl]-4-fluoro-phenol;
3-[7-chloro-8-(trifluoromethyl)-4H-[1,2,4]triazolo[4,3-a][1,4]benzodiazepin-6-yl]-4-fluoro-phenol;
3-[(4S)-7-chloro-1,4-dimethyl-8-(trifluoromethyl)-4H-[1,2,4]triazolo[4,3-a][1,4]benzodiazepin-6-yl]-4-fluoro-phenol;
8-chloro-7-(2-fluoro-5-hydroxy-phenyl)-9-(trifluoromethyl)-5H-pyrimido[1,2-a][1,4]benzodiazepin-3-one;
6,7-dichloro-5-(2,6-difluoro-3-hydroxy-phenyl)-1-methyl-3H-1,4-benzodiazepin-2-one;
3-(7,8-dichloro-1-methyl-4H-[1,2,4]triazolo[4,3-a][1,4]benzodiazepin-6-yl)-2,4-difluoro-phenol;
8,9-dichloro-7-(2,6-difluoro-3-hydroxy-phenyl)-5H-pyrimido[1,2-a][1,4]benzodiazepin-3-one;
3-[(4S)-7,8-dichloro-1,4-dimethyl-4H-[1,2,4]triazolo[4,3-a][1,4]benzodiazepin-6-yl]-2,4-difluoro-phenol;
[7-chloro-6-(2-fluoro-5-hydroxy-phenyl)-8-(trifluoromethyl)-4H-[1,2,4]triazolo[1,5-a][1,4]benzodiazepin-2-yl]-(3-methoxyazetidin-1-yl)methanone;
(5S)-8,9-dichloro-7-(2,6-difluoro-3-hydroxy-phenyl)-5-methyl-5H-pyrimido[1,2-a][1,4]benzodiazepin-3-one;
[7-chloro-6-(2-fluoro-5-hydroxy-phenyl)-8-(trifluoromethyl)-4H-imidazo[1,5-a][1,4]benzodiazepin-3-yl]-(3-methoxyazetidin-1-yl)methanone;
6-[(4S)-7-chloro-1,4-dimethyl-8-(trifluoromethyl)-4H-[1,2,4]triazolo[4,3-a][1,4]benzodiazepin-6-yl]-5-fluoro-pyridin-2-ol;
[(4S)-7-chloro-6-(3-fluoro-6-hydroxy-2-pyridyl)-4-methyl-8-(trifluoromethyl)-4H-[1,2,4]triazolo[1,5-a][1,4]benzodiazepin-2-yl]-(3-fluoroazetidin-1-yl)methanone;
5-chloro-6-[(4S)-7-chloro-1,4-dimethyl-8-(trifluoromethyl)-4H-[1,2,4]triazolo[4,3-a][1,4]benzodiazepin-6-yl]pyridin-2-ol;
6-[(4S)-7-chloro-1,4-dimethyl-8-(trifluoromethyl)-4H-imidazo[1,2-a][1,4]benzodiazepin-6-yl]-5-fluoro-pyridin-2-ol;
6-[(10S)-6-chloro-10-methyl-5-(trifluoromethyl)-1,9,12-triazatetracyclo[9.6.0.0²,⁷.0¹³,¹⁷]heptadeca-2,4,6,8,11,13(17)-hexaen-8-yl]-5-fluoro-pyridin-2-ol;
6-[(4S)-7-chloro-2,4-dimethyl-8-(trifluoromethyl)-4H-[1,2,4]triazolo[1,5-a][1,4]benzodiazepin-6-yl]-5-fluoropyridin-2-ol;
5-chloro-6-[(4S)-7-chloro-1,4-dimethyl-8-(trifluoromethyl)-4H-imidazo[1,2-a][1,4]benzodiazepin-6-yl]pyridin-2-ol;
5-chloro-6-[(4S)-7-chloro-2,4-dimethyl-8-(trifluoromethyl)-4H-imidazo[1,2-a][1,4]benzodiazepin-6-yl]pyridin-2-ol;
6-[(4S)-7-chloro-2,4-dimethyl-8-(trifluoromethyl)-4H-imidazo[1,2-a][1,4]benzodiazepin-6-yl]-5-fluoro-pyridin-2-ol;
5-chloro-6-[(4S)-7-chloro-2,4-dimethyl-8-(trifluoromethyl)-4H-[1,2,4]triazolo[1,5-a][1,4]benzodiazepin-6-yl]pyridin-2-ol;
azetidin-1-yl-[(4S)-7-chloro-6-(3-fluoro-6-hydroxypyridin-2-yl)-4-methyl-8-(trifluoromethyl)-4H-imidazo[1,2-a][1,4]benzodiazepin-2-yl]methanone;
(4S)-7-chloro-N-cyclopropyl-6-(3-fluoro-6-hydroxy-2-pyridyl)-4-methyl-8-(trifluoromethyl)-4H-imidazo[1,2-a][1,4]benzodiazepine-2-carboxamide;
(4S)-7-chloro-6-(3-fluoro-6-hydroxy-2-pyridyl)-N-isopropyl-4-methyl-8-(trifluoromethyl)-4H-imidazo[1,2-a][1,4]benzodiazepine-2-carboxamide.

In a preferred embodiment, the present invention provides a compound of formula (I) or (II) as described herein, or a pharmaceutically acceptable salt thereof, wherein said compound of formula (I) or (II) is selected from:

6,7-dichloro-5-(2-fluoro-5-hydroxyphenyl)-1-methyl-1,3-dihydro-2H-benzo[e][1,4]diazepin-2-one;
6-chloro-5-(2-fluoro-5-hydroxyphenyl)-1,7-dimethyl-1,3-dihydro-2H-benzo[e][1,4]diazepin-2-one;
6-chloro-5-(2-fluoro-5-hydroxy-phenyl)-1-methyl-7-(trifluoromethyl)-3H-1,4-benzodiazepin-2-one;
[7-chloro-6-(2-fluoro-5-hydroxy-phenyl)-8-(trifluoromethyl)-4H-[1,2,4]triazolo[1,5-a][1,4]benzodiazepin-2-yl]-(3-methoxyazetidin-1-yl)methanone;
6-[(4S)-7-chloro-1,4-dimethyl-8-(trifluoromethyl)-4H-imidazo[1,2-a][1,4]benzodiazepin-6-yl]-5-fluoro-pyridin-2-ol;
5-chloro-6-[(4S)-7-chloro-1,4-dimethyl-8-(trifluoromethyl)-4H-imidazo[1,2-a][1,4]benzodiazepin-6-yl]pyridin-2-ol.

In a particularly preferred embodiment, the present invention provides a compound of formula (I) or (II) as described herein, or a pharmaceutically acceptable salt thereof, wherein said compound of formula (I) or (II) is 6,7-dichloro-5-(2-fluoro-5-hydroxyphenyl)-1-methyl-1,3-dihydro-2H-benzo[e][1,4]diazepin-2-one.

In a particularly preferred embodiment, the present invention provides a compound of formula (I) or (II) as described herein, or a pharmaceutically acceptable salt thereof, wherein said compound of formula (I) or (II) is 6-chloro-5-(2-fluoro-5-hydroxyphenyl)-1,7-dimethyl-1,3-dihydro-2H-benzo[e][1,4]diazepin-2-one.

In a particularly preferred embodiment, the present invention provides a compound of formula (I) or (II) as described herein, or a pharmaceutically acceptable salt thereof, wherein said compound of formula (I) or (II) is 6-chloro-5-(2-fluoro-5-hydroxy-phenyl)-1-methyl-7-(trifluoromethyl)-3H-1,4-benzodiazepin-2-one.

In a particularly preferred embodiment, the present invention provides a compound of formula (I) or (II) as described herein, or a pharmaceutically acceptable salt thereof, wherein said compound of formula (I) or (II) is [7-chloro-6-(2-fluoro-5-hydroxy-phenyl)-8-(trifluoromethyl)-4H-[1,2,4]triazolo[1,5-a][1,4]benzodiazepin-2-yl]-(3-methoxyazetidin-1-yl)methanone.

In a particularly preferred embodiment, the present invention provides a compound of formula (I) or (II) as described herein, or a pharmaceutically acceptable salt thereof, wherein said compound of formula (I) or (II) is 6-[(4S)-7-chloro-1,4-dimethyl-8-(trifluoromethyl)-4H-imidazo[1,2-a][1,4]benzodiazepin-6-yl]-5-fluoro-pyridin-2-ol.

In a particularly preferred embodiment, the present invention provides a compound of formula (I) or (II) as described herein, or a pharmaceutically acceptable salt thereof, wherein said compound of formula (I) or (II) is 5-chloro-6-[(4S)-7-chloro-1,4-dimethyl-8-(trifluoromethyl)-4H-imidazo[1,2-a][1,4]benzodiazepin-6-yl]pyridin-2-ol.

In one embodiment, the present invention provides pharmaceutically acceptable salts of the compounds of formula (I) or (II) as described herein, especially pharmaceutically acceptable salts selected from hydrochlorides, fumarates, lactates (in particular derived from L-(+)-lactic acid), tartrates (in particular derived from L-(+)-tartaric acid) and trifluoroacetates. In yet a further particular embodiment, the present invention provides the compounds according to formula (I) or (II) as described herein in their free form (i.e., as "free bases" or "free acids", respectively).

Processes of Manufacturing

Processes for the manufacture of the compounds of formula (I) and (II) as described herein are also an object of the invention.

The preparation of compounds of formula (I) and (II) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before and in the claims, unless indicated to the contrary. In more detail, the compounds of formula (I) and (II) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations, 3rd Edition*, Richard C. Larock. John Wiley & Sons, New York, NY 2018). It is convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux temperature. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The preparation of compounds of formula (I) and (II) of the present invention may be carried out in sequential or convergent synthetic routes. Syntheses of the invention are shown in the following general schemes. The skills required for carrying out the reactions and purifications of the resulting products are known to those skilled in the art. The substituents and indices used in the following description of the processes have the significance given herein before unless indicated to the contrary.

In more detail, the compounds of formula (I) and (II) can be manufactured by the methods given below, by the methods given in the examples or by analogous methods. Appropriate reaction conditions for the individual reaction steps are known to a person skilled in the art. The reaction sequence is not limited to the one displayed in Schemes 1-14, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula (I) and (II) and their pharmaceutically acceptable salts can be prepared by the process described in the following Schemes 1-14 without in particular being restricted to the routes and conditions illustrated.

According to Scheme 1, compounds of formula (I) can be obtained in two steps according to the process described in Scheme 1. Lactams (III) can be N-alkylated with alkyl halides (e.g. iodomethane) in presence of a base such as potassium carbonate or cesium carbonate to yield N-alkyl lactams (IV) which can be deprotected under acidic condition (such as hydrobromic acid, trifluoroacetic acid) or Lewis-acidic conditions (boron tribromide, aluminumtrichloride, iodotrimethylsilane or the like) to yield compounds of formula (I).

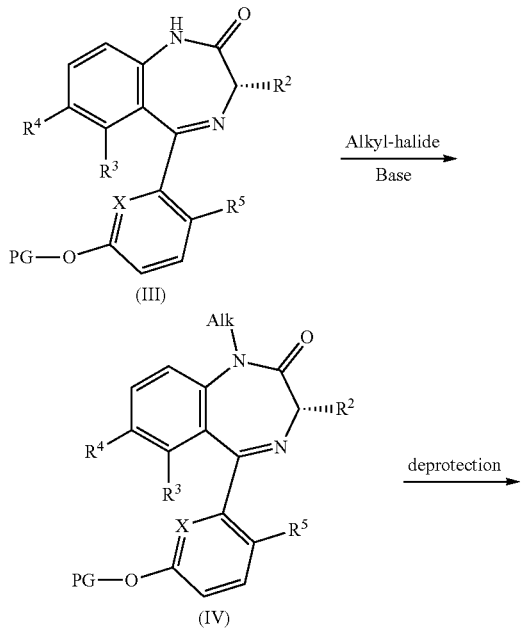

Scheme 1 synthesis of benzodiazepines of formula (I)

-continued

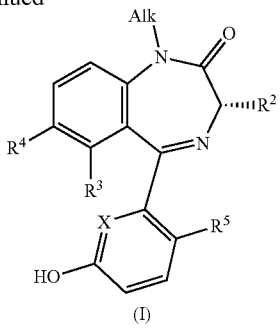

(I)

PG = methyl, tert-butyldimethylsilyl, benzyl

According to Scheme 2, a compound of formula (IIa) can be prepared from lactames of formula (II).

zine to form hydrazones (VIII) followed by treatment with the corresponding trialkyl orthoacetate or acid chloride (IX). Furthermore, lactams (III) can be directly converted into a compound of formula (VII) by treatment with an amide coupling reagent such as bis(2-oxo-3-oxazolidinyl)phosphinic chloride and hydrazides (VI) in presence of a strong base such as sodium hydride. Final derivatives of formula (IIa) can be obtained by a deprotection reaction of compound (VII) under acidic condition (such as hydrobromic acid, trifluoroacetic acid) or Lewis-acidic conditions (boron tribromide, aluminiumtrichloride, iodotrimethylsilane or the like).

In certain embodiments of the invention, compounds of formula (IIIc) can be prepared from lactams (III) according to the process described below (Scheme 3). Electrophilic amination of lactams (III) using a suitable reagent such as O-(diphenylphosphinyl)hydroxylamine yields intermediates of formula (X). Their thermal cyclocondensation reaction

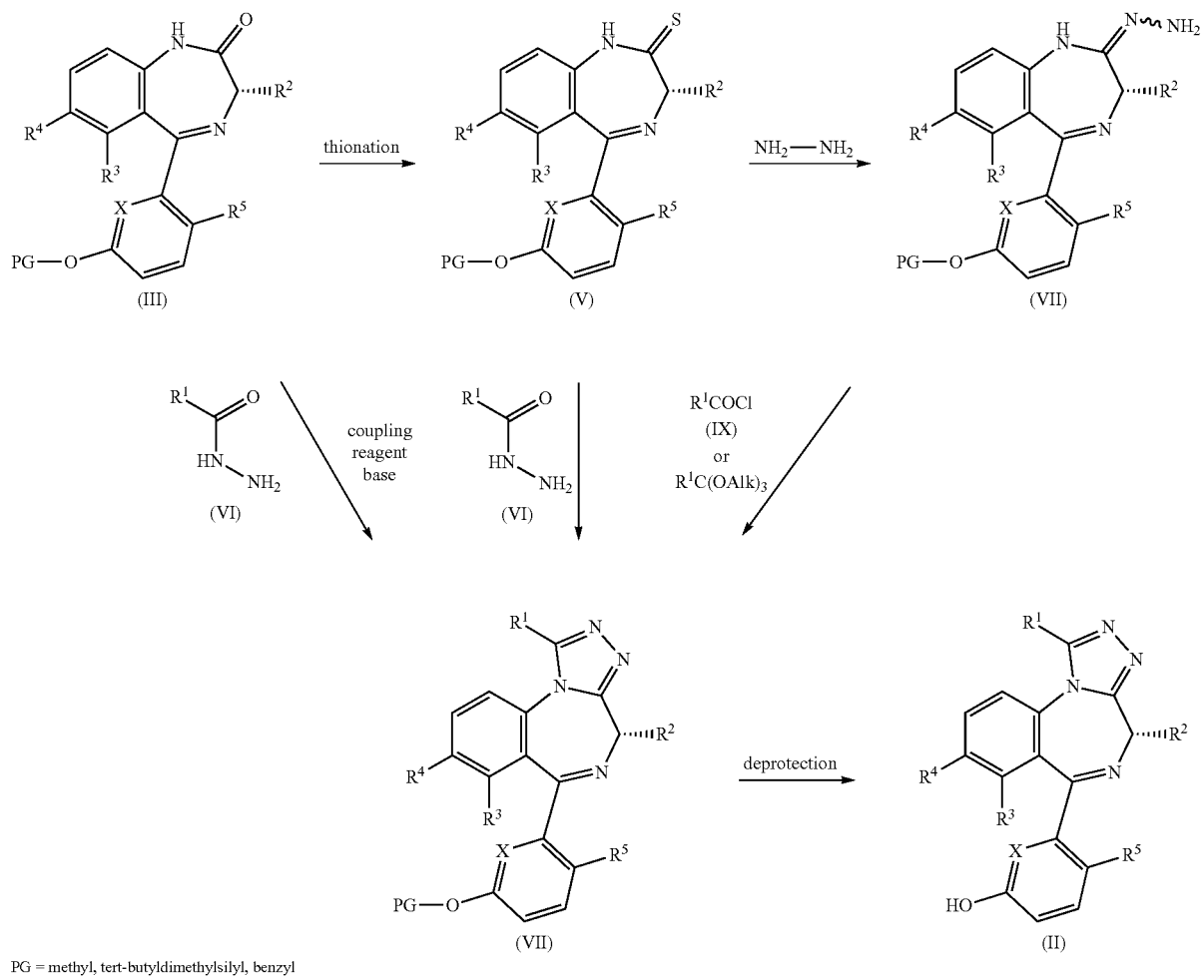

PG = methyl, tert-butyldimethylsilyl, benzyl

Following thionation reaction using Lawesson's reagent or $P_2S_5$, lactames (III) are converted to corresponding thiolactames (V). Their reaction with hydrazides (VI) via a Pellizzari type process yields 1,2,4-triazoles of general formula (VII). In alternative, 1,2,4-triazoles (VII) can be obtained by reaction between thiolactames (V) and hydrawith imidates (XI) provides 1,2,4-triazoles of formula (XII), which can be deprotected under acidic condition (such as hydrobromic acid, trifluoroacetic acid) or Lewis-acidic conditions (boron tribromide, aluminiumtrichloride, iodotrimethylsilane or the like) to yield final derivatives of formula (IIIc).

Scheme 3 synthesis of benzodiazepines of formula (IIc)
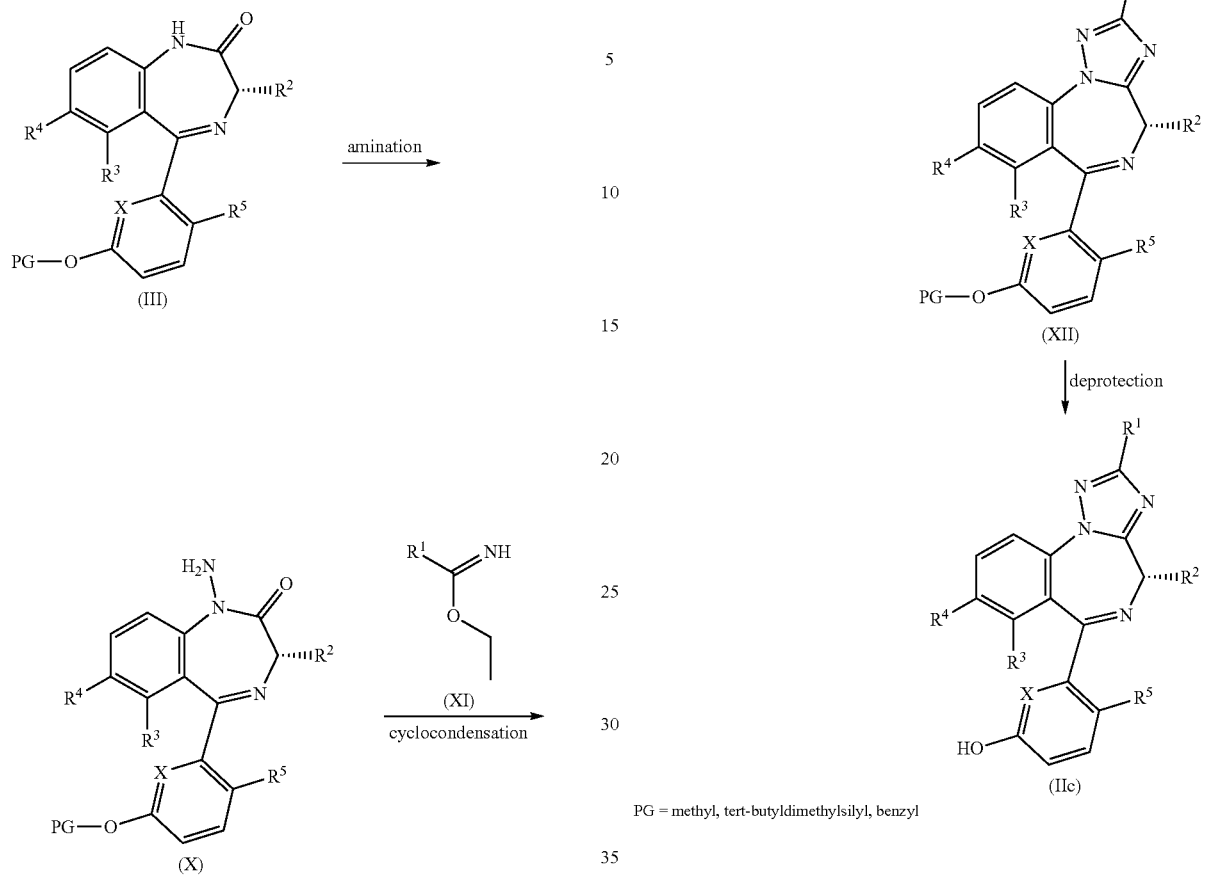
PG = methyl, tert-butyldimethylsilyl, benzyl
In certain embodiments of the invention compounds of formula (IId) can be prepared according to Scheme 4.
Scheme 4 synthesis of benzodiazepines of formula (IId)
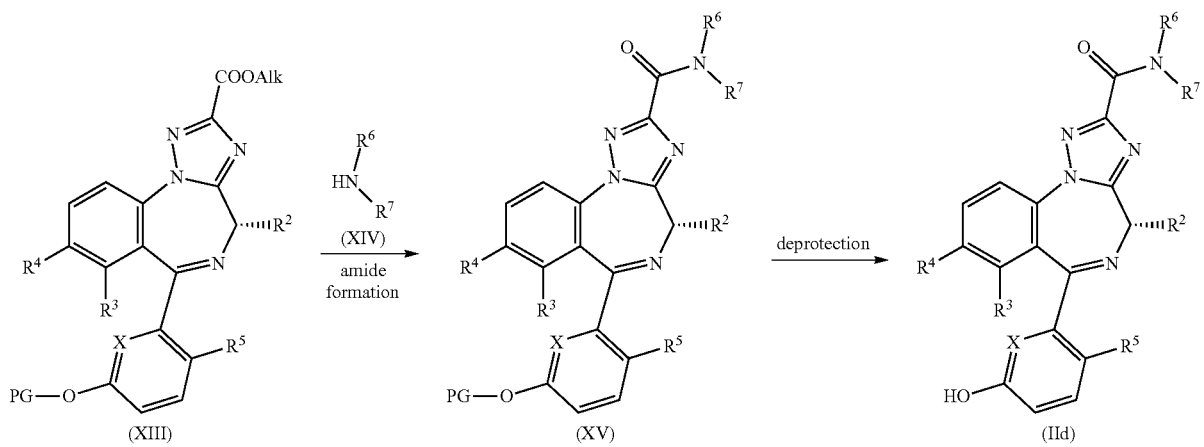

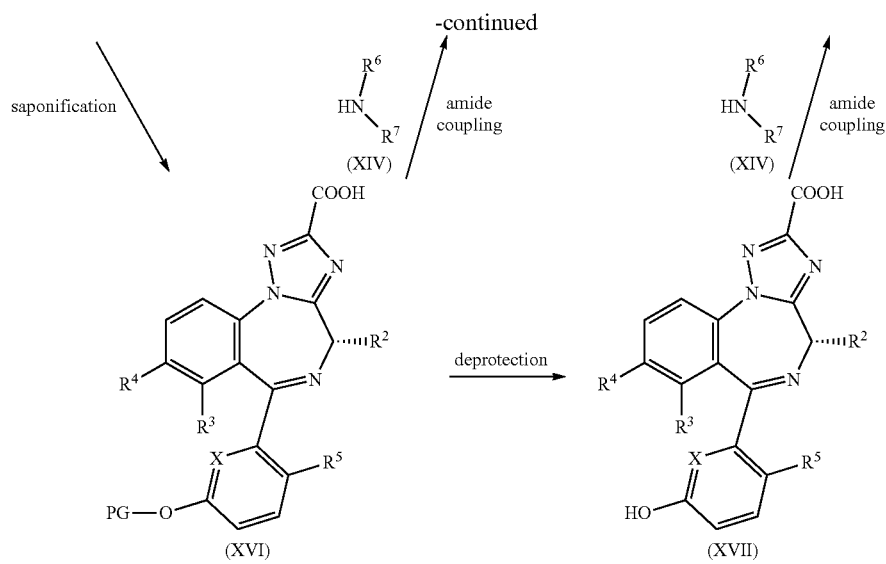

Alk = Me, Et
PG = methyl, tert-butyldimethylsilyl, benzyl

Esters (XIII), which are a selection of compounds (XII) defined by $R^1$=COOAlk (described in Scheme 3), are reacted with an amine (XIV) with or without addition of a suitable catalyst such as isopropylmagnesium chloride to form compounds of formula (XV). Alternatively, esters (XIII) can be saponified to the corresponding acids (XVI) under basic conditions, for instance by treatment with an aqueous or alcoholic solution of sodium hydroxide or lithium hydroxide. In turns, derivatives (XV) are obtained by standard amide coupling reaction between acids (XVI) and amines $HNR^4R^5$ (XIV). Further deprotection of compound (XV) under acidic condition (such as hydrobromic acid, trifluoroacetic acid) or Lewis-acidic conditions (boron tribromide, aluminiumtrichloride, iodotrimethylsilane or the like) yields compound (IId). Similarly, acids (XVI) can be deprotected as described above to form compound (XVII), then coupled with amines (XIV) in presence of a coupling reagent to form final derivatives of general formula (IId).

In further embodiments of the invention, imidazoles of formula (IIe) can be prepared as described below (Scheme 5).

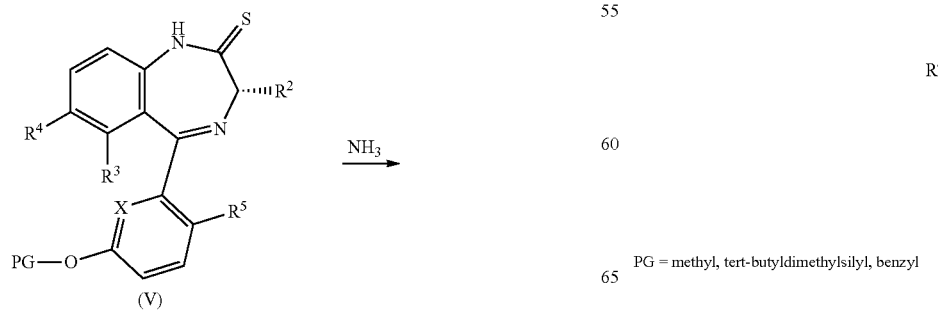

PG = methyl, tert-butyldimethylsilyl, benzyl

Thiolactams (V) are reacted with ammonia to form amidines of formula (XVIII). Following a reaction with propargylamine under acid catalysis, amidines (XVIII) can be converted to methyl imidazoles (XIX), which, in turns, can be deprotected under acidic condition (such as hydrobromic acid, trifluoroacetic acid) or Lewis-acidic conditions (boron tribromide, aluminiumtrichloride, iodotrimethylsilane or the like) to yield final derivatives of formula (IIe).

In further embodiments of the invention, imidazoles of formula (IIf) can be prepared as described in Scheme 6.

Lactams (III) are reacted with aminoalkohols (XX) upon activation with a suitable coupling reagent such as bis(2-oxo-3-oxazolidinyl)phosphinic chloride (BOP—Cl) to form intermediates (XXI) which can be cyclized under oxidative conditions to provide imidazoles of formula (XXII). Following a deprotection reaction under acidic condition (such as hydrobromic acid, trifluoroacetic acid) or Lewis-acidic conditions (boron tribromide, aluminiumtrichloride, iodotrimethylsilane or the like) final derivatives of formula (IIf) are obtained.

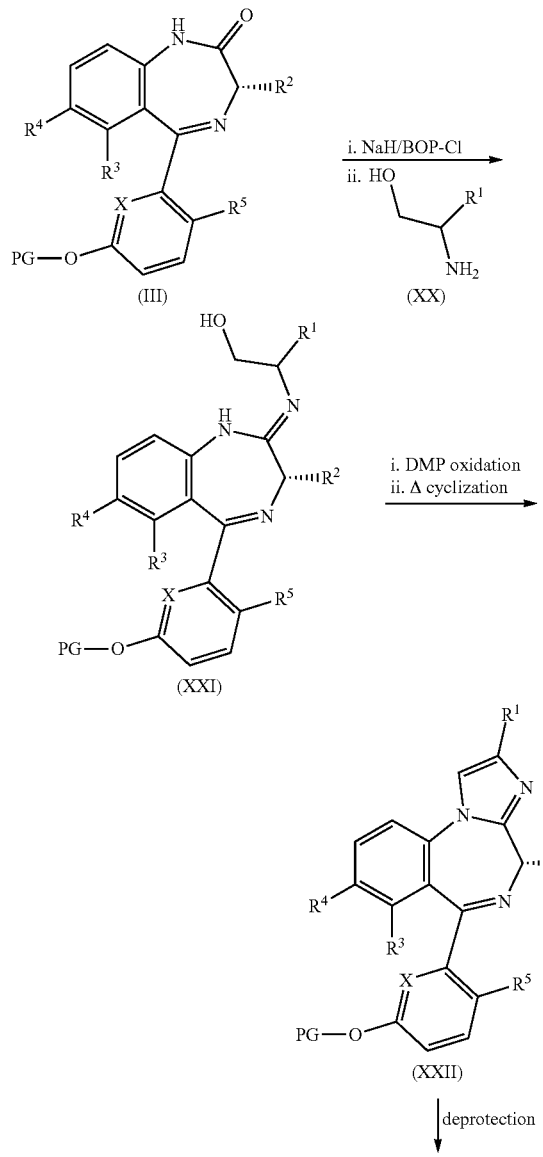

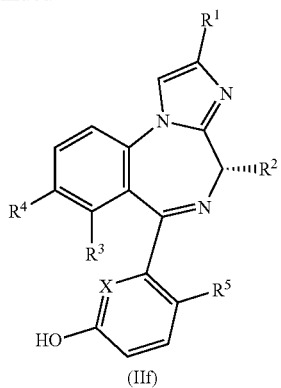

PG = methyl, tert-butyldimethylsilyl, benzyl

In a further embodiment of the invention, compounds of formula (IIg) can be prepared as depicted in Scheme 7.

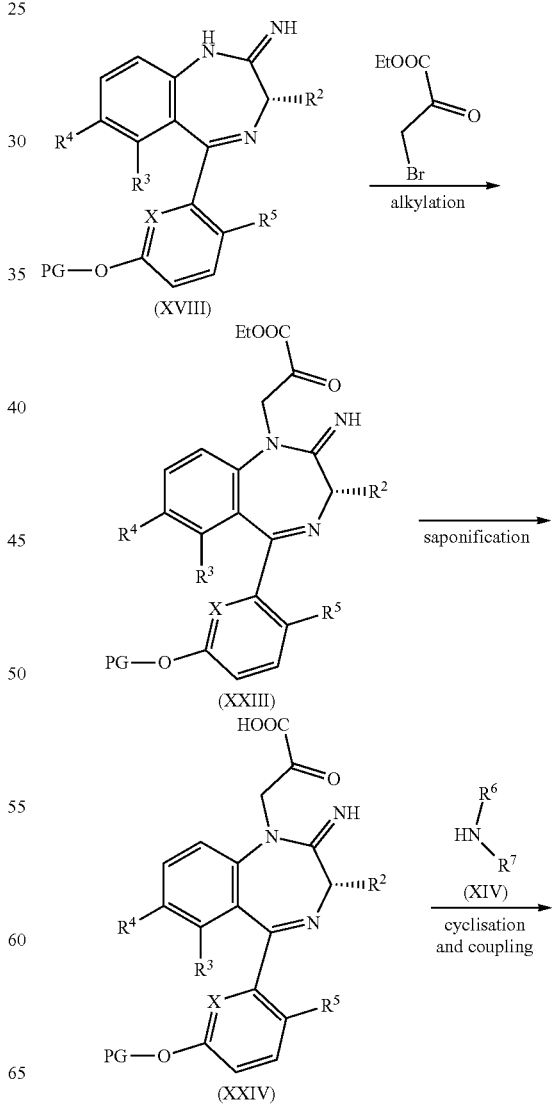

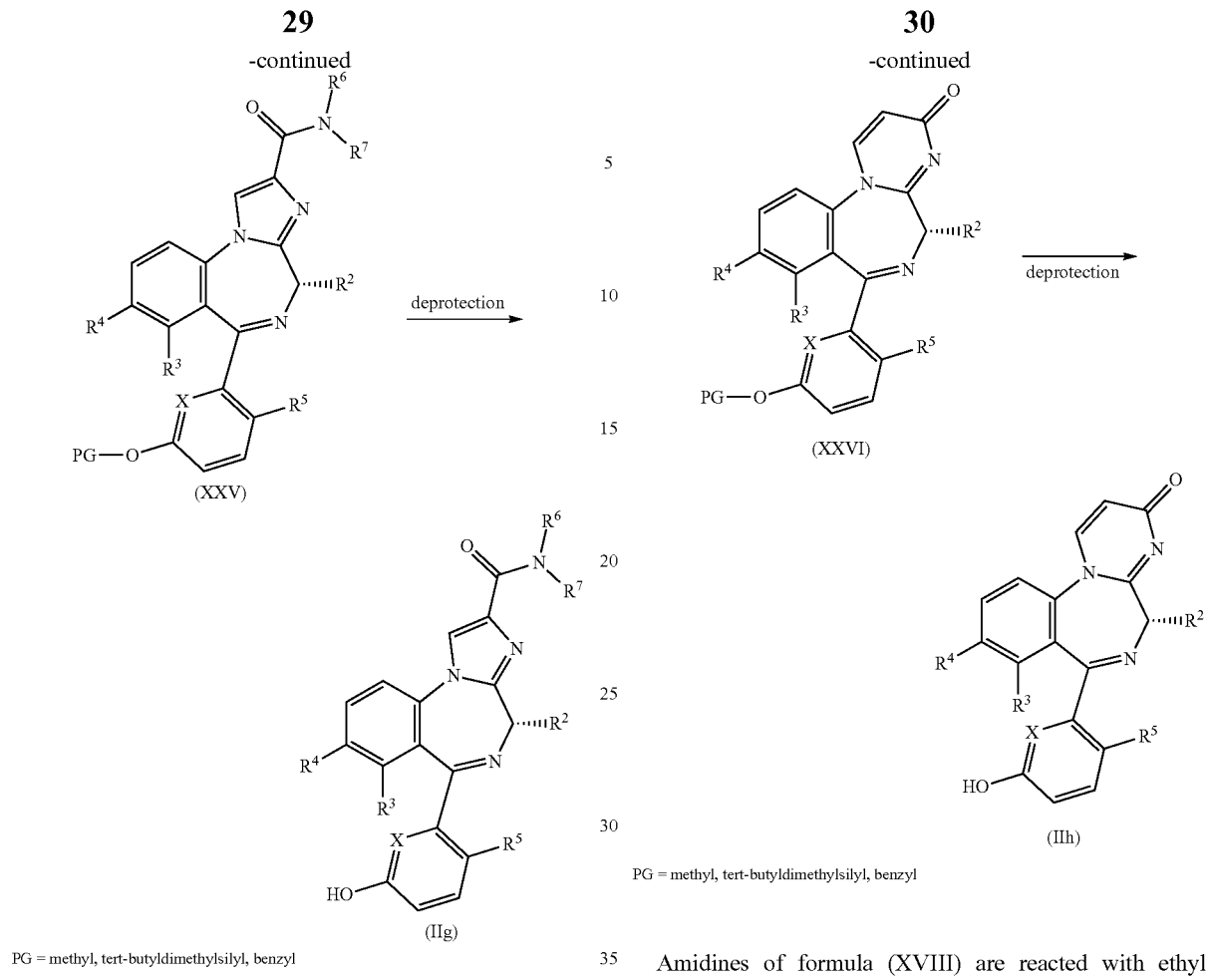

PG = methyl, tert-butyldimethylsilyl, benzyl

Amidines of formula (XVIII) are alkylated with ethyl bromopyruvate to form esters of formula (XXIII), which can be saponified under basic conditions to form acids (XXIV). Following an amide formation reaction with amines (XIV) and a suitable coupling reagent, acids (XXIV) can be converted to amides (XXV). Final deprotection reaction of compounds (XXV) under acidic condition (such as hydrobromic acid, trifluoroacetic acid) or Lewis-acidic conditions (boron tribromide, aluminiumtrichloride, iodotrimethylsilane or the like) yields final derivatives of general formula (IIg).

In further embodiments of the invention, compounds of formula (IIh) can be prepared as described in Scheme 8.

Amidines of formula (XVIII) are reacted with ethyl propiolate to form pyrimido[1,2-a][1,4]benzodiazepin-3-ones of formula (XXVI). Their final deprotection reaction under acidic conditions (such as hydrobromic acid, trifluoroacetic acid) or Lewis-acidic conditions (boron tribromide, aluminiumtrichloride, iodotrimethylsilane or the like) yields final derivatives of formula (IIh).

Furthermore, as detailed in Scheme 9, thiolactams (V) can be reacted with 2-aminocyclopentanol to form alcohols (XXVII) which can be oxidized with Dess-Martin-Periodinane to provide imidazoles (XXVIII). Their final deprotection under acidic condition (such as hydrobromic acid, trifluoroacetic acid) or Lewis-acidic conditions (boron tribromide, aluminiumtrichloride, iodotrimethylsilane or the like) yields final derivatives of general formula (IIi).

Scheme 8 synthesis of benzodiazepines of formula (IIh)

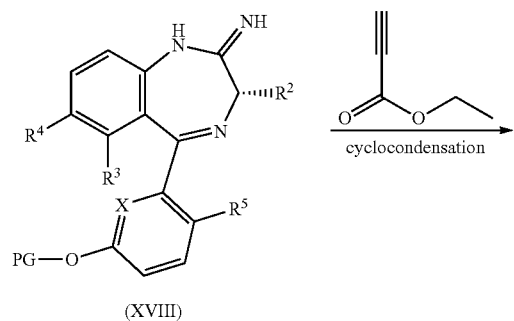

Scheme 9 synthesis of benzodiazepines of formula (IIi)

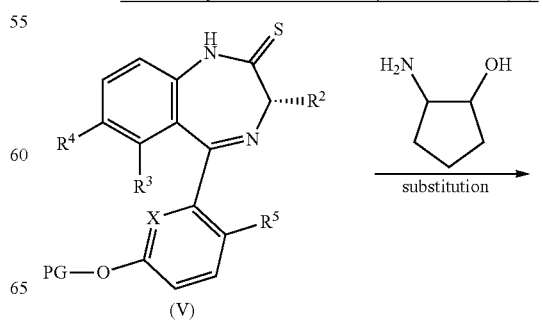

-continued
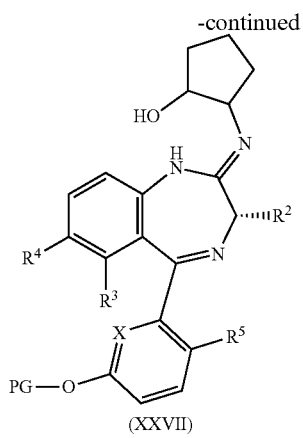
(XXVII)
i. DMP oxidation
ii. Δ cyclization
—— oxidative ring closure ——
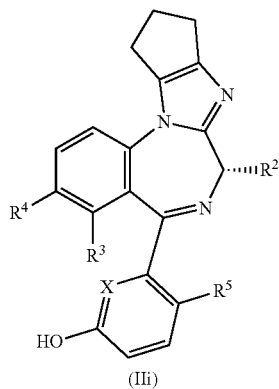
(IIi)
PG = methyl, tert-butyldimethylsilyl, benzyl
(XXVIII)
deprotection ↓
In further embodiments of the invention, compounds of formula (IIj) can be prepared as described in Scheme 10.
Scheme 10 synthesis of benzodiazepines of formula (IIj)
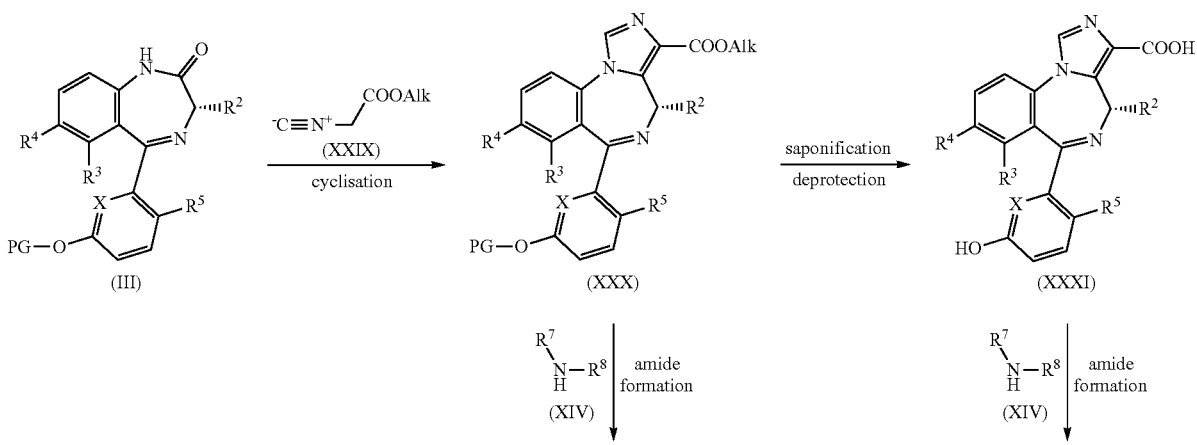

-continued

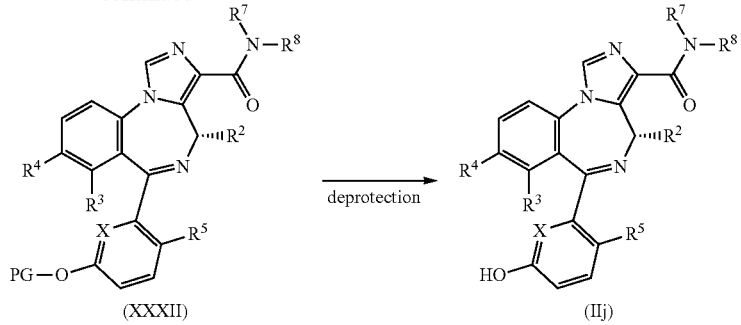

Alk = Me, Et
PG = methyl, tert-butyldimethylsilyl, benzyl
$R^7$ = H, $C_1$-$C_6$-alkyl or $C_3$-$C_{10}$-cycloalkyl
$R^8$ = H, $C_1$-$C_6$-alkyl or $C_3$-$C_{10}$-cycloalkyl Lactams (III) are reacted with alkyl isocyanoacetates (XXIX) to form imidazoles of formula (XXX). Saponification under standard conditions and deprotection under acidic condition (such as hydrobromic acid, trifluoroacetic acid) or Lewis-acidic conditions (boron tribromide, aluminiumtrichloride, iodotrimethylsilane or the like) yields carboxylic acids (XXXI). Their reaction with amines (XIV) under standard amide formation conditions yields final derivatives (IIj). Furthermore, imidazoles (XXX) can be reacted with amine (XIV) with or without addition of a suitable catalyst such as isopropylmagnesium chloride to form intermediates of formula (XXXII). Following a deprotection reaction under acidic condition (such as hydrobromic acid, trifluoroacetic acid) or Lewis-acidic conditions (boron tribromide, aluminiumtrichloride, iodotrimethylsilane) final derivatives of general formula (IIj) can be obtained.

The synthesis of the lactams (III) and their precursors is highlighted in the following schemes.

Lactams (III) can be synthesized according to Scheme 11. Commercially available 2-amino benzoic acids (XXXIII) can be heated in acetic anhydride to form benzoxazin-4-ones (XXXIV). Next, Grignard or organolithium reagents prepared by metalation reaction from corresponding aryl compound (XXXV) can be reacted with benzoxazin-4-ones (XXXIV) under controlled temperatures to provide ketones of formula (XXXVI). Following N-acetamide hydrolysis under acidic conditions, compounds of formula (XXXVI) are converted into aminobenzophenones of formula (XXXVII). Conveniently, at this junction, the halogen at $R^4$ can be installed by treatment with N-chlorosuccinimide (NCS), N-bromosuccinimide (NBS) or N-iodosuccinimide (NIS) to yield intermediates of formula (XXXVIII). Final thermal cyclisation reaction with ethyl 2-aminoacetate hydrochloride yields the desired O-protected lactam building block of formula (IIIa). Alternatively, amides (XL) can be obtained by coupling with N-Boc protected L-amino acids (XXXIX) upon exposure to phosphoryl chloride ($POCl_3$) in pyridine or reaction with a coupling reagent like HATU, HBTU or the like. Removal of N-Boc protecting group can be effected with mineral acids (e.g. HCl) or organic acids (e.g. trifluoroacetic acid) to yield amines of formula (XLI). Final intramolecular condensation reaction promoted by acidic media (e.g. silica in toluene or pivalic acid in ethanol) and heat (80-110° C.) provides desired lactam building block of formula (IIIb).

Scheme 11 synthesis of lactams (IIIa) and (IIIb)

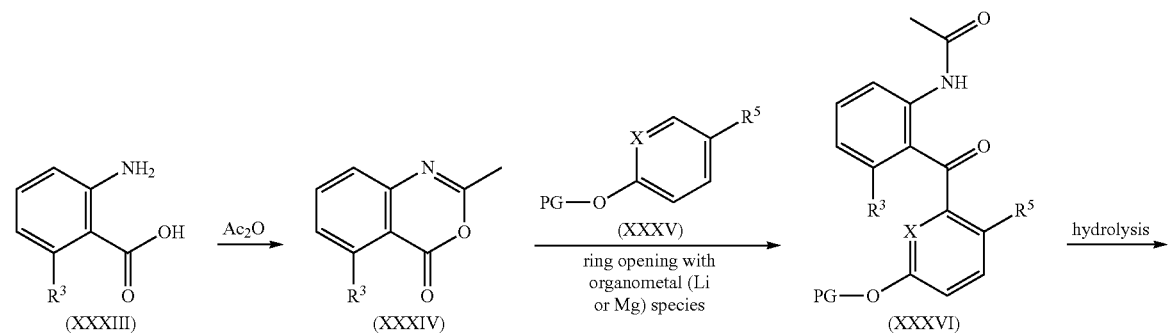

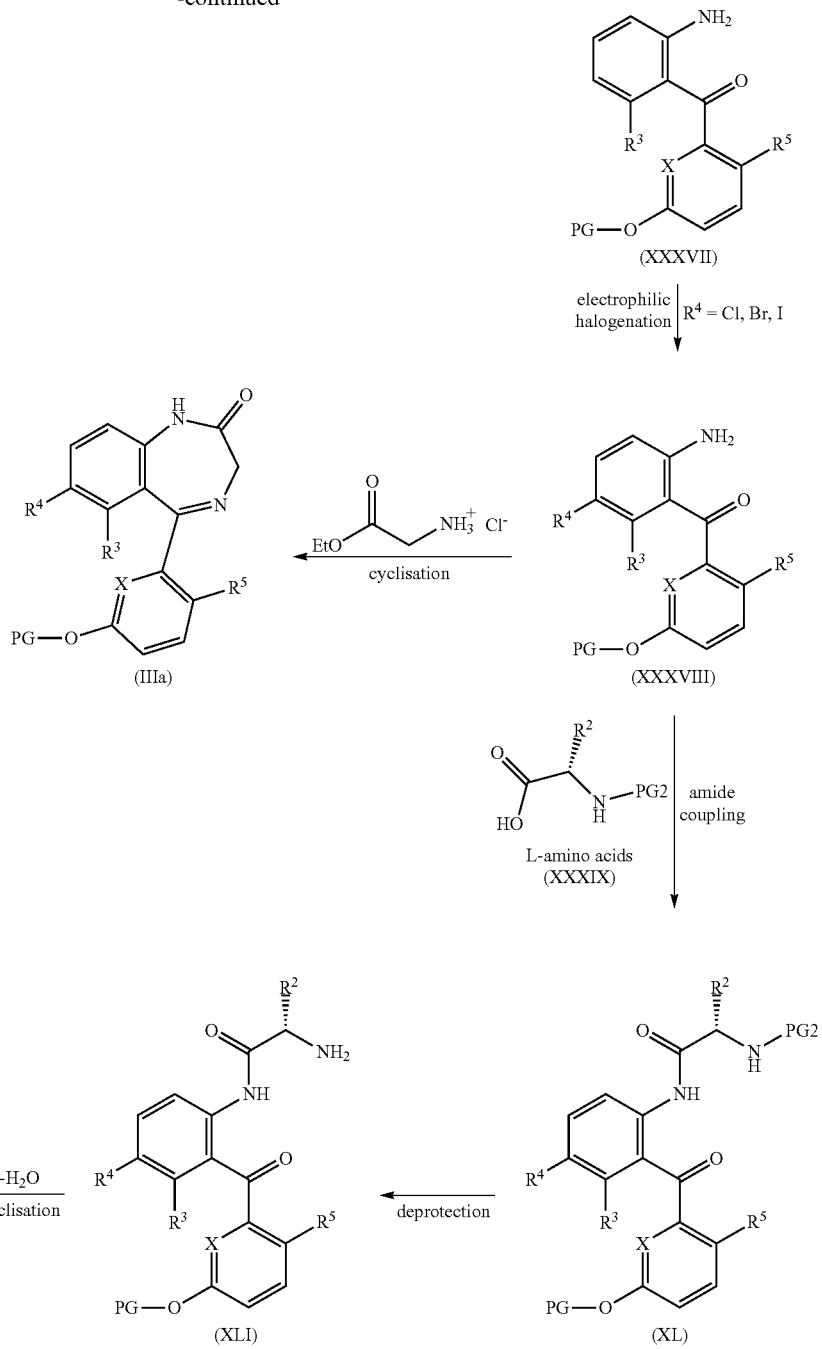

Alternatively, according to scheme 12, anilines (XLII) can be protected with a suitable protecting group such as tert-butyloxycarbonyl by treatment with di-tert-butyl dicarbonate in presence of a base (e.g. diisopropylethylamine) to provide compounds (XLIII). Regioselective metalation of compound (XLIII) at low temperature with n-BuLi, followed by 1,2-addition to aldehydes (XLIV) provides secondary alcohols of formula (XLV). Their subsequent oxidation to ketones (XLVI) using manganese dioxide, followed by a deprotection reaction using organic acids (e.g. trifluoroacetic acid in dichloromethane) provides aminobenzophenones of formula (XXXVIII).

Scheme 12 alternative synthesis of aminobenzophenone (XXXVIII)

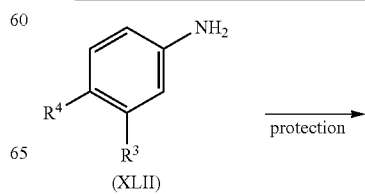

37

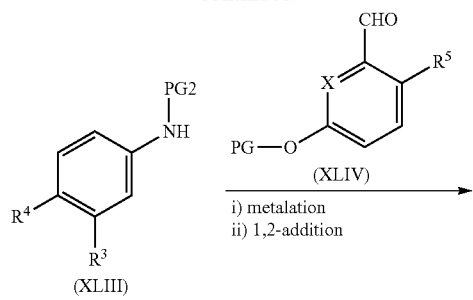

Scheme 13 synthesis of aminobenzophenones (XLVI)

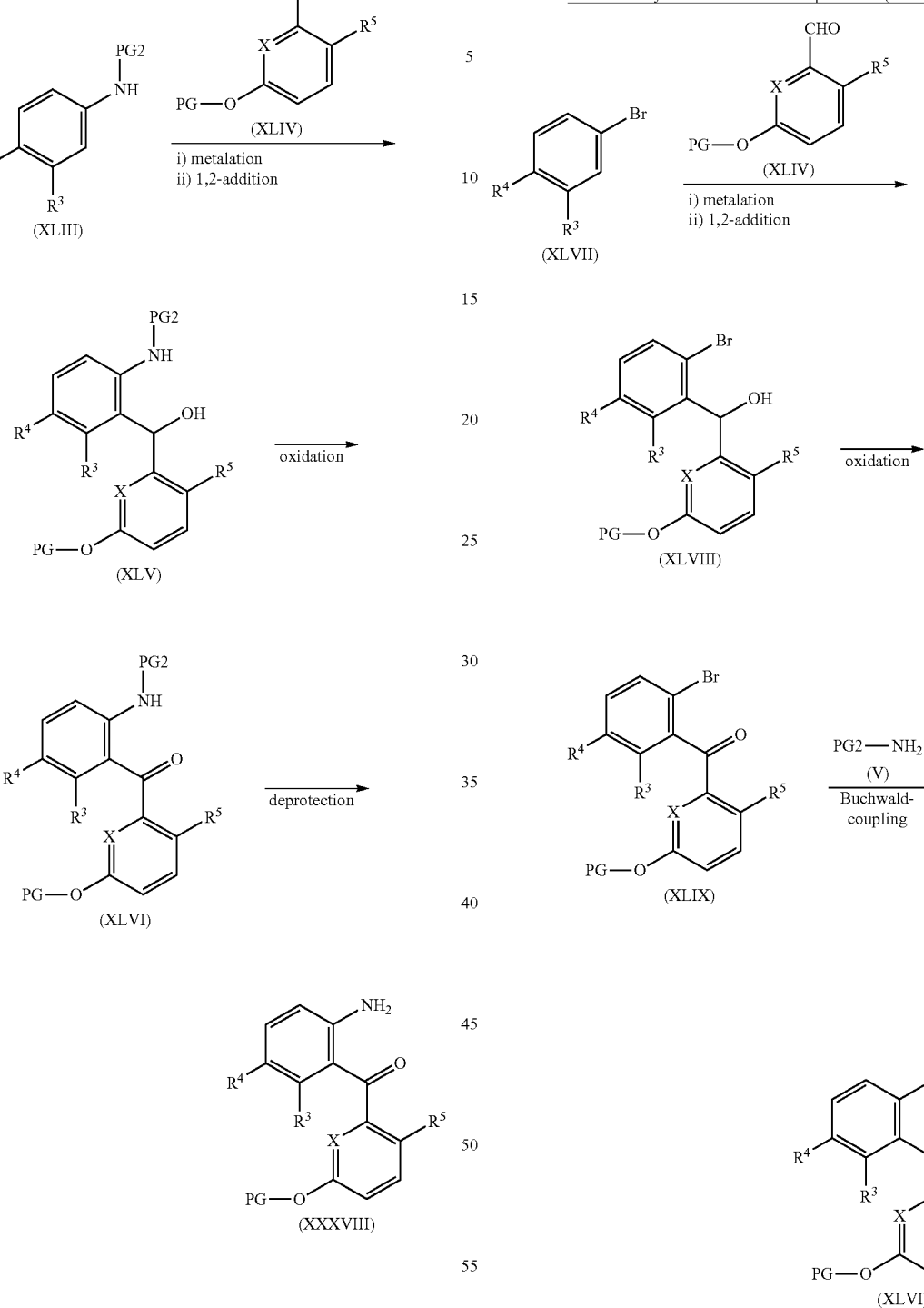

PG = methyl, tert-butyldimethylsilyl, benzyl
PG2 = Boc, Cbz

Furthermore, according to Scheme 13, regioselective metalation of aryl bromides (XLVII) at low temperature with n-BuLi, followed by 1,2-addition to aldehydes (XLIV) provides secondary alcohols of formula (XLVIII). Their subsequent oxidation to ketones (XLIX) followed by a palladium-catalysed coupling with carbamate (L) provided protected aminobenzophenones of formula (XLVI).

PG = methyl, tert-butyldimethylsilyl, benzyl
PG2 = Boc, Cbz

In addition, lactams of structure (III) can be synthesized by reacting iodo lactam (III) with a trifluoromethylating agent such as methyl 2,2-difluoro-2-(fluorosulfonyl)acetate using copper catalysis (see Scheme 14).

Scheme 14 synthesis of lactams (III)

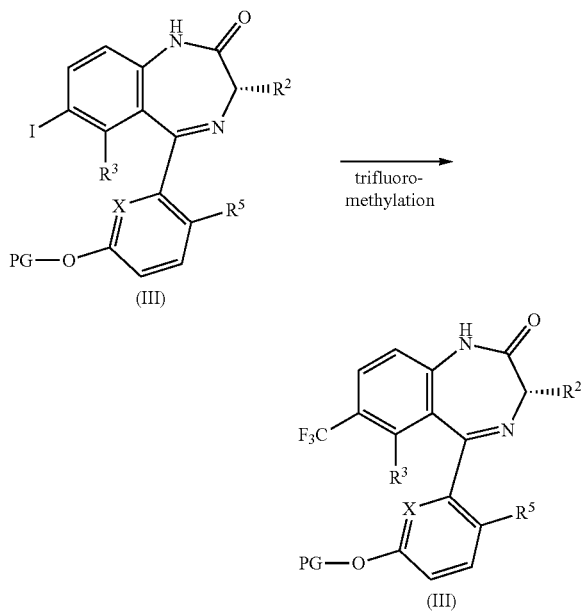

PG = methyl, tert-butyldimethylsilyl, benzyl

Notably, in the processes described in Schemes 1 to 14, racemization at the chiral center occurs to various extents (20-100%), depending on specific reaction conditions adopted. As a result, chiral purification (e.g. by HPLC or SFC) of final derivatives of formula (I) and (II), is required to obtain single enantiomers (enantiomeric excess (ee) above 97%)

Notably, partial racemisation of the chiral center may occur depending on specific reaction conditions adopted. As a result, chiral purification (e.g. by HPLC or SFC) of final derivatives of formula (I) and (II) is required to obtain final derivatives with enantiomeric excess (ee) above 97%.

In one aspect, the present invention provides a process of manufacturing the compounds of formula (I) and (II) described herein, wherein said process is as described in any one of Schemes 1 to 14 above.

In a further aspect, the present invention provides compounds of formula (I) and (II) as described herein, or a pharmaceutically acceptable salt thereof, when manufactured according to the processes disclosed herein.

Using the Compounds of the Invention

As explained in the background section and illustrated in the experimental section, the compounds of formula (I) or (II) and their pharmaceutically acceptable salts possess valuable pharmacological properties that make them useful for the treatment or prevention of diseases or conditions that are associated with the GABAA γ1 receptor.

In one aspect, the present invention provides a compound of formula (I) or (II) as described herein, or a pharmaceutically acceptable salt thereof, for use as therapeutically active substance.

In a further aspect, the present invention provides a method for treating or preventing acute neurological disorders, chronic neurological disorders and/or cognitive disorders in a subject, said method comprising administering an effective amount of a compound of formula (I) or (II) as described herein, or a pharmaceutically acceptable salt thereof, or a pharmaceutical composition described herein, to the subject.

In a further aspect, the present invention provides the use of a compound of formula (I) or (II) as described herein, or a pharmaceutically acceptable salt thereof, or a pharmaceutical composition described herein, in a method for treating or preventing acute neurological disorders, chronic neurological disorders and/or cognitive disorders in a subject.

In a further aspect, the present invention provides a compound of formula (I) or (II) as described herein, or a pharmaceutically acceptable salt thereof, or a pharmaceutical composition described herein, for use in a method for treating or preventing acute neurological disorders, chronic neurological disorders and/or cognitive disorders in a subject.

In a further aspect, the present invention provides the use of a compound of formula (I) or (II) as described herein, or a pharmaceutically acceptable salt thereof, for the manufacture of a medicament for the treatment of prevention of acute neurological disorders, chronic neurological disorders and/or cognitive disorders.

In one embodiment, said acute neurological disorders, chronic neurological disorders and/or cognitive disorders are selected from autism spectrum disorders (ASD), Angelman syndrome, age-related cognitive decline, Rett syndrome, Prader-Willi syndrome, amyotrophic lateral sclerosis (ALS), fragile-X disorder, negative and/or cognitive symptoms associated with schizophrenia, tardive dyskinesia, anxiety, social anxiety disorder (social phobia), panic disorder, agoraphobia, generalized anxiety disorder, disruptive, impulse-control and conduct disorders, Tourette's syndrome (TS), obsessive-compulsive disorder (OCD), acute stress disorder, post-traumatic stress disorder (PTSD), attention deficit hyperactivity disorder (ADHD), sleep disorders, Parkinson's disease (PD), Huntington's chorea, Alzheimer's disease (AD), mild cognitive impairment (MCI), dementia, behavioral and psychological symptoms (BPS) in neurodegenerative conditions, multi-infarct dementia, agitation, psychosis, substance-induced psychotic disorder, aggression, eating disorders, depression, chronic apathy, anhedonia, chronic fatigue, seasonal affective disorder, postpartum depression, drowsiness, sexual dysfunction, bipolar disorders, epilepsy and pain.

In one embodiment, said acute neurological disorders, chronic neurological disorders and/or cognitive disorders are selected from Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), and fragile-X disorder.

In a preferred embodiment, said acute neurological disorders, chronic neurological disorders and/or cognitive disorders are selected from autism spectrum disorder (ASD), Angelman syndrome, Alzheimer's disease, negative and/or cognitive symptoms associated with schizophrenia and post-traumatic stress disorder (PTSD).

In a preferred embodiment, said acute neurological disorders, chronic neurological disorders and/or cognitive disorders are selected from autism spectrum disorder (ASD), Rett syndrome, Angelman syndrome, post-traumatic stress disorder and fragile-X disorder.

In a preferred embodiment, said acute neurological disorders, chronic neurological disorders and/or cognitive disorders are selected from autism spectrum disorder (ASD), Rett syndrome, post-traumatic stress disorder and fragile-X disorder.

In a preferred embodiment, said acute neurological disorders, chronic neurological disorders and/or cognitive disorders are selected from autism spectrum disorder (ASD), and Angelman syndrome.

In a particularly preferred embodiment, said acute neurological disorders, chronic neurological disorders and/or cognitive disorders are autism spectrum disorder (ASD).

In a particularly preferred embodiment, said acute neurological disorders, chronic neurological disorders and/or cognitive disorders are Angelman syndrome.

In a further particularly preferred embodiment, said acute neurological disorders, chronic neurological disorders and/or cognitive disorders are autism spectrum disorder (ASD), targeting core symptoms and associated comorbidities, such as anxiety and irritability, social anxiety disorder (social phobia) and generalized anxiety disorder.

In a further particularly preferred embodiment, said acute neurological disorders, chronic neurological disorders and/or cognitive disorders are selected from social anxiety disorder (social phobia) and generalized anxiety disorder.

Pharmaceutical Compositions and Administration

In one aspect, the present invention provides pharmaceutical compositions comprising compounds of formula (I) or (II) or their pharmaceutically acceptable salts as defined herein and one or more pharmaceutically acceptable excipients. Exemplary pharmaceutical compositions are described in the Example section below.

In a further aspect, the present invention relates to pharmaceutical compositions comprising compounds of formula (I) or (II) or their pharmaceutically acceptable salts as defined above and one or more pharmaceutically acceptable excipients for the treatment or prevention of acute neurological disorders, chronic neurological disorders and/or cognitive disorders.

The compounds of formula (I) or (II) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions or infusion solutions).

The compounds of formula (I) or (II) and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc. can be used, for example, as such excipients for tablets, dragées and hard gelatin capsules.

Suitable excipients for soft gelatin capsules are, for example, vegetable oils, waxes, fats, semi-solid substances and liquid polyols, etc.

Suitable excipients for the production of solutions and syrups are, for example, water, polyols, saccharose, invert sugar, glucose, etc.

Suitable excipients for injection solutions are, for example, water, alcohols, polyols, glycerol, vegetable oils, etc.

Suitable excipients for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

Building Block Syntheses

The building blocks can be produced according to the following synthetic procedures.

Building Block A 6,7-dichloro-5-(2-fluoro-5-methoxy-phenyl)-1,3-dihydro-1,4-benzodiazepin-2-one

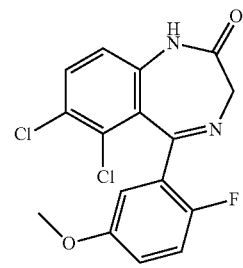 [SMILES: COc1ccc(F)c(C2=NCC(=O)Nc3ccc(Cl)c(Cl)c32)c1]

a) 5-chloro-2-methyl-3,1-benzoxazin-4-one

A solution of 2-amino-6-chlorobenzoic acid (15.0 g, 87.4 mmol) in acetic anhydride (200 mL) was stirred at 140° C. for 2 h. The reaction solution was concentrated in vacuo. The residue was suspended in acetonitrile, the solid was filtered and the filter cake was dried in in vacuo to afford the title compound (11.3 g, 66%) as a white solid. $^1$H NMR (400 MHz, CDCl$_3$) δ ppm 2.47 (3H, s) 7.47 (1H, dd, J=8.1, 0.9 Hz) 7.53 (1H, dd, J=7.9, 1.0 Hz) 7.67 (1H, dd, J=8.1, 8.0 Hz).

b) N-[3-chloro-2-(2-fluoro-5-methoxy-benzoyl)phenyl]acetamide

To a solution of 2-bromo-1-fluoro-4-methoxybenzene (5.45 g, 26.6 mmol) in THF (200 mL) was added n-butyllithium (2.5 M in hexane, 12.8 mL, 31.9 mmol) at −78° C. After stirring for 1 h, 5-chloro-2-methyl-3,1-benzoxazin-4-one (5.20 g, 26.6 mmol) was added to the mixture and stirring was continued for another 1 h at −78° C. The mixture was quenched with aqueous saturated NH$_4$Cl and extracted with ethyl acetate. The organic layer was dried (Na$_2$SO$_4$), filtered and concentrated in vacuo. The residue was purified by preparative HPLC (Phenomenex luna C18, 10 µm, 250× 50 mm, 0.05% HCl in water/acetonitrile) to afford the title compound (3.63 g, 42%) as a light yellow solid. MS: 322.1 ([{$^{35}$Cl}M+H]$^+$), 324.1 ([{$^{37}$Cl}M+H]$^+$), ESI pos.

c) (2-amino-6-chloro-phenyl)-(2-fluoro-5-methoxy-phenyl)methanone

To a solution of N-[3-chloro-2-(2-fluoro-5-methoxy-benzoyl)phenyl]acetamide (4.00 g, 12.4 mmol) in ethanol (50 mL) was added aqueous HCl (37%, 53.3 mL, 640 mmol). The mixture was stirred at 100° C. for 2 h and then concentrated in vacuo. The residue was dissolved in DCM and washed with saturated aqueous NaHCO$_3$ and water successively. The organic layer was dried (Na$_2$SO$_4$), filtered and concentrated in vacuo to afford the title compound (2.87 g, 83%) as an off-white solid. MS: 280.0 ([{$^{35}$Cl}M+H]$^+$), 282.0 ([{$^{37}$Cl}M+H]$^+$), ESI pos.

d) (6-amino-2,3-dichloro-phenyl)-(2-fluoro-5-methoxy-phenyl)methanone

A solution of (2-amino-6-chloro-phenyl)-(2-fluoro-5-methoxy-phenyl)methanone (1.00 g, 3.58 mmol) and N-chlorosuccinimide (430 mg, 3.22 mmol) in DMF (20 mL) was stirred at 0° C. for 2 h. The mixture was quenched with water and extracted with DCM. The organic layer was dried (Na$_2$SO$_4$), filtered and concentrated in vacuo. The residue was purified by preparative HPLC (Phenomenex Synergi C18, 10 µm, 150×25 mm, 0.1% trifluoroacetic acid in water/acetonitrile) to afford the title compound (367 mg, 33%) as a light yellow solid. MS: 313.9 ([{$^{35}$Cl, $^{35}$Cl}M+H]$^+$), 315.9 ([{$^{35}$Cl, $^{37}$Cl}M+H]$^+$), ESI pos.

e) 6,7-dichloro-5-(2-fluoro-5-methoxy-phenyl)-1,3-dihydro-1,4-benzodiazepin-2-one A solution of glycine ethyl ester hydrochloride (2.89 g, 20.7 mmol) and (6-amino-2,3-dichloro-phenyl)-(2-fluoro-5-methoxy-phenyl)methanone (650 mg, 2.07 mmol) in pyridine (30 mL) was stirred at 100° C. for 16 h. The mixture was concentrated in vacuo. The residue was purified by preparative HPLC (Phenomenex Synergi C18, 10 µm, 150× 25 mm, 0.1% trifluoroacetic acid in water/acetonitrile) to afford the title compound (280 mg, 38%) as a yellow solid. MS: 353.0 ([{$^{35}$Cl, $^{35}$Cl}M+H]$^+$), 355.0 ([{$^{35}$Cl, $^{37}$Cl}M+H]$^+$), ESI pos.

Building Block B

6-chloro-5-(2-fluoro-5-methoxy-phenyl)-7-methyl-1,3-dihydro-1,4-benzodiazepin-2-one

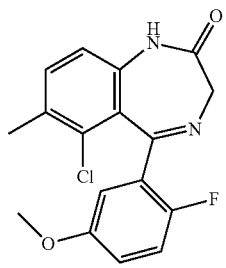 [SMILES: COc1ccc(F)c(C2=NCC(=O)Nc3ccc(C)c(Cl)c32)c1]

a) (6-amino-3-bromo-2-chloro-phenyl)-(2-fluoro-5-methoxy-phenyl)methanone

In analogy to experiment of Building block A d, (2-amino-6-chloro-phenyl)-(2-fluoro-5-methoxy-phenyl)methanone (Building block A c) using N-bromosuccinimide instead of N-chlorosuccinimide was converted into the title compound (1.63 g, 64%) which was obtained as a light yellow solid. MS: 357.9 ([{$^{79}$Br, $^{35}$Cl}M+H]$^+$), 359.9 ([{$^{81}$Br, $^{35}$Cl or $^{79}$Br, $^{37}$Cl}M+H]$^+$), ESI pos.

b) 7-bromo-6-chloro-5-(2-fluoro-5-methoxy-phenyl)-1,3-dihydro-1,4-benzodiazepin-2-one In analogy to experiment of Building block A e, (6-amino-3-bromo-2-chloro-phenyl)-(2-fluoro-5-methoxy-phenyl)methanone was converted into the title compound (1.63 g, 64%) as a light yellow solid (860 mg, 38%) which was obtained as a light yellow solid. MS: 396.9 ([{$^{79}$Br, $^{35}$Cl}M+H]$^+$), 398.9 ([{$^{81}$Br, $^{35}$Cl or $^{79}$Br, $^{37}$Cl}M+H]$^+$), ESI pos.

c) 6-chloro-5-(2-fluoro-5-methoxy-phenyl)-7-methyl-1,3-dihydro-1,4-benzodiazepin-2-one A solution of 7-bromo-6-chloro-5-(2-fluoro-5-methoxy-phenyl)-1,3-dihydro-1,4-benzodiazepin-2-one (600 mg, 1.51 mmol), methylboronic acid (117 mg, 1.96 mmol), potassium phosphate (641 mg, 3.02 mmol) and [1,1'-bis(diphenylphosphino)ferrocene]dichloropalladium(II) (1.10 g, 1.51 mmol) in DMF (12 mL) was stirred at 80° C. for 6 h under nitrogen. The reaction was diluted with methanol, filtered through a plug of Celite and the filtrate was concentrated in vacuo. The residue was treated with water and extracted with ethyl acetate. The organic layer was dried (Na$_2$SO$_4$), filtered and concentrated in vacuo. The residue was purified by preparative HPLC (Phenomenex Synergi C18, 10 µm, 150×25 mm, 0.1% trifluoroacetic acid in water/acetonitrile) to afford the title compound (230 mg, 45%) as a light brown solid. MS: 333.1 ([{$^{79}$Br, $^{35}$Cl}M+H]$^+$), 335.1 ([{$^{81}$Br, $^{35}$Cl or $^{79}$Br, $^{37}$Cl}M+H]$^+$), ESI pos.

Building Block C 6,7-dichloro-5-(2-fluoro-5-methoxy-phenyl)-3-methyl-1,3-dihydro-1,4-benzodiazepin-2-one

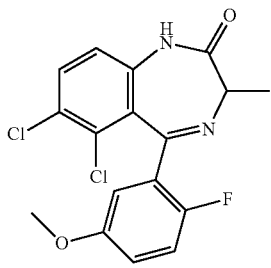 [SMILES: COc1ccc(F)c(C2=NC(C)C(=O)Nc3ccc(Cl)c(Cl)c32)c1]

a) tert-butyl N-[2-[3,4-dichloro-2-(2-fluoro-5-methoxy-benzoyl)anilino]-1-methyl-2-oxo-ethyl]carbamate To a solution of (6-amino-2,3-dichloro-phenyl)-(2-fluoro-5-methoxy-phenyl)methanone (Building block A d, 2.00 g, 6.37 mmol) in pyridine (50 mL) was added Boc-DL-Ala-OH (1.81 g, 9.55 mmol). The reaction mixture was cooled to 0° C., then phosphoryl trichloride (1.56 g, 10.2 mmol) was added and the mixture was stirred at 0° C. for 1 h. The mixture was quenched by the addition of saturated aqueous NaHCO$_3$ and extracted with DCM. The organic layer was washed with brine and concentrated in vacuo. The residue was purified by flash column chromatography (silica, petroleum ether/ethyl acetate 10:1 to 1:1) to afford the title compound (2.5 g, 81%) as a yellow oil. MS: 385.1 ([{$^{35}$Cl, $^{35}$Cl}M+H-Boc]), 387.1 ([{$^{35}$Cl, $^{37}$Cl}M+H-Boc]$^+$), ESI pos.

b) 2-amino-N-[3,4-dichloro-2-(2-fluoro-5-methoxy-benzoyl)phenyl]propanamide

To a solution of tert-butyl N-[2-[3,4-dichloro-2-(2-fluoro-5-methoxy-benzoyl)anilino]-1-methyl-2-oxo-ethyl]carbamate (2.00 g, 4.12 mmol) in ethyl acetate (10 mL) was added HCl (4 M in ethyl acetate, 10 mL, 40 mmol). The mixture was stirred at 0° C. for 3 h. Water was added, the pH was adjusted to 9 by progressively adding solid NaHCO$_3$ and the product was extracted with ethyl acetate. The organic layer was washed with brine and concentrated in vacuo to afford the title compound (1.5 g, 94%) as a yellow oil. MS: 385.1 ([{$^{35}$Cl, $^{35}$Cl}M+H]$^+$), 387.1 ([{$^{35}$Cl, $^{37}$Cl}M+H]$^+$), ESI pos.

c) 6,7-dichloro-5-(2-fluoro-5-methoxy-phenyl)-3-methyl-1,3-dihydro-1,4-benzodiazepin-2-one To a solution of 2-amino-N-[3,4-dichloro-2-(2-fluoro-5-methoxy-benzoyl)phenyl]propanamide (1.67 g, 4.34 mmol) in toluene (100 mL) was added silica gel (8.00 g, 133 mmol) and the mixture was stirred at 90° C. for 15 h. The mixture was cooled and concentrated in vacuo. The residue was purified (together with another batch, 0.52 mmol scale) by flash column chromatography (silica, petroleum ether/ethyl acetate 10:1 to 0:1) to afford the title compound (1.5 g, 84%) as a yellow solid. MS: 367.11 ([{$^{35}$Cl, $^{35}$Cl}M+H]$^+$), 369.1 ([{$^{35}$Cl, $^{37}$Cl}M+H]$^+$), ESI pos.

Building Block D 6-chloro-5-(2-fluoro-5-methoxy-phenyl)-7-(trifluoromethyl)-1,3-dihydro-1,4-benzodiazepin-2-one

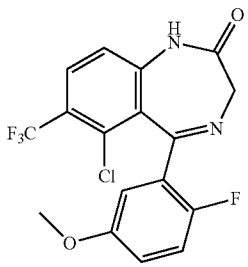 [SMILES: COc1ccc(F)c(C2=NCC(=O)Nc3ccc(C(F)(F)F)c(Cl)c32)c1]

a) (6-amino-2-chloro-3-iodo-phenyl)-(2-fluoro-5-methoxy-phenyl)methanone

In analogy to experiment of Building block A d, (2-amino-6-chloro-phenyl)-(2-fluoro-5-methoxy-phenyl)methanone (Building block A c) using N-iodosuccinimide instead of N-chlorosuccinimide was converted into the title compound (1.20 g, 59%) which was obtained as a yellow solid. MS: 405.9 ([{$^{35}$Cl}M+H]$^+$), 407.9 ([{$^{37}$Cl}M+H]$^+$), ESI pos.

b) 6-chloro-5-(2-fluoro-5-methoxy-phenyl)-7-iodo-1,3-dihydro-1,4-benzodiazepin-2-one In analogy to experiment of Building block A e, (6-amino-2-chloro-3-iodo-phenyl)-(2-fluoro-5-methoxy-phenyl)methanone was converted into the title compound (2.78 g, 40%) which was obtained as a yellow solid. MS: 445.1 ([{$^{35}$Cl}M+H]$^+$), 447.1 ([{$^{37}$Cl}M+H]$^+$), ESI pos.

c) 6-chloro-5-(2-fluoro-5-methoxy-phenyl)-7-(trifluoromethyl)-1,3-dihydro-1,4-benzodiazepin-2-one A mixture of 6-chloro-5-(2-fluoro-5-methoxy-phenyl)-7-iodo-1,3-dihydro-1,4-benzodiazepin-2-one (1.00 g, 1.98 mmol, 88% purity), methyl 2,2-difluoro-2-(fluorosulfonyl)acetate (1.14 g, 5.95 mmol) and copper iodide (756 mg, 3.97 mmol) in DMF (20 mL) containing HMPA (10.0 mL, 1.98 mmol) was stirred under nitrogen at 70° C. for 16 h. The mixture was cooled and poured into water/ethyl acetate 1:1. The suspension was filtered and the aqueous layer was extracted with ethyl acetate. The organic layer was washed with brine, dried (Na$_2$SO$_4$), filtered and concentrated in vacuo. The residue was purified by flash column chromatography (silica, 0-50% ethyl acetate in petroleum ether) to afford the title compound (450 mg, 59%) as a brown oil. MS: 387.0 ([{$^{35}$Cl}M+H]$^+$), 389.0 ([{$^{37}$Cl}M+H]$^+$), ESI pos.

Building Block E

6,7-dichloro-5-(2,6-difluoro-3-methoxy-phenyl)-1,3-dihydro-1,4-benzodiazepin-2-one

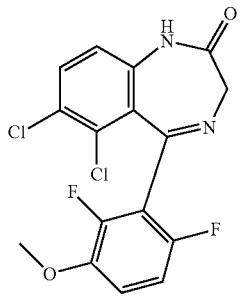 [SMILES: COc1ccc(F)c(C2=NCC(=O)Nc3ccc(Cl)c(Cl)c32)c1F]

a) tert-butyl N-[3,4-dichloro-2-[(2,6-difluoro-3-methoxy-phenyl)-hydroxy-methyl]phenyl]carbamate A solution of tert-buthyllithium (1 M in THF, 18.0 mL, 18 mmol) was added dropwise to a solution of tert-butyl N-(3,4-dichlorophenyl)carbamate (4.00 g, 15.3 mmol) in THF (100 mL) at −78° C. After stirring for 0.5 h, 2,6-difluoro-3-methoxy-benzaldehyde (3.15 g, 18.3 mmol) was added to the mixture at −78° C. and stirring was continued for an additional 0.5 h. The mixture was quenched with saturated aqueous NH$_4$Cl, warmed to room temperature and extracted with ethyl acetate. The organic layer was dried (Na$_2$SO$_4$), filtered and concentrated in vacuo. The residue was suspended in petroleum ether/DCM 50:1, the solid was filtered and dried in vacuo to afford the title compound (2.10 g, 32%) as a white solid. MS: 456.0 ([{$^{35}$Cl, $^{35}$Cl}M+Na]$^+$), 458.0 ([{$^{35}$Cl, $^{37}$Cl}M+Na]$^+$), ESI pos.

b) tert-butyl N-[3,4-dichloro-2-(2,6-difluoro-3-methoxy-benzoyl)phenyl]carbamate To a solution of potassium bromide (80 mg, 0.67 mmol), NaHCO$_3$ (145 mg, 1.73 mmol), TEMPO (73 mg, 0.47 mmol), aqueous sodium hypochlorite (0.4 M, 13 mL, 5.2 mmol) in DCM (130 mL) and water (65 mL) was added tert-butyl N-[3,4-dichloro-2-[(2,6-difluoro-3-methoxy-phenyl)-hydroxy-methyl]phenyl]carbamate (1.80 g, 4.14 mmol) and the reaction mixture was stirred at 25° C. for 16 h. The reaction was diluted with DCM and the organic layer was dried (Na$_2$SO$_4$), filtered and concentrated in vacuo to afford the title compound (1.50 g, 84%) as a light yellow oil. MS: 331.9 ([{$^{35}$Cl, $^{35}$Cl}M+H-Boc]), 333.9 ([{$^{35}$Cl, $^{37}$Cl}M+H-Boc]), ESI pos.

c) (6-amino-2,3-dichloro-phenyl)-(2,6-difluoro-3-methoxy-phenyl)methanone hydrochloride To a solution of tert-butyl N-[3,4-dichloro-2-(2,6-difluoro-3-methoxy-benzoyl)phenyl]carbamate (1.50 g, 3.47 mmol) in ethyl acetate (20 mL) was added HCl (4 M in ethyl acetate, 7.5 mL, 30 mmol). The mixture was stirred at 20° C. for 3 h. The precipitated solid was filtered and dried in high vacuo to afford the title compound (1.40 g, quantitative) as a light yellow oil. MS: 331.9 ([{$^{35}$Cl, $^{35}$Cl}M+H]$^+$), 333.9 ([{$^{35}$Cl, $^{37}$Cl}M+H]$^+$), ESI pos. This crude material was used as such in the following step without further purification.

d) 6,7-dichloro-5-(2,6-difluoro-3-methoxy-phenyl)-1,3-dihydro-1,4-benzodiazepin-2-one In analogy to experiment of Building block A e, (6-amino-2,3-dichloro-phenyl)-(2,6-difluoro-3-methoxy-phenyl)methanone hydrochloride was converted into the title compound (500 mg, 37%) which was obtained as a red solid. MS: 371.0 ([{$^{35}$Cl, $^{35}$Cl}M+H]$^+$), 373.0 ([{$^{35}$Cl, $^{37}$Cl}M+H]$^+$), ESI pos.

Building Block F

6-chloro-5-(2-fluoro-5-methoxy-phenyl)-3-methyl-7-(trifluoromethyl)-1,3-dihydro-1,4-benzodiazepin-2-one

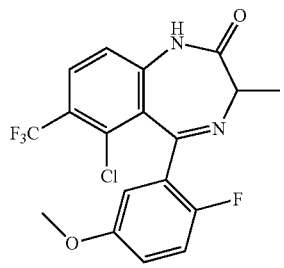 [SMILES: COc1ccc(F)c(C2=NC(C)C(=O)Nc3ccc(C(F)(F)F)c(Cl)c32)c1]

a) tert-butyl N-[2-[3-chloro-2-(2-fluoro-5-methoxy-benzoyl)-4-iodo-anilino]-1-methyl-2-oxo-ethyl]carbamate In analogy to experiment of building block C a, (6-amino-2-chloro-3-iodo-phenyl)-(2-fluoro-5-methoxy-phenyl)methanone (building block D a, 1.00 g, 2.47 mmol) was converted into the title compound (980 mg, 69%) which was obtained as a light yellow oil. MS: 599.0 ([{$^{35}$Cl}M+Na]$^+$), 601.0 ([{$^{37}$Cl}M+Na]f), ESI pos.

b) 2-amino-N-[3-chloro-2-(2-fluoro-5-methoxy-benzoyl)-4-iodo-phenyl]propanamide In analogy to experiment of building block C b, tert-butyl N-[2-[3-chloro-2-(2-fluoro-5-methoxy-benzoyl)-4-iodo-anilino]-1-methyl-2-oxo-ethyl]carbamate (860 mg, 1.49 mmol) was converted into the title compound (580 mg, 82%) which was obtained as a light yellow oil. MS: 476.9 ([{$^{35}$Cl}M+H]$^+$), 478.9 ([{$^{37}$Cl}M+H]$^+$), ESI pos.

c) 6-chloro-5-(2-fluoro-5-methoxy-phenyl)-7-iodo-3-methyl-1,3-dihydro-1,4-benzodiazepin-2-one In analogy to experiment of building block C c, 2-amino-N-[3-chloro-2-(2-fluoro-5-methoxy-benzoyl)-4-iodo-phenyl]propanamide (650 mg, 1.36 mmol) was converted into the title compound (500 mg, 80%) which was obtained as a light yellow oil. MS: 458.9 ([{$^{35}$Cl}M+H]$^+$), 460.9 ([{$^{37}$Cl}M+H]$^+$), ESI pos.

d) 6-chloro-5-(2-fluoro-5-methoxy-phenyl)-3-methyl-7-(trifluoromethyl)-1,3-dihydro-1,4-benzodiazepin-2-one In analogy to experiment of building block D c, 6-chloro-5-(2-fluoro-5-methoxy-phenyl)-7-iodo-3-methyl-1,3-dihydro-1,4-benzodiazepin-2-one (500 mg, 1.09 mmol) was converted into the title compound (275 mg, 63%) which was obtained as a light yellow oil. MS: 458.9 ([{$^{35}$Cl}M+H]$^+$), 460.9 ([{$^{37}$Cl}M+H]$^+$), ESI pos.

Building Block G

6,7-dichloro-5-(2,6-difluoro-3-methoxy-phenyl)-3-methyl-1,3-dihydro-1,4-benzodiazepin-2-one

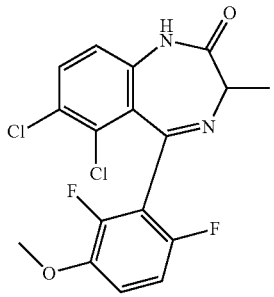

a) tert-butyl N-[2-[3,4-dichloro-2-(2,6-difluoro-3-methoxy-benzoyl)anilino]-1-methyl-2-oxo-ethyl]carbamate In analogy to experiment of building block C a, (6-amino-2,3-dichloro-phenyl)-(2,6-difluoro-3-methoxy-phenyl)methanone (building block E c, 4.1 g, 12 mmol) was converted into the title compound (4.5 g, 72%) which was obtained as a brown oil. MS: 403.0 ([{$^{35}$Cl, $^{35}$Cl}M+H-Boc]$^+$), 405.0 ([{$^{35}$Cl, $^{37}$Cl}M+H-Boc]$^+$), ESI pos. This crude material was used as such in the next step without further purification.

b) 2-amino-N-[3,4-dichloro-2-(2,6-difluoro-3-methoxy-benzoyl)phenyl]propanamide In analogy to experiment of building block C b, tert-butyl N-[2-[3,4-dichloro-2-(2,6-difluoro-3-methoxy-benzoyl)anilino]-1-methyl-2-oxo-ethyl]carbamate was converted into the title compound (3.2 g, 89%) which was obtained as a brown oil. MS: 403.0 ([{$^{35}$Cl, $^{35}$Cl}M+H]$^+$), 405.0 ([{$^{35}$Cl, $^{37}$Cl}M+H]$^+$), ESI pos. This crude material was used as such in the next step without further purification.

c) 6,7-dichloro-5-(2,6-difluoro-3-methoxy-phenyl)-3-methyl-1,3-dihydro-1,4-benzodiazepin-2-one In analogy to experiment of building block C c, 2-amino-N-[3,4-dichloro-2-(2,6-difluoro-3-methoxy-benzoyl)phenyl]propanamide was converted into the title compound (500 mg, 33%) which was obtained as a light yellow oil. MS: 385.0 ([{$^{35}$Cl, $^{35}$Cl}M+H]$^+$), 387.0 ([{$^{35}$Cl, $^{37}$Cl}M+H]$^+$), ESI pos.

Building Block H

(3S)-6-chloro-5-(3-fluoro-6-methoxy-2-pyridyl)-3-methyl-7-(trifluoromethyl)-1,3-dihydro-1,4-benzodiazepin-2-one

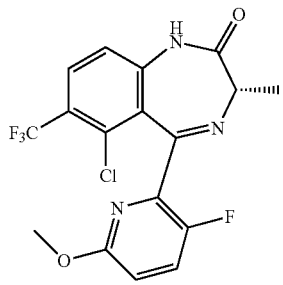 [SMILES: COc1ccc(F)c(C2=N[C@@H](C)C(=O)Nc3ccc(C(F)(F)F)c(Cl)c32)n1]

a) [6-bromo-2-chloro-3-(trifluoromethyl)phenyl]-(3-fluoro-6-methoxy-2-pyridyl)methanol To a solution of N,N-diisopropylamine (294 mg, 0.414 mL, 2.91 mmol) in anhydrous tetrahydrofuran (8 mL) was added at −20° C. n-BuLi (1.6 M in hexane, 1.68 mL, 2.68 mmol) dropwise. After stirring for 15 min at −20°, the LDA solution was cooled to −60° C. A solution of 4-bromo-2-chloro-1-(trifluoromethyl)benzene (580 mg, 2.24 mmol) in anhydrous tetrahydrofuran (2 mL) was added dropwise. The mixture was stirred for 45 min at −60° C., then 3-fluoro-6-methoxy-pyridine-2-carbaldehyde (486 mg, 3.13 mmol) was added in one portion. The reaction mixture was allowed to warm to 0° C. under stirring. The reaction mixture was quenched with aqueous NH$_4$Cl and extracted with ethyl acetate (2×60 mL). The organic layers were washed with water (60 mL) and brine (60 mL), dried (Na$_2$SO$_4$), filtered and concentrated in vacuo. The residue was purified by flash column chromatography (silica, 0-30% ethyl acetate in heptane) to afford the title compound (880 mg, 95%) as a white solid. MS: 414.0 ([{$^{79}$Br, $^{35}$Cl}M+H]$^+$), 416.0 ([{$^{81}$Br, $^{35}$Cl or $^{79}$Br, $^{37}$Cl}M+H]$^+$), ESI pos.

b) [6-bromo-2-chloro-3-(trifluoromethyl)phenyl]-(3-fluoro-6-methoxy-2-pyridyl)methanone To a solution of [6-bromo-2-chloro-3-(trifluoromethyl)phenyl]-(3-fluoro-6-methoxy-2-pyridyl)methanol (878 mg, 2.12 mmol) in dichloromethane (5 mL) was added at 23° C. manganese dioxide (3.68 g, 42.4 mmol). The reaction mixture was stirred at 23° C. for 60 h. The suspension was filtered off. The filtrate was concentrated in vacuo to afford the title compound (855 mg, 97%) as a white solid. MS: 412.0 ([{$^{79}$Br, $^{35}$Cl}M+H]$^+$), 414.0 ([{$^{81}$Br, $^{35}$Cl or $^{79}$Br, $^{37}$Cl}M+H]$^+$), ESI pos.

c) tert-butyl N-[3-chloro-2-(3-fluoro-6-methoxy-pyridine-2-carbonyl)-4-(trifluoromethyl)phenyl]carbamate In a seal tube was added [6-bromo-2-chloro-3-(trifluoromethyl)phenyl]-(3-fluoro-6-methoxy-2-pyridyl)methanone (79 mg, 0.191 mmol), tert-butyl carbamate (38.1 mg, 0.326 mmol) and tripotassium phosphate (73 mg, 0.345 mmol) and toluene (2 mL), and the suspension was degassed by bubbling argon through for 15 min. Then, rac-BINAP- Pd-G4 (57.8 mg, 0.057 mmol) was added, bubbling was continued for 5 min: the tube was sealed and the reaction mixture was stirred at 100° C. for 16 h. The reaction was quenched with water (10 mL) and extracted with ethyl acetate (2×40 mL). The combined organic layers were washed with brine (20 mL), dried (Na2SO4), filtered and concentrated in vacuo. The residue was purified by flash column chromatography (silica, 0-30% ethyl acetate in heptane) to afford the title compound (49 mg, 57%) as a white foam. MS: 447.1 ([$\{^{35}Cl\}$M+H]$^+$), 449.1 ([$\{^{37}Cl\}$M+H]$^+$), ESI neg.

d) [6-amino-2-chloro-3-(trifluoromethyl)phenyl]-(3-fluoro-6-methoxy-2-pyridyl)methanone To a solution of tert-butyl N-[3-chloro-2-(3-fluoro-6-methoxy-pyridine-2-carbonyl)-4-(trifluoromethyl)phenyl]carbamate (57 mg, 0.127 mmol) in dichloromethane (20 mL) was added at 0° C. trifluoroacetic acid (290 mg, 0.200 mL, 2.54 mmol). The light brown reaction mixture was stirred at 23° C. for 16 h, then concentrated in vacuo. The residue was dissolved in dichloromethane (20 mL), saturated aqueous NaHCO₃ (20 mL) was added. The aqeuous layer was extracted with dichloromethane (2×20 mL). The combined organic layers were washed with water (20 mL) and brine (20 mL), dried (Na₂SO₄), filtered and concentrated in vacuo to afford the title compound (43 mg, 89%) as a yellow oil. MS: 349.0 ([$\{^{35}Cl\}$M+H]$^+$), 351.0 ([$\{^{37}Cl\}$M+H]$^+$), ESI pos.

e) tert-butyl N-[(1S)-2-[3-chloro-2-(3-fluoro-6-methoxy-pyridine-2-carbonyl)-4-(trifluoromethyl)anilino]-1-methyl-2-oxo-ethyl]carbamate In analogy to experiment of building block C a, [6-amino-2-chloro-3-(trifluoromethyl)phenyl]-(3-fluoro-6-methoxy-2-pyridyl)methanone was converted into the title compound (185 mg, 67%) which was obtained as a white foam. MS: 518.2 ([$\{^{35}Cl\}$M+H]$^+$), 520.2 ([$\{^{37}Cl\}$M+H]$^+$), ESI neg.

f) (2S)-2-amino-N-[3-chloro-2-(3-fluoro-6-methoxy-pyridine-2-carbonyl)-4-(trifluoromethyl)phenyl]propanamide In analogy to experiment of building block H d, tert-butyl N-[(1S)-2-[3-chloro-2-(3-fluoro-6-methoxy-pyridine-2-carbonyl)-4-(trifluoromethyl)anilino]-1-methyl-2-oxo-ethyl]carbamate was converted into the title compound (153 mg, 100%) which was obtained as a colourless oil. MS: 420.1 ([$\{^{35}Cl\}$M+H]$^+$), 422.1 ([$\{^{37}Cl\}$M+H]$^+$), ESI pos.

g) (3S)-6-chloro-5-(3-fluoro-6-methoxy-2-pyridyl)-3-methyl-7-(trifluoromethyl)-1,3-dihydro-1,4-benzodiazepin-2-one In analogy to experiment of building block C c, (2S)-2-amino-N-[3-chloro-2-(3-fluoro-6-methoxy-pyridine-2-carbonyl)-4-(trifluoromethyl)phenyl]propanamide was converted into the title compound (141 mg, 96%) which was obtained as a white solid. MS: 402.1 ([$\{^{35}Cl\}$M+H]$^+$), 404.1 ([$\{^{37}Cl\}$M+H]$^+$), ESI pos.

Building Block I

(3S)-6-chloro-5-(3-chloro-6-methoxy-2-pyridyl)-3-methyl-7-(trifluoromethyl)-1,3-dihydro-1,4-benzodiazepin-2-one

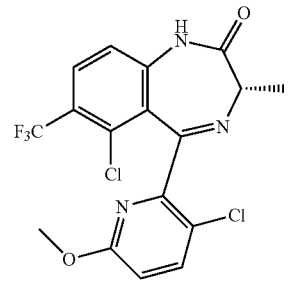 [SMILES: COc1ccc(Cl)c(C2=N[C@@H](C)C(=O)Nc3ccc(C(F)(F)F)c(Cl)c32)n1]

a) [6-bromo-2-chloro-3-(trifluoromethyl)phenyl]-(3-chloro-6-methoxy-2-pyridyl)methanol In analogy to experiment of building block H a, 4-bromo-2-chloro-1-(trifluoromethyl)benzene using 3-chloro-6-methoxy-pyridine-2-carbaldehyde instead of 3-fluoro-6-methoxy-pyridine-2-carbaldehyde was converted into the title compound (13.48 g, 81%) which was obtained as a white solid. MS: 430.0 ([$\{^{79}Br, ^{35}Cl\}$ M+H]$^+$), 432.0 ([$\{^{81}Br, ^{35}Cl$ or $^{79}Br, ^{37}Cl\}$ M+H]$^+$), 434.0 ([$\{^{81}Br, ^{37}Cl\}$ M+H]$^+$), ESI pos.

b) [6-bromo-2-chloro-3-(trifluoromethyl)phenyl]-(3-chloro-6-methoxy-2-pyridyl)methanone In analogy to experiment of building block H b, [6-bromo-2-chloro-3-(trifluoromethyl)phenyl]-(3-chloro-6-methoxy-2-pyridyl)methanol was converted into the title compound (13.54 g, 100%) which was obtained as a colorless oil. MS: 428.0 ([$\{^{79}Br, ^{35}Cl\}$ M+H]), 430.0 ([$\{^{81}Br, ^{35}Cl$ or $^{79}Br, ^{37}Cl\}$ M+H]$^+$), 432.0 ([$\{^{81}Br, ^{37}Cl\}$ M+H]$^+$), ESI pos.

c) tert-butyl N-[(1S)-2-[3-chloro-2-(3-chloro-6-methoxy-pyridine-2-carbonyl)-4-(trifluoromethyl)anilino]-1-methyl-2-oxo-ethyl]carbamate In analogy to experiment of building block H c, [6-bromo-2-chloro-3-(trifluoromethyl)phenyl]-(3-chloro-6-methoxy-2-pyridyl)methanone using tert-butyl N-[(1S)-2-amino-1-methyl-2-oxo-ethyl]carbamate instead of tert-butyl carbamate was converted into the title compound (570 mg, 75%) which was obtained as a light yellow foam. MS: 536.3 ([$\{^{35}Cl, ^{35}Cl\}$M+H]$^+$), 538.2 ([$\{^{35}Cl, ^{37}Cl\}$M+H]$^+$), ESI pos.

d) (2S)-2-amino-N-[3-chloro-2-(3-chloro-6-methoxy-pyridine-2-carbonyl)-4-(trifluoromethyl)phenyl]propanamide In analogy to experiment of building block H d, tert-butyl N-[(1S)-2-[3-chloro-2-(3-chloro-6-methoxy-pyridine-2-carbonyl)-4-(trifluoromethyl)anilino]-1-methyl-2-oxo-ethyl]carbamate was converted into the title compound (1.3 g, e) (3S)-6-chloro-5-(3-chloro-6-methoxy-2-pyridyl)-3-methyl-7-(trifluoromethyl)-1,3-dihydro-1,4-benzodiazepin-2-one In analogy to experiment of building block C c, (2S)-2-amino-N-[3-chloro-2-(3-chloro-6-methoxy-pyridine-2-carbonyl)-4-(trifluoromethyl)phenyl]propanamide was converted into the title compound (1.13 g, 90%) which was obtained as a light yellow foam. MS: 418.0 ([$\{^{35}Cl, ^{35}Cl\}M+H$]$^+$), 420.0 ([$\{^{35}Cl, ^{37}Cl\}M+H$]$^+$), ESI pos.

Building Block J (3S)-5-(6-benzyloxy-3-fluoro-2-pyridyl)-6-chloro-3-methyl-7-(trifluoromethyl)-1,3-dihydro-1,4-benzodiazepin-2-one

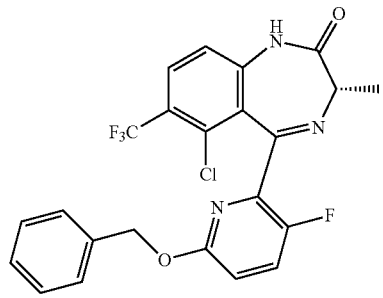 [SMILES: C[C@@H]1N=C(c2nc(OCc3ccccc3)ccc2F)c2c(ccc(C(F)(F)F)c2Cl)NC1=O]

a) 6-benzyloxy-3-fluoro-pyridine-2-carbaldehyde

To a mixture of 2-benzoxy-5-fluoro-pyridine (CAS 1305322-95-5, 2 g, 9.35 mmol) in anhydrous tetrahydrofuran (38 mL) cooled to −25° C. to −30° C. was added 2,2,6,6-tetramethylpiperidinylmagnesium chloride lithium chloride complex (1 M in THF/toluene, 11.52 g, 12 mL, 12 mmol) dropwise. The mixture was stirred for 0.5 h at −25° C. to −30° C., then at 0° C. for 0.5 h and at room temperature for 0.5 h. The reaction mixture was cooled to −25° C. to −30° C. and N,N-dimethylformamide (2.83 g, 3 mL, 38.74 mmol) was added dropwise. The mixture was stirred at −25° C. to −30° C. for 45 min and at room temperature for 0.5 h, then warmed in an ice bath and quenched by addition of water (340 uL, 18.87 mmol) followed by acetic acid (540 uL, 9.43 mmol). The reaction mixture was filtered over a pad of sodium sulfate, rinsed with ethyl acetate. The filtrate was adsorbed on ISOLUTE HM-N and concentrated in vacuo. The residue was purified by flash column chromatography (silica gel, 0-5% ethyl acetate in heptane) to afford the title compound (1.21 g, 53%) as a light yellow solid. MS: 232.1 ([M+H]), ESI pos.

b) (6-benzyloxy-3-fluoro-2-pyridyl)-[6-bromo-2-chloro-3-(trifluoromethyl)phenyl]methanol In analogy to experiment of building block H a, 4-bromo-2-chloro-1-(trifluoromethyl)benzene using 6-benzyloxy-3-fluoro-pyridine-2-carbaldehyde instead of 3-fluoro-6-methoxy-pyridine-2-carbaldehyde was converted into the title compound (6.8 g, 78%) which was obtained as a light yellow solid. MS: 490.0 ([$\{^{79}Br, ^{35}Cl\}M+H$]$^+$), 492.0 ([$\{^{81}Br, ^{35}Cl$ or $^{79}Br, ^{37}Cl\}M+H$]$^+$), ESI pos.

c) (6-benzyloxy-3-fluoro-2-pyridyl)-[6-bromo-2-chloro-3-(trifluoromethyl)phenyl]methanone In analogy to experiment of building block H b, (6-benzyloxy-3-fluoro-2-pyridyl)-[6-bromo-2-chloro-3-(trifluoromethyl)phenyl]methanol was converted into the title compound (6.44 g, 93%) which was obtained as a light yellow solid. MS: 488.0 ([$\{^{79}Br, ^{35}Cl\}M+H$]$^+$), 490.0 ([$\{^{81}Br, ^{35}Cl$ or $^{79}Br, ^{37}Cl\}M+H$]$^+$), ESI pos.

d) tert-butyl N-[(1S)-2-[2-(6-benzyloxy-3-fluoro-pyridine-2-carbonyl)-3-chloro-4-(trifluoromethyl)anilino]-1-methyl-2-oxo-ethyl]carbamate In analogy to experiment of building block H c, (6-benzyloxy-3-fluoro-2-pyridyl)-[6-bromo-2-chloro-3-(trifluoromethyl)phenyl]methanone using tert-butyl N-[(1S)-2-amino-1-methyl-2-oxo-ethyl]carbamate instead of tert-butyl carbamate was converted into the title compound (3.09 g, 85%) which was obtained as a light brown foam. MS: 594.3 ([$\{^{35}Cl\}M−H$]$^−$), 596.2 ([$\{^{37}Cl\}$ M−H]$^+$), ESI neg.

e) (3S)-5-(6-benzyloxy-3-fluoro-2-pyridyl)-6-chloro-3-methyl-7-(trifluoromethyl)-1,3-dihydro-1,4-benzodiazepin-2-one To a solution of tert-butyl N-[(1S)-2-[2-(6-benzyloxy-3-fluoro-pyridine-2-carbonyl)-3-chloro-4-(trifluoromethyl)anilino]-1-methyl-2-oxo-ethyl]carbamate (4.5 g, 6.8 mmol) in toluene (100 mL) was added at room temperature silica gel (40-200 mesh, 26.95 g, 448 mmol), 4A molecular sieves (3 g) and trifluoroacetic acid (1.55 g, 1.05 mL, 13.59 mmol). The mixture was stirred at 110° C. overnight. The reaction mixture was cooled to room temperature, filtered and washed with ethyl acetate and methanol. The filtrate was concentrated in vacuo. The residue was purified by flash column chromatography (silica, 0-20% ethyl acetate in heptane) to afford the title compound (3.3 g, 97%) as a light yellow solid. MS: 478.2 ([$\{^{35}Cl\}M+H$]$^+$), 480.2 ([$\{^{37}Cl\}M+H$]$^+$), ESI pos.

$^{11}$C Radiolabeling Precursor 1

5-[5-[tert-butyl(dimethyl)silyl]oxy-2-fluoro-phenyl]-6,7-dichloro-1,3-dihydro-1,4-benzodiazepin-2-one

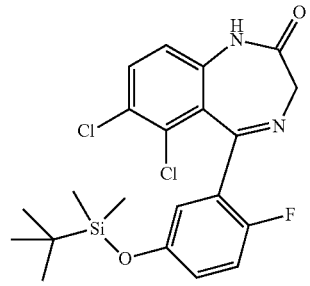 [SMILES: CC(C)(C)[Si](C)(C)Oc1ccc(F)c(C2=NCC(=O)Nc3ccc(Cl)c(Cl)c32)c1]

a) tert-butyl N-[3,4-dichloro-2-[(2-fluoro-5-methoxy-phenyl)-hydroxy-methyl]phenyl]carbamate To a solution of tert-butyl N-(3,4-dichlorophenyl)carbamate (5.82 g, 22.2 mmol) in THF (64 mL) was added dropwise from a dry-ice-cooled dropping-funnel at −90° C. tert-butyllithium, 1.7 M in pentane (28.7 ml, 48.8 mmol) and the resulting mixture was stirred at −85° C. for an additional 0.5 h. Then was added dropwise from a dry-ice-cooled dropping-funnel at −85 to −90° C. a solution of 2-fluoro-5-methoxybenzaldehyde (3.76 g, 24.4 mmol) in THF (16 ml). After stirring at −90 to −85° C. for an additional 0.5 h the mixture was allowed to warm to −65° C. and was then quenched by dropwise addition of saturated aqueous NH₄Cl. The mixture was diluted with water and extracted with ethyl acetate. The organic layer was washed with brine, dried over sodium sulfate, filtered and concentrated in vacuo. The residue was suspended in DCM, the solid was filtered and dried in high vacuum to afford the title compound (4.29 g, 46%) as a white solid. MS: 414.2 ([$\{^{35}Cl, ^{35}Cl\}M-H]^-$), 416.2 ([$\{^{35}Cl, ^{37}Cl\}M-H]^-$), ESI neg.

b) (6-amino-2,3-dichloro-phenyl)-(2-fluoro-5-methoxy-phenyl)methanone

To a solution of tert-butyl N-[3,4-dichloro-2-[(2-fluoro-5-methoxy-phenyl)-hydroxy-methyl]phenyl]carbamate (8.60 g, 20.8 mmol) in DCM (200 mL) was added at 22° C. trifluoroacetic acid (47.3 g, 415 mmol) and the mixture was stirred at 22° C. for 2 h. The solution was concentrated in vacuo. The residue (combined with another batch—17.9 mmol-scale) was treated with saturated aqueous NaHCO₃ and extracted with ethyl acetate. The organic layer was dried over magnesium sulfate, filtered and concentrated in vacuo to afford the title compound (11.0 g, 90%) as a yellow solid. MS: 314.0 ([$\{^{35}Cl, ^{35}Cl\}M+H]^+$), 316.0 ([$\{^{35}Cl, ^{37}Cl\}M+H]^+$), ESI pos.

c) 6,7-dichloro-5-(2-fluoro-5-methoxy-phenyl)-1,3-dihydro-1,4-benzodiazepin-2-one A solution of (6-amino-2,3-dichloro-phenyl)-(2-fluoro-5-methoxy-phenyl)methanone (8.35 g, 26.6 mmol) in pyridine (165 mL) was heated to 90° C., then ethyl glycinate hydrochloride (26.0 g, 186 mmol) was added in one portion, and the resulting mixture was stirred at 110° C. for 4 h. The mixture was cooled to 90° C., then further ethyl glycinate hydrochloride (14.8 g, 106 mmol) was added, and stirring at 110° C. was continued for 16 h. The mixture was cooled to room temperature and concentrated in vacuo. The residue was treated with saturated aqueous NaHCO₃ and extracted with ethyl acetate. The organic layer was washed with brine, dried over sodium sulfate, filtered and concentrated in vacuo. The residue was purified by flash column chromatography (silica, 10-100% ethyl acetate in heptane) to afford the title compound (5.47 g, 58%) as a yellow solid. MS: 353.0 ([$\{^{35}Cl, ^{35}Cl\}M+H]^+$), 355.0 ([$\{^{35}Cl, ^{37}Cl\}M+H]^+$), ESI pos.

d) 6,7-dichloro-5-(2-fluoro-5-hydroxy-phenyl)-1,3-dihydro-1,4-benzodiazepin-2-one To a light yellow solution of 6,7-dichloro-5-(2-fluoro-5-methoxy-phenyl)-1,3-dihydro-1,4-benzodiazepin-2-one (500 mg, 1.42 mmol) in DCM (15 mL) was added dropwise at −65° C. boron tribromide (1.77 g, 7.08 mmol). The mixture was allowed to warm to −20° C. and stirred for 0.5 h. The mixture was quenched with half-saturated aqueous NaHCO₃ and extracted with DCM. The organic layer was washed with half-saturated aqueous NaHCO₃, dried over sodium sulfate, filtered and concentrated in vacuo. The aqueous layer was again extracted with ethyl acetate, the organic layer was dried over sodium sulfate, filtered and concentrated in vacuo. Both residues were combined and purified by flash column chromatography (silica, 10-100% ethyl acetate in heptane) followed by crystallization from MTBE/heptane to afford the title compound (220 mg, 46%) as a light yellow solid. MS: 339.0 ([$\{^{35}Cl, ^{35}Cl\}M+H]^+$), 341.0 ([$\{^{35}Cl, ^{37}Cl\}M+H]^+$), ESI pos.

e) 5-[5-[tert-butyl(dimethyl)silyl]oxy-2-fluoro-phenyl]-6,7-dichloro-1,3-dihydro-1,4-benzodiazepin-2-one To a solution of 6,7-dichloro-5-(2-fluoro-5-hydroxy-phenyl)-1,3-dihydro-1,4-benzodiazepin-2-one (175 mg, 0.516 mmol) in DMF (1.75 mL) was added at 22° C. imidazole (77.3 mg, 1.14 mmol) followed by tert-butyldimethylchlorosilane (85.5 mg, 0.568 mmol) and the resulting mixture was stirred at 22° C. for 0.5 h. The mixture was concentrated in vacuo. The residue was treated with aqueous NaOH (0.1 M) and extracted with ethyl acetate. The organic layer was washed with aqueous NaOH (0.1 M) and brine successively, dried over sodium sulfate, filtered and concentrated in vacuo. The residue was purified by flash column chromatography (silica, 0-30% ethyl acetate in heptane) followed by crystallization from ethyl acetate/heptane to afford the title compound (122 mg, 52%) as a white solid. MS: 453.2 ([$\{^{35}Cl, ^{35}Cl\}M+H]^+$), 455.1 ([$\{^{35}Cl, ^{37}Cl\}M+H]^+$), ESI pos.

¹¹C Radiolabeling Precursor 2

5-[5-[tert-butyl(dimethyl)silyl]oxy-2-fluoro-phenyl]-6-chloro-7-methyl-1,3-dihydro-1,4-benzodiazepin-2-one

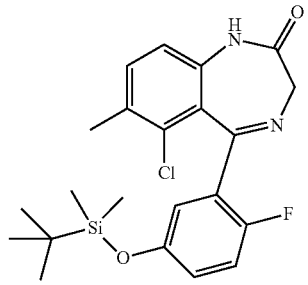 [SMILES: Cc1ccc2c(c1Cl)C(c1cc(O[Si](C)(C)C(C)(C)C)ccc1F)=NCC(=O)N2]

a) 5-chloro-2-methyl-3,1-benzoxazin-4-one

In analogy to experiment of building block A a, 2-amino-6-chloro-benzoic acid was converted into the title compound (23.8 g, 70%) which was obtained as a brown solid. ¹H NMR (CDCl₃, 300 MHz) δ ppm: 2.45 (s, 3H), 7.45 (dd, J=8.06, 1.21 Hz, 1H), 7.51 (dd, J=8.06, 1.21 Hz, 1H), 7.65 (dd, J=1.00 Hz, 1H).

b) N-[3-chloro-2-(2-fluoro-5-methoxy-benzoyl)phenyl]acetamide

In analogy to experiment of building block A b, 5-chloro-2-methyl-3,1-benzoxazin-4-one was converted into the title compound (8.84 g, 53%) which was obtained as a light yellow solid. MS: 322.1 ([$\{^{35}Cl\}M+H]^+$), 324.1 ([$\{^{37}Cl\}M+H]^+$), ESI pos.

c) (2-amino-6-chloro-phenyl)-(2-fluoro-5-methoxy-phenyl)methanone

In analogy to experiment of building block A c, N-[3-chloro-2-(2-fluoro-5-methoxy-benzoyl)phenyl]acetamide was converted into the title compound (17.96 g, quant.) which was obtained as a brown oil. MS: 280.1 ([{$^{35}$Cl}M+H]$^+$), 282.1 ([{$^{37}$Cl}M+H]$^+$), ESI pos.

d) (6-amino-3-bromo-2-chloro-phenyl)-(2-fluoro-5-methoxy-phenyl)methanone

In analogy to experiment of building block B d, (2-amino-6-chloro-phenyl)-(2-fluoro-5-methoxy-phenyl)methanone was converted into the title compound (15.24 g, 66%) which was obtained as a brown solid. MS: 358.0 ([{$^{79}$Br, $^{35}$Cl}M+H]$^+$), 360.0 ([{$^{81}$Br, $^{35}$Cl or $^{79}$Br, $^{37}$Cl}M+H]$^+$), ESI pos.

e) 7-bromo-6-chloro-5-(2-fluoro-5-methoxy-phenyl)-1,3-dihydro-1,4-benzodiazepin-2-one In analogy to experiment of building block B e, (6-amino-3-bromo-2-chloro-phenyl)-(2-fluoro-5-methoxy-phenyl)methanone was converted into the title compound (2.47 g, 45%) which was obtained as a green solid. MS: 397.0 ([{$^{79}$Br, $^{35}$Cl}M+H]$^+$), 399.0 ([{$^{81}$Br, $^{35}$Cl or $^{79}$Br, $^{37}$Cl}M+H]$^+$), ESI pos.

f) 6-chloro-5-(2-fluoro-5-methoxy-phenyl)-7-methyl-1,3-dihydro-1,4-benzodiazepin-2-one In analogy to experiment of building block B f, 7-bromo-6-chloro-5-(2-fluoro-5-methoxy-phenyl)-1,3-dihydro-1,4-benzodiazepin-2-one (3.57 g, 8.98 mmol) was converted into the title compound (2.40 g, 80%) which was obtained as a light yellow solid. MS: 333.1 ([{$^{79}$Br, $^{35}$Cl}M+H]$^+$), 335.1 ([{$^{81}$Br, $^{35}$Cl or $^{79}$Br, $^{37}$Cl}M+H]$^+$), ESI pos.

g) 6-chloro-5-(2-fluoro-5-hydroxy-phenyl)-7-methyl-1,3-dihydro-1,4-benzodiazepin-2-one To a solution of 6-chloro-5-(2-fluoro-5-methoxy-phenyl)-7-methyl-1,3-dihydro-1,4-benzodiazepin-2-one (500 mg, 1.50 mmol) in DCM (15 mL) was added at −65° C. boron tribromide (1.88 g, 7.51 mmol). The mixture was stirred at −60° C. for 0.5 h. The mixture was then warmed to −20° C. and stirred for 0.5 h. The mixture was quenched with saturated aqueous NaHCO$_3$ and extracted with ethyl acetate. The organic layer was dried over sodium sulfate, filtered and concentrated in vacuo. The residue was purified by flash column chromatography (silica, 10-100% ethyl acetate in petroleum ether) followed by crystallization from ethyl acetate/heptane to afford the title compound (177 mg, 37%) as a light yellow solid. MS: 319.1 ([{$^{79}$Br, $^{35}$Cl}M+H]$^+$), 321.1 ([{$^{81}$Br, $^{35}$Cl or $^{79}$Br, $^{37}$Cl}M+H]$^+$), ESI pos.

h) 5-[5-[tert-Butyl(dimethyl)silyl]oxy-2-fluoro-phenyl]-6-chloro-7-methyl-1,3-dihydro-1,4-benzodiazepin-2-one To a solution of 6-chloro-5-(2-fluoro-5-hydroxy-phenyl)-7-methyl-1,3-dihydro-1,4-benzodiazepin-2-one (184 mg, 0.577 mmol) in DMF (1.8 mL) was added at 22° C. imidazole (86.5 mg, 1.27 mmol) followed by tert-butyldimethylchlorosilane (95.7 mg, 0.635 mmol) and the mixture was stirred at 22° C. for 1 h. The mixture was concentrated in vacuo, treated with aqueous NaOH (0.1 M) and extracted with ethyl acetate. The organic layer was washed with aqueous NaOH (0.1 M) and brine, dried over sodium sulfate, filtered and concentrated in vacuo. The residue was purified by flash column chromatography (silica, 0-45% ethyl acetate in petroleum ether) followed by crystallization from ethyl acetate/heptane to afford the title compound (110 mg, 44%) as a white solid. MS: 433.2 ([{$^{79}$Br, $^{35}$Cl}M+H]$^+$), 435.2 ([{$^{81}$Br, $^{35}$Cl or $^{79}$Br, $^{37}$Cl}M+H]$^+$), ESI pos.

EXAMPLES

Example 1

6,7-dichloro-5-(2-fluoro-5-hydroxy-phenyl)-1-methyl-3H-1,4-benzodiazepin-2-one

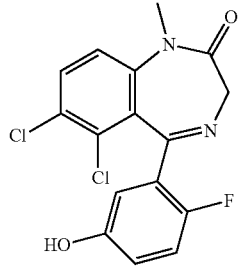 [SMILES: CN1C(=O)CN=C(c2cc(O)ccc2F)c2c1ccc(Cl)c2Cl]

a) 6,7-dichloro-5-(2-fluoro-5-methoxy-phenyl)-1-methyl-3H-1,4-benzodiazepin-2-one A solution of 6,7-dichloro-5-(2-fluoro-5-methoxy-phenyl)-1,3-dihydro-1,4-benzodiazepin-2-one (building block A, 120 mg, 0.340 mmol), iodomethane (1.00 g, 7.05 mmol) and potassium carbonate (70 mg, 0.51 mmol) in DMF (3 mL) was stirred at 25° C. for 0.5 h. The reaction was quenched with water and extracted with ethyl acetate. The organic layer was dried over sodium sulfate, filtered and concentrated in vacuo. The residue was purified by preparative HPLC (Phenomenex Synergi C18, 10 µm, 150×25 mm, 0.1% trifluoroacetic acid in water/acetonitrile) to afford the title compound (114 mg, 91%) as a white solid. MS: 367.1 ([{$^{35}$Cl, $^{35}$Cl}M+H]$^+$), 369.1 ([{$^{35}$Cl, $^{37}$Cl}M+H]$^+$), ESI pos.

b) 6,7-dichloro-5-(2-fluoro-5-hydroxy-phenyl)-1-methyl-3H-1,4-benzodiazepin-2-one To a solution of 6,7-dichloro-5-(2-fluoro-5-methoxy-phenyl)-1-methyl-3H-1,4-benzodiazepin-2-one (80 mg, 0.22 mmol) in DCM (9 mL) at 0° C. was added dropwise boron tribromide (273 mg, 1.09 mmol). The reaction mixture was stirred at 0° C. for 1 h, allowed to warm to room temperature and stirred for an additional 5 h. The reaction was quenched with ice-water and extracted with DCM. The organic layer was dried over sodium sulfate, filtered and concentrated in vacuo. The residue was purified by preparative HPLC (Phenomenex Synergi C18, 10 µm, 150×25 mm, 0.225% formic acid in water/acetonitrile) to afford the title compound (59 mg, 77%) as a white solid. MS: 353.1 ([{$^{35}$Cl, $^{35}$Cl}M+H]$^+$), 355.1 ([{$^{35}$Cl, $^{37}$Cl}M+H]$^+$), ESI pos.

Example 2

6-chloro-5-(2-fluoro-5-hydroxy-phenyl)-1,7-dimethyl-3H-1,4-benzodiazepin-2-one

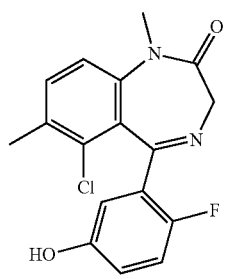 [SMILES: Cc1ccc2c(c1Cl)C(c1cc(O)ccc1F)=NCC(=O)N2C]

a) 6-chloro-5-(2-fluoro-5-methoxy-phenyl)-1,7-dimethyl-3H-1,4-benzodiazepin-2-one In analogy to experiment of example 1 a, 6-chloro-5-(2-fluoro-5-methoxy-phenyl)-7-methyl-1,3-dihydro-1,4-benzodiazepin-2-one (building block B) was converted into the title compound (76 mg, 36%) which was obtained as a yellow solid. MS: 347.1 ([{$^{35}$Cl}M+H]$^+$), 349.1 ([{$^{37}$Cl}M+H]$^+$), ESI pos.

b) 6-chloro-5-(2-fluoro-5-hydroxy-phenyl)-1,7-dimethyl-3H-1,4-benzodiazepin-2-one In analogy to experiment of example 1 b, 6-chloro-5-(2-fluoro-5-methoxy-phenyl)-1,7-dimethyl-3H-1,4-benzodiazepin-2-one was converted into the title compound (72 mg, 83%) which was obtained as an off-white solid. MS: 333.0 ([{$^{35}$Cl}M+H]$^+$), 335.0 ([{$^{37}$Cl}M+H]$^+$), ESI pos.

Example 3

3-(7,8-dichloro-1-methyl-4H-[1,2,4]triazolo[4,3-a][1,4]benzodiazepin-6-yl)-4-fluoro-phenol

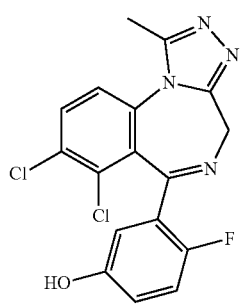 [SMILES: Cc1nnc2n1-c1ccc(Cl)c(Cl)c1C(c1cc(O)ccc1F)=NC2]

a) 6,7-dichloro-5-(2-fluoro-5-hydroxy-phenyl)-1,3-dihydro-1,4-benzodiazepin-2-one To a solution of 6,7-dichloro-5-(2-fluoro-5-methoxy-phenyl)-1,3-dihydro-1,4-benzodiazepin-2-one (building block A, 500 mg, 1.42 mmol) in DCM (15 mL) was added dropwise at −65° C. boron tribromide (1.77 g, 7.08 mmol) and the mixture was stirred at −20° C. for 0.5 h. The mixture was quenched with half-saturated aqueous NaHCO$_3$ and extracted with ethyl acetate. The organic layer was washed with half-saturated aqueous NaHCO$_3$, dried over sodium sulfate, filtered and concentrated in vacuo. The residue was purified by flash column chromatography (silica, 10-100% ethyl acetate in petroleum ether) followed by crystallization from MTBE/petroleum ether to afford the title compound (220 mg, 46%) as a light yellow solid. MS: 339.0 ([{$^{35}$Cl, $^{35}$Cl}M+H]$^+$), 341.0 ([{$^{35}$Cl, $^{37}$Cl}M+H]$^+$), ESI pos.

b) 5-[5-[tert-butyl(dimethyl)silyl]oxy-2-fluoro-phenyl]-6,7-dichloro-1,3-dihydro-1,4-benzodiazepin-2-one To a solution of 6,7-dichloro-5-(2-fluoro-5-hydroxy-phenyl)-1,3-dihydro-1,4-benzodiazepin-2-one (300 mg, 0.885 mmol) in DMF (12 mL) was added tert-butyldimethylchlorosilane (162 mg, 1.07 mmol) and imidazole (90 mg, 1.3 mmol). The mixture was stirred at 25° C. for 16 h, quenched with water and extracted with DCM. The organic layer was washed with brine, dried over sodium sulfate, filtered and concentrated in vacuo. The residue was purified by flash column chromatography (silica, 10-50% ethyl acetate in petroleum ether) to afford the title compound (380 mg, 95%) as a light yellow solid. MS: 453.2 ([{$^{35}$Cl, $^{35}$Cl}M+H]$^+$), 455.2 ([{$^{35}$Cl, $^{37}$Cl}M+H]$^+$), ESI pos.

c) 5-[5-[tert-butyl(dimethyl)silyl]oxy-2-fluoro-phenyl]-6,7-dichloro-1,3-dihydro-1,4-benzodiazepine-2-thione A mixture of 5-[5-[tert-butyl(dimethyl)silyl]oxy-2-fluoro-phenyl]-6,7-dichloro-1,3-dihydro-1,4-benzodiazepin-2-one (380 mg, 0.838 mmol) and Lawesson's reagent (407 mg, 1.01 mmol) in toluene (20 mL) was stirred at 100° C. for 5 h. The reaction mixture was cooled and concentrated in vacuo. The residue was purified by flash column chromatography (silica, 0-33% ethyl acetate in petroleum ether) to afford the title compound (110 mg, 28%) as a white solid. MS: 469.2 ([{$^{35}$Cl, $^{35}$Cl}M+H]$^+$), 471.2 ([{$^{35}$Cl, $^{37}$Cl}M+H]$^+$), ESI pos.

d) tert-butyl-[3-(7,8-dichloro-1-methyl-4H-[1,2,4]triazolo[4,3-a][1,4]benzodiazepin-6-yl)-4-fluoro-phenoxy]-dimethyl-silane A solution of 5-[5-[tert-butyl(dimethyl)silyl]oxy-2-fluoro-phenyl]-6,7-dichloro-1,3-dihydro-1,4-benzodiazepine-2-thione (100 mg, 0.213 mmol) and acethydrazide (63 mg, 0.85 mmol) in 1-butanol (10 mL) was stirred at 115° C. for 16 h. The mixture was concentrated in vacuo and the residue was purified by flash column chromatography (silica, 0-25% methanol in DCM) to afford the title compound (95 mg, 91%) as a light yellow oil. MS: 491.2 ([{$^{35}$Cl, $^{35}$Cl}M+H]$^+$), 493.2 ([{$^{35}$Cl, $^{37}$Cl}M+H]$^+$), ESI pos.

e) 3-(7,8-dichloro-1-methyl-4H-[1,2,4]triazolo[4,3-a][1,4]benzodiazepin-6-yl)-4-fluoro-phenol To a solution of tert-butyl-[3-(7,8-dichloro-1-methyl-4H-[1,2,4]triazolo[4,3-a][1,4]benzodiazepin-6-yl)-4-fluoro-phenoxy]-dimethyl-silane (95 mg, 0.19 mmol) in DCM (1 mL) was added trifluoroacetic acid (2.0 mL, 25.96 mmol) and the mixture was stirred at 50° C. for 5 h. The mixture was concentrated in vacuo and the residue was purified by preparative HPLC (Phenomenex Luna C18, 15 μm, 150×40 mm, 0.1% trifluoroacetic acid in water/acetonitrile) and further by preparative TLC (silica, DCM/methanol 10:1) to afford the title compound (35 mg, 48%) as a white solid. MS: 377.1 ([{$^{35}$Cl, $^{35}$Cl}M+H]$^+$), 379.1 ([{$^{35}$Cl, $^{37}$Cl}M+H]$^+$), ESI pos.

Example 4

4-fluoro-3-[(4S)-7,8-dichloro-1,4-dimethyl-4H-[1,2,4]triazolo[4,3-a][1,4]benzodiazepin-6-yl]phenol

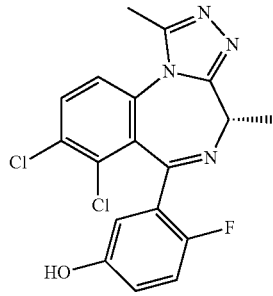 [SMILES: Cc1nnc2n1-c1ccc(Cl)c(Cl)c1C(c1cc(O)ccc1F)=N[C@H]2C]

a) 6,7-dichloro-5-(2-fluoro-5-methoxy-phenyl)-3-methyl-1,3-dihydro-1,4-benzodiazepine-2-thione In analogy to experiment of example 3 c, 6,7-dichloro-5-(2-fluoro-5-methoxy-phenyl)-3-methyl-1,3-dihydro-1,4-benzodiazepin-2-one (building block C) was converted into the title compound (530 mg, 85%) which was obtained as a yellow solid. MS: 383.0 ([{$^{35}$Cl, $^{35}$Cl}M+H]$^+$), 385.0 ([{$^{35}$Cl, $^{37}$Cl}M+H]$^+$), ESI pos.

b) 7,8-dichloro-6-(2-fluoro-5-methoxy-phenyl)-1,4-dimethyl-4H-[1,2,4]triazolo[4,3-a][1,4]benzodiazepine In analogy to experiment of example 3 d, 6,7-dichloro-5-(2-fluoro-5-methoxy-phenyl)-3-methyl-1,3-dihydro-1,4-benzodiazepine-2-thione was converted into the title compound (200 mg, 95%) which was obtained as a yellow solid. MS: 405.1 ([{$^{35}$Cl, $^{35}$Cl}M+H]$^+$), 407.1 ([{$^{35}$Cl, $^{37}$Cl}M+H]$^+$), ESI pos.

c) 4-fluoro-3-[(4S)-7,8-dichloro-1,4-dimethyl-4H-[1,2,4]triazolo[4,3-a][1,4]benzodiazepin-6-yl]phenol To a mixture of 7,8-dichloro-6-(2-fluoro-5-methoxy-phenyl)-1,4-dimethyl-4H-[1,2,4]triazolo[4,3-a][1,4]benzodiazepine (190 mg, 0.470 mmol) in DCM (10 mL) was added boron tribromide (143 mg, 0.570 mmol) and the mixture was stirred at 0° C. for 3 h. The reaction mixture was quenched with methanol, then water was added and the product was extracted with DCM. The organic layer was washed with brine, dried over sodium sulfate, filtered and concentrated in vacuo. The residue was purified (combined with another batch, 0.02 mmol scale) by preparative HPLC (Phenomenex Gemini-NX C18, 3 μm, 75×30 mm, 0.1% trifluoroacetic acid in water/acetonitrile), followed by chiral SFC (Daicel Chiralpak AD, 10 μm, 250×30 mm, 0.1% NH$_4$OH in ethanol; 40%) to afford the title compound (39 mg, 20%) as a white solid. MS: 391.0 ([{$^{35}$Cl, $^{35}$Cl}M+H]$^+$), 393.0 ([{$^{35}$Cl, $^{37}$Cl}M+H]$^+$), ESI pos.

Example 5

(5S)-8,9-dichloro-7-(2-fluoro-5-hydroxy-phenyl)-5-methyl-5H-pyrimido[1,2-a][1,4]benzodiazepin-3-one

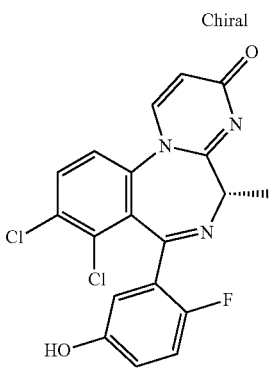 [SMILES: C[C@@H]1N=C(c2cc(O)ccc2F)c2c(ccc(Cl)c2Cl)-n2ccc(=O)nc21]

a) 6,7-dichloro-5-(2-fluoro-5-methoxy-phenyl)-3-methyl-3H-1,4-benzodiazepin-2-amine A mixture of 6,7-dichloro-5-(2-fluoro-5-methoxy-phenyl)-3-methyl-1,3-dihydro-1,4-benzodiazepine-2-thione (300 mg, 0.783 mmol) and aqueous ammonium hydroxide (33%, 0.20 mL, 0.78 mmol) in THF/methanol 5:1 (7.2 mL) was stirred at 50° C. for 16 h. The reaction mixture was cooled and concentrated in vacuo to afford the title compound (280 mg, 98%) as a yellow oil. This crude material was used as such in the following step without further characterization.

b) 8,9-dichloro-7-(2-fluoro-5-methoxy-phenyl)-5-methyl-5H-pyrimido[1,2-a][1,4]benzodiazepin-3-one A mixture of 6,7-dichloro-5-(2-fluoro-5-methoxy-phenyl)-3-methyl-3H-1,4-benzodiazepin-2-amine (280 mg, 0.765 mmol) and ethyl propiolate (375 mg, 3.82 mmol) in ethanol (6 mL) was stirred at 50° C. for 16 h. The reaction mixture was cooled and concentrated in vacuo. The residue was purified (combined with another batch, 0.115 mmol scale) by flash column chromatography (silica, DCM/methanol 1:0 to 10:1) to afford the title compound (310 mg, 97%) as a light yellow solid. MS: 418.1 ([{$^{35}$Cl, $^{35}$Cl}M+H]$^+$), 420.1 ([{$^{35}$Cl, $^{37}$Cl}M+H]$^+$), ESI pos.

c) (5S)-8,9-dichloro-7-(2-fluoro-5-hydroxy-phenyl)-5-methyl-5H-pyrimido[1,2-a][1,4]benzodiazepin-3-one In analogy to experiment of example 4 c, 8,9-dichloro-7-(2-fluoro-5-methoxy-phenyl)-5-methyl-5H-pyrimido[1,2-a][1,4]benzodiazepin-3-one was converted into the title compound (50 mg, 17%) which was obtained as a white solid. MS: 404.1 ([{$^{35}$Cl, $^{35}$Cl}M+H]$^+$), 406.1 ([{$^{35}$Cl, $^{37}$Cl}M+H]$^+$), ESI pos.

Example 6

8,9-dichloro-7-(2-fluoro-5-hydroxy-phenyl)-5H-pyrimido[1,2-a][1,4]benzodiazepin-3-one

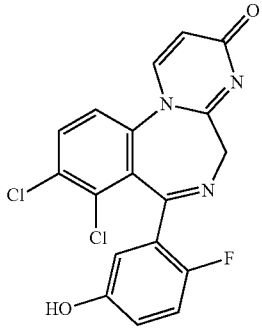 [SMILES: O=c1ccn2c(n1)CN=C(c1cc(O)ccc1F)c1c-2ccc(Cl)c1Cl]

a) 6,7-dichloro-5-(2-fluoro-5-methoxy-phenyl)-1,3-dihydro-1,4-benzodiazepine-2-thione In analogy to experiment of example 3 c, 6,7-dichloro-5-(2-fluoro-5-methoxy-phenyl)-1,3-dihydro-1,4-benzodiazepin-2-one (building block A) was converted into the title compound (230 mg, quantitative) which was obtained as a yellow solid. MS: 369.1 ([{$^{35}$Cl, $^{35}$Cl}M+H]$^+$), 371.1 ([{$^{35}$Cl, $^{37}$Cl}M+H]$^+$), ESI pos.

b) 6,7-dichloro-5-(2-fluoro-5-methoxy-phenyl)-3H-1,4-benzodiazepin-2-amine

In analogy to experiment of example 5 a, 6,7-dichloro-5-(2-fluoro-5-methoxy-phenyl)-1,3-dihydro-1,4-benzodiazepine-2-thione was converted into the title compound (260 mg, quantitative) which was obtained as a yellow oil. The crude was used as such in the following step without further characterization.

c) 8,9-dichloro-7-(2-fluoro-5-methoxy-phenyl)-5H-pyrimido[1,2-a][1,4]benzodiazepin-3-one In analogy to experiment of example 5 b, 6,7-dichloro-5-(2-fluoro-5-methoxy-phenyl)-3H-1,4-benzodiazepin-2-amine was converted into the title compound (180 mg, 89%) which was obtained as a brown oil. MS: 404.0 ([{$^{35}$Cl, $^{35}$Cl}M+H]$^+$), 406.0 ([{$^{35}$Cl, $^{37}$Cl}M+H]$^+$), ESI pos.

d) 8,9-dichloro-7-(2-fluoro-5-hydroxy-phenyl)-5H-pyrimido[1,2-a][1,4]benzodiazepin-3-one In analogy to experiment of example 1 b, 8,9-dichloro-7-(2-fluoro-5-methoxy-phenyl)-5H-pyrimido[1,2-a][1,4]benzodiazepin-3-one was converted into the title compound (44 mg, 25%) which was obtained as a yellow solid. MS: 390.1 ([{$^{35}$Cl, $^{35}$Cl}M+H]$^+$), 392.1 ([{$^{35}$Cl, $^{37}$Cl}M+H]$^+$), ESI pos.

Example 7

[7,8-dichloro-6-(2-fluoro-5-hydroxy-phenyl)-4H-[1,2,4]triazolo[1,5-a][1,4]benzodiazepin-2-yl]-(3-methoxyazetidin-1-yl)methanone

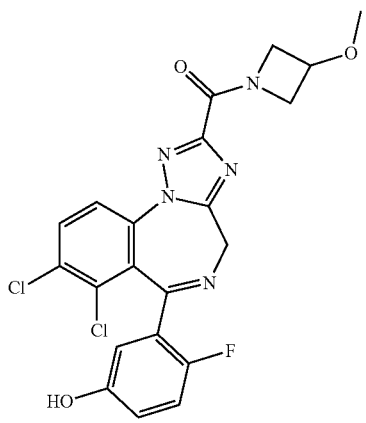 [SMILES: COC1CN(C(=O)c2nc3n(n2)-c2ccc(Cl)c(Cl)c2C(c2cc(O)ccc2F)=NC3)C1]

a) 1-amino-6,7-dichloro-5-(2-fluoro-5-methoxy-phenyl)-3H-1,4-benzodiazepin-2-one To a mixture of 6,7-dichloro-5-(2-fluoro-5-methoxy-phenyl)-1,3-dihydro-1,4-benzodiazepin-2-one (building block A, 350 mg, 0.991 mmol) in DMF (10 mL) was added cesium carbonate (327 mg, 1.00 mmol). The mixture was stirred at 25° C. for 0.5 h, then O-diphenylphosphinylhydroxylamine (255 mg, 1.09 mmol) was added. The mixture was stirred at 25° C. for an additional 4 h, then diluted with water, extracted with ethyl acetate, dried over sodium sulfate, filtered and concentrated in vacuo. The residue was purified by flash column chromatography (silica, petroleum ether/ethyl acetate 5:1 to 0:1) to afford the title compound (290 mg, 79%) as a yellow oil. MS: 368.1 ([{$^{35}$Cl, $^{35}$Cl}M+H]$^+$), 370.1 ([{$^{35}$Cl, $^{37}$Cl}M+H]$^+$), ESI pos.

b) ethyl 7,8-dichloro-6-(2-fluoro-5-methoxy-phenyl)-4H-[1,2,4]triazolo[1,5-a][1,4]benzodiazepine-2-carboxylate A mixture of 1-amino-6,7-dichloro-5-(2-fluoro-5-methoxy-phenyl)-3H-1,4-benzodiazepin-2-one (280 mg, 0.760 mmol) and ethyl 2-ethoxy-2-imino-acetate (105 mg, 0.720 mmol) in ethanol (10 mL) was stirred at reflux for 4 h, then warmed up to 100° C. and stirred for an additional 4 h. The mixture was cooled, then further ethyl 2-ethoxy-2-imino-acetate (105 mg, 0.720 mmol) was added and heating to reflux was continued for 16 h. This procedure was repeated three times to give half conversion as monitored by LCMS. The reaction mixture was cooled and concentrated in vacuo. The residue was purified by flash column chromatography (silica, petroleum ether/ethyl acetate 5:1 to 1:1) to afford the title compound (160 mg, 65%) as a yellow oil. MS: 449.0 ([{$^{35}$Cl, $^{35}$Cl}M+H]$^+$), 451.0 ([{$^{35}$Cl, $^{37}$Cl}M+H]$^+$), ESI pos.

c) 7,8-dichloro-6-(2-fluoro-5-methoxy-phenyl)-4H-[1,2,4]triazolo[1,5-a][1,4]benzodiazepine-2-carboxylic acid To a mixture of ethyl 7,8-dichloro-6-(2-fluoro-5-methoxy-phenyl)-4H-[1,2,4]triazolo[1,5-a][1,4]benzodiazepine-2-carboxylate (160 mg, 0.494 mmol) in ethanol (5 mL) was added dropwise aqueous NaOH (1 M, 1.0 mL, 1.0 mmol). The reaction mixture was stirred at 25° C. for 1 h. Aqueous HCl (1 M) was added slowly until pH 4-5. The formed suspension was filtered. The collected solid was washed with water and dried in high vacuo to afford the title compound (90 mg, 43%) as a white solid. MS: 421.0 ($[\{^{35}Cl, ^{35}Cl\}M+H]^+$), 423.0 ($[\{^{35}Cl, ^{37}Cl\}M+H]^+$), ESI pos.

d) [7,8-dichloro-6-(2-fluoro-5-methoxy-phenyl)-4H-[1,2,4]triazolo[1,5-a][1,4]benzodiazepin-2-yl]-(3-methoxyazetidin-1-yl)methanone To a solution of 3-methoxyazetidine hydrochloride (38 mg, 0.31 mmol) in DMF (5 mL) was added 7,8-dichloro-6-(2-fluoro-5-methoxy-phenyl)-4H-[1,2,4]triazolo[1,5-a][1,4]benzodiazepine-2-carboxylic acid (88 mg, 0.21 mmol), N,N-diisopropylethylamine (0.10 mL, 0.57 mmol) and $T_3P$ (50% in ethyl acetate, 1.0 mL, 1.7 mmol). The mixture was stirred at 25° C. for 2 h, then dissolved in water and extracted with ethyl acetate. The organic layer was washed with brine, dried over sodium sulfate, filtered and concentrated in vacuo. The residue (combined with another batch, 5 µmol scale) was purified by preparative HPLC (Phenomenex Gemini-NX C18, 3 µm, 75×30 mm, 0.1% trifluoroacetic acid in water/acetonitrile) to afford the title compound (35 mg, 33%) as a light yellow solid. MS: 490.1 ($[\{^{35}Cl, ^{35}Cl\}M+H]^+$), 492.1 ($[\{^{35}Cl, ^{37}Cl\}M+H]^+$), ESI pos.

e) [7,8-dichloro-6-(2-fluoro-5-hydroxy-phenyl)-4H-[1,2,4]triazolo[1,5-a][1,4]benzodiazepin-2-yl]-(3-methoxyazetidin-1-yl)methanone In analogy to experiment of example 1 b, [7,8-dichloro-6-(2-fluoro-5-methoxy-phenyl)-4H-[1,2,4]triazolo[1,5-a][1,4]benzodiazepin-2-yl]-(3-methoxyazetidin-1-yl)methanone was converted to the title compound (3.4 mg, 13%) which was obtained as a white solid. MS: 476.1 ($[\{^{35}Cl, ^{35}Cl\}M+H]^+$), 478.1 ($[\{^{35}Cl, ^{37}Cl\}M+H]^+$), ESI pos.

Example 8

6-chloro-5-(2-fluoro-5-hydroxy-phenyl)-1-methyl-7-(trifluoromethyl)-3H-1,4-benzodiazepin-2-one

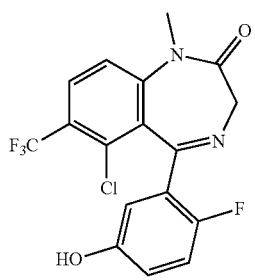 [SMILES: CN1C(=O)CN=C(c2cc(O)ccc2F)c2c1ccc(C(F)(F)F)c2Cl]

a) 6-chloro-5-(2-fluoro-5-methoxy-phenyl)-1-methyl-7-(trifluoromethyl)-3H-1,4-benzodiazepin-2-one In analogy to experiment of example 1 a, 6-chloro-5-(2-fluoro-5-methoxy-phenyl)-7-(trifluoromethyl)-1,3-dihydro-1,4-benzodiazepin-2-one (building block D) was converted into the title compound (142 mg, 86%) which was obtained as a yellow solid. MS: 401.2 ($[\{^{35}Cl\}M+H]^+$), 403.2 ($[\{^{37}Cl\}M+H]^+$), ESI pos.

b) 6-chloro-5-(2-fluoro-5-hydroxy-phenyl)-1-methyl-7-(trifluoromethyl)-3H-1,4-benzodiazepin-2-one In analogy to experiment of example 1 b, 6-chloro-5-(2-fluoro-5-methoxy-phenyl)-1-methyl-7-(trifluoromethyl)-3H-1,4-benzodiazepin-2-one was converted into the title compound (68 mg, 50%) which was obtained as a yellow solid. MS: 387.0 ($[\{^{35}Cl\}M+H]^+$), 389.0 ($[\{^{37}Cl\}M+H]^+$), ESI pos.

Example 9

3-[7-chloro-1-methyl-8-(trifluoromethyl)-4H-[1,2,4]triazolo[4,3-a][1,4]benzodiazepin-6-yl]-4-fluoro-phenol

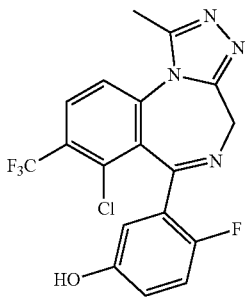 [SMILES: Cc1nnc2n1-c1ccc(C(F)(F)F)c(Cl)c1C(c1cc(O)ccc1F)=NC2]

a) 6-chloro-5-(2-fluoro-5-methoxy-phenyl)-7-(trifluoromethyl)-1,3-dihydro-1,4-benzodiazepine-2-thione In analogy to experiment of example 3 c, 6-chloro-5-(2-fluoro-5-methoxy-phenyl)-7-(trifluoromethyl)-1,3-dihydro-1,4-benzodiazepin-2-one (building block D) was converted into the title compound (290 mg, 62%) which was obtained as a yellow solid. MS: 403.0 ($[\{^{35}Cl\}M+H]^+$), 405.0 ($[\{^{37}Cl\}M+H]^+$), ESI pos.

b) 7-chloro-6-(2-fluoro-5-methoxy-phenyl)-1-methyl-8-(trifluoromethyl)-4H-[1,2,4]triazolo[4,3-a][1,4]benzodiazepine In analogy to experiment of example 3 d, 6-chloro-5-(2-fluoro-5-methoxy-phenyl)-7-(trifluoromethyl)-1,3-dihydro-1,4-benzodiazepine-2-thione was converted into the title compound (85 mg, 90%) which was obtained as a yellow oil. MS: 425.1 ($[\{^{35}Cl\}M+H]^+$), 427.1 ($[\{^{37}Cl\}M+H]^+$), ESI pos.

c) 3-[7-chloro-1-methyl-8-(trifluoromethyl)-4H-[1,2,4]triazolo[4,3-a][1,4]benzodiazepin-6-yl]-4-fluoro-phenol In analogy to experiment of example 1 b, 7-chloro-6-(2-fluoro-5-methoxy-phenyl)-1-methyl-8-(trifluoromethyl)-4H-[1,2,4]triazolo[4,3-a][1,4]benzodiazepine was converted into the title compound (10 mg, 12%) which was obtained as a yellow solid. MS: 411.1 ([{$^{35}$Cl}M+H]$^+$), 413.1 ([{$^{37}$Cl}M+H]$^+$), ESI pos.

Example 10

3-[7-chloro-8-(trifluoromethyl)-4H-[1,2,4]triazolo[4,3-a][1,4]benzodiazepin-6-yl]-4-fluoro-phenol

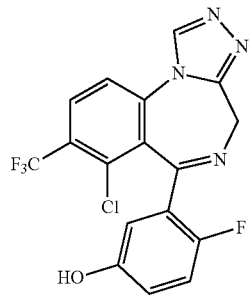 [SMILES: Oc1ccc(F)c(C2=NCc3nncn3-c3ccc(C(F)(F)F)c(Cl)c32)c1]

a) 7-chloro-6-(2-fluoro-5-methoxy-phenyl)-8-(trifluoromethyl)-4H-[1,2,4]triazolo[4,3-a][1,4]benzodiazepine In analogy to experiment of example 3 d, 6-chloro-5-(2-fluoro-5-methoxy-phenyl)-7-(trifluoromethyl)-1,3-dihydro-1,4-benzodiazepine-2-thione (example 9 a) using formic acid hydrazide instead of acethydrazide was converted into the title compound (74 mg, 81%) which was obtained as a yellow oil. MS: 411.0 ([{$^{35}$Cl}M+H]$^+$), 413.0 ([{$^{37}$Cl}M+H]$^+$), ESI pos.

b) 3-[7-chloro-8-(trifluoromethyl)-4H-[1,2,4]triazolo[4,3-a][1,4]benzodiazepin-6-yl]-4-fluoro-phenol In analogy to experiment of example 1 b, 7-chloro-6-(2-fluoro-5-methoxy-phenyl)-8-(trifluoromethyl)-4H-[1,2,4]triazolo[4,3-a][1,4]benzodiazepine was converted into the title compound (22 mg, 31%) which was obtained as a white solid. MS: 397.0 ([{$^{35}$Cl}M+H]$^+$), 399.0 ([{$^{37}$Cl}M+H]$^+$), ESI pos.

Example 11

8-chloro-7-(2-fluoro-5-hydroxy-phenyl)-9-(trifluoromethyl)-5H-pyrimido[1,2-a][1,4]benzodiazepin-3-one

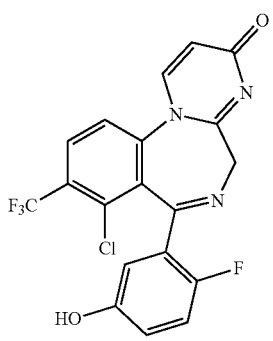 [SMILES: O=c1ccn2c(n1)CN=C(c1cc(O)ccc1F)c1c-2ccc(C(F)(F)F)c1Cl]

a) 6-chloro-5-(2-fluoro-5-methoxy-phenyl)-7-(trifluoromethyl)-3H-1,4-benzodiazepin-2-amine In analogy to experiment of example 5 a, 6-chloro-5-(2-fluoro-5-methoxy-phenyl)-7-(trifluoromethyl)-1,3-dihydro-1,4-benzodiazepine-2-thione was converted into the title compound (106 mg, quantitative) which was obtained as a yellow oil. This crude was used as such in the following step without further characterization.

b) 8-chloro-7-(2-fluoro-5-methoxy-phenyl)-9-(trifluoromethyl)-5H-pyrimido[1,2-a][1,4]benzodiazepin-3-one In analogy to experiment of example 5 b, 6-chloro-5-(2-fluoro-5-methoxy-phenyl)-7-(trifluoromethyl)-3H-1,4-benzodiazepin-2-amine was converted into the title compound (93 mg, 86%) which was obtained as a brown oil. MS: 438.1 ([{$^{35}$Cl}M+H]$^+$), 440.1 ([{$^{37}$Cl}M+H]$^+$), ESI pos.

c) 8-chloro-7-(2-fluoro-5-hydroxy-phenyl)-9-(trifluoromethyl)-5H-pyrimido[1,2-a][1,4]benzodiazepin-3-one In analogy to experiment of example 1 b, 8-chloro-7-(2-fluoro-5-methoxy-phenyl)-9-(trifluoromethyl)-5H-pyrimido[1,2-a][1,4]benzodiazepin-3-one was converted into the title compound (23 mg, 26%) which was obtained as a white solid. MS: 424.0 ([{$^{35}$Cl}M+H]$^+$), 426.0 ([{$^{37}$Cl}M+H]$^+$), ESI pos.

Example 12

6,7-dichloro-5-(2,6-difluoro-3-hydroxy-phenyl)-1-methyl-3H-1,4-benzodiazepin-2-one

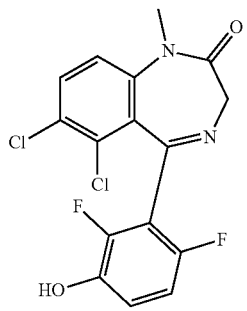 [SMILES: CN1C(=O)CN=C(c2c(F)ccc(O)c2F)c2c1ccc(Cl)c2Cl]

a) 6,7-dichloro-5-(2,6-difluoro-3-methoxy-phenyl)-1-methyl-3H-1,4-benzodiazepin-2-one In analogy to experiment of example 1 a, 6,7-dichloro-5-(2,6-difluoro-3-methoxy-phenyl)-1,3-dihydro-1,4-benzodiazepin-2-one (building block E) was converted into the title compound (50 mg, 48%) which was obtained as a light yellow oil. MS: 384.9 ([{$^{35}$Cl, $^{35}$Cl}M+H]$^+$), 386.9 ([{$^{35}$Cl, $^{37}$Cl}M+H]$^+$), ESI pos.

b) 6,7-dichloro-5-(2,6-difluoro-3-hydroxy-phenyl)-1-methyl-3H-1,4-benzodiazepin-2-one In analogy to experiment of example 1 b, 6,7-dichloro-5-(2,6-difluoro-3-methoxy-phenyl)-1-methyl-3H-1,4-benzodiazepin-2-one was converted into the title compound (26 mg, 54%) which was obtained as a yellow solid. MS: 370.9 ([{$^{35}$Cl, $^{35}$Cl}M+H]$^+$), 372.9 ([{$^{35}$Cl, $^{37}$Cl}M+H]$^+$), ESI pos.

Example 13

3-(7,8-dichloro-1-methyl-4H-[1,2,4]triazolo[4,3-a][1,4]benzodiazepin-6-yl)-2,4-difluoro-phenol

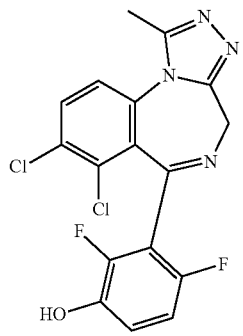 [SMILES: Cc1nnc2n1-c1ccc(Cl)c(Cl)c1C(c1c(F)ccc(O)c1F)=NC2]

a) 6,7-dichloro-5-(2,6-difluoro-3-methoxy-phenyl)-1,3-dihydro-1,4-benzodiazepine-2-thione In analogy to experiment of example 3 c, 6,7-dichloro-5-(2,6-difluoro-3-methoxy-phenyl)-1,3-dihydro-1,4-benzodiazepin-2-one (Building block E) was converted into the title compound (300 mg, 72%) which was obtained as a yellow solid. MS: 387.0 ([{$^{35}$Cl, $^{35}$Cl}M+H]$^+$), 389.0 ([{$^{35}$Cl, $^{37}$Cl}M+H]$^+$), ESI pos.

b) 7,8-dichloro-6-(2,6-difluoro-3-methoxy-phenyl)-1-methyl-4H-[1,2,4]triazolo[4,3-a][1,4]benzodiazepine In analogy to experiment of example 3 d, 6,7-dichloro-5-(2,6-difluoro-3-methoxy-phenyl)-1,3-dihydro-1,4-benzodiazepine-2-thione was converted into the title compound (77 mg, 73%) which was obtained as a light yellow solid. MS: 409.0 ([{$^{35}$Cl, $^{35}$Cl}M+H]$^+$), 411.0 ([{$^{35}$Cl, $^{37}$Cl}M+H]$^+$), ESI pos.

c) 3-(7,8-dichloro-1-methyl-4H-[1,2,4]triazolo[4,3-a][1,4]benzodiazepin-6-yl)-2,4-difluoro-phenol In analogy to experiment of example 1 b, 7,8-dichloro-6-(2,6-difluoro-3-methoxy-phenyl)-1-methyl-4H-[1,2,4]triazolo[4,3-a][1,4]benzodiazepine was converted into the title compound (28 mg, 40%) which was obtained as a white solid. MS: 394.9 ([{$^{35}$Cl, $^{35}$Cl}M+H]$^+$), 396.9 ([{$^{35}$Cl, $^{37}$Cl}M+H]$^+$), ESI pos.

Example 14

8,9-dichloro-7-(2,6-difluoro-3-hydroxy-phenyl)-5H-pyrimido[1,2-a][1,4]benzodiazepin-3-one

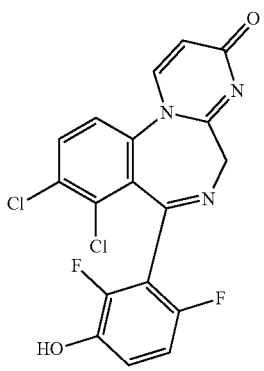 [SMILES: O=c1ccn2c(n1)CN=C(c1c(F)ccc(O)c1F)c1c-2ccc(Cl)c1Cl]

a) 6,7-dichloro-5-(2,6-difluoro-3-methoxy-phenyl)-3H-1,4-benzodiazepin-2-amine

In analogy to experiment of example 5 a, 6,7-dichloro-5-(2,6-difluoro-3-methoxy-phenyl)-1,3-dihydro-1,4-benzodiazepine-2-thione was converted into the title compound (210 mg, quantitative) which was obtained as a yellow solid. This crude material was used as such in the following step without further characterization.

c) 8,9-dichloro-7-(2,6-difluoro-3-methoxy-phenyl)-5H-pyrimido[1,2-a][1,4]benzodiazepin-3-one In analogy to experiment of example 5 b, 6,7-dichloro-5-(2,6-difluoro-3-methoxy-phenyl)-3H-1,4-benzodiazepin-2-amine was converted into the title compound (105 mg, 48%) which was obtained as a light yellow oil. MS: 422.0 ([{$^{35}$Cl, $^{35}$Cl}M+H]$^+$), 424.0 ([{$^{35}$Cl, $^{37}$Cl}M+H]$^+$), ESI pos.

d) 8,9-dichloro-7-(2,6-difluoro-3-hydroxy-phenyl)-5H-pyrimido[1,2-a][1,4]benzodiazepin-3-one In analogy to experiment of example 1 b, 8,9-dichloro-7-(2,6-difluoro-3-methoxy-phenyl)-5H-pyrimido[1,2-a][1,4]benzodiazepin-3-one was converted into the title compound (13 mg, 13%) which was obtained as a white solid. MS: 408.0 ([{$^{35}$Cl, $^{35}$Cl}M+H]$^+$), 410.0 ([{$^{35}$Cl, $^{37}$Cl}M+H]$^+$), ESI pos.

Example 15

[7-chloro-6-(2-fluoro-5-hydroxy-phenyl)-8-(trifluoromethyl)-4H-imidazo[1,5-a][1,4]benzodiazepin-3-yl]-(3-methoxyazetidin-1-yl)methanone

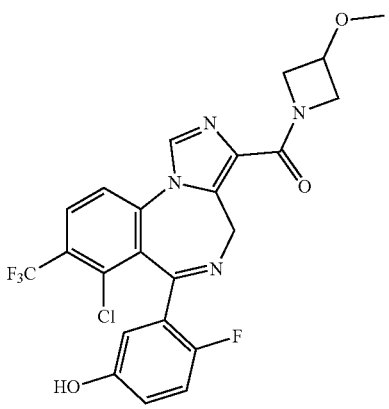 [SMILES: COC1CN(C(=O)c2ncn3c2CN=C(c2cc(O)ccc2F)c2c-3ccc(C(F)(F)F)c2Cl)C1]

a) methyl 7-chloro-6-(2-fluoro-5-methoxy-phenyl)-8-(trifluoromethyl)-4H-imidazo[1,5-a][1,4]benzodiazepine-3-carboxylate A solution of 6-chloro-5-(2-fluoro-5-methoxy-phenyl)-7-(trifluoromethyl)-1,3-dihydro-1,4-benzodiazepin-2-one (Building Block D, 100 mg, 0.259 mmol), dimethyl-p-toluidine (280 mg, 2.07 mmol) and phosphorus oxychloride (0.04 mL, 0.4 mmol) in DCE (5 mL) was stirred at 85° C. for 3 h. The reaction solution was cooled to room temperature, quenched with saturated aqueous NaHCO₃ and extracted with DCM. The organic layer was washed with water, dried over sodium sulfate, filtered and concentrated in vacuo. Meanwhile methyl isocyanoacetate (27 mg, 0.27 mmol) was added to a mixture of potassium tert-butoxide (29 mg, 0.26 mmol) in DMF (3 mL) at −30° C. and stirred for 5 min. Then the crude imidoyl chloride-intermediate described above was added to the reaction solution at −30° C. and stirred for another 30 min. The reaction mixture was warmed to room temperature and quenched with acetic acid. After stirring for 5 min the mixture was poured into ice-water, saturated with solid NaHCO₃ and extracted with ethyl acetate. The organic layer was dried over sodium sulfate, filtered and concentrated in vacuo. The residue was purified by flash column chromatography (silica, DCM/methanol 1:0 to 5:1) followed by preparative HPLC (Phenomenex Synergi C18, 10 µm, 150×25 mm, 0.1% trifluoroacetic acid in water/acetonitrile) to afford the title compound (23 mg, 19%) as a light yellow solid. MS: 468.1 ([{$^{35}$Cl}M+H]⁺), 470.1 ([{$^{37}$Cl}M+H]⁺), ESI pos.

b) 7-chloro-6-(2-fluoro-5-hydroxy-phenyl)-8-(trifluoromethyl)-4H-imidazo[1,5-a][1,4]benzodiazepine-3-carboxylic acid To a solution of methyl 7-chloro-6-(2-fluoro-5-methoxy-phenyl)-8-(trifluoromethyl)-4H-imidazo[1,5-a][1,4]benzodiazepine-3-carboxylate (23 mg, 0.050 mmol) in DCM (1 mL) was added boron tribromide (15 mg, 0.060 mmol). The mixture was stirred at 20° C. for 40 h. Additional boron tribromide (15 mg, 0.060 mmol) was added and stirring at 20° C. was continued for 16 h to complete conversion. The reaction mixture was quenched with ice water and concentrated in vacuo to afford the title compound (17 mg, 79%) as a yellow solid. This crude material was used as such in the next step without further characterisation.

c) [7-chloro-6-(2-fluoro-5-hydroxy-phenyl)-8-(trifluoromethyl)-4H-imidazo[1,5-a][1,4]benzodiazepin-3-yl]-(3-methoxyazetidin-1-yl)methanone To a solution of 3-methoxyazetidine hydrochloride (8.5 mg, 0.070 mmol) in DMF (2 mL) was added 7-chloro-6-(2-fluoro-5-hydroxy-phenyl)-8-(trifluoromethyl)-4H-imidazo[1,5-a][1,4]benzodiazepine-3-carboxylic acid (15 mg, 0.034 mmol), N,N-diisopropylethylamine (0.02 mL, 0.1 mmol) and T₃P (50% in ethyl acetate, 0.5 mL, 0.8 mmol). The mixture was stirred at 25° C. for 2 h. Additional 3-methoxyazetidine hydrochloride (8.5 mg, 0.070 mmol), N,N-diisopropylethylamine (0.02 mL, 0.1 mmol) and T₃P (50% in ethyl acetate, 0.5 mL, 0.8 mmol) were added. The reaction mixture was stirred at 25° C. for another 40 h, then (together with another batch, 5 µmol scale) was dissolved in water and extracted with ethyl acetate. The organic layer was washed with brine, dried over sodium sulfate, filtered and concentrated in vacuo. The residue was purified by preparative HPLC (Phenomenex Synergi C18, 10 µm, 150×25 mm, 0.1% trifluoroacetic acid in water/acetonitrile) followed by SFC (Daicel Chiralpak IC, 10 µm, 250×30 mm, 0.1% NH₄OH in methanol, 40%) to afford the title compound (3.1 mg, 16%) as a light yellow solid. MS: 509.1 ([{$^{35}$Cl}M+H]⁺), 511.1 ([{$^{37}$Cl}M+H]⁺), ESI pos.

Example 16

[7-chloro-6-(2-fluoro-5-hydroxy-phenyl)-8-(trifluoromethyl)-4H-[1,2,4]triazolo[1,5-a][1,4]benzodiazepin-2-yl]-(3-methoxyazetidin-1-yl)methanone

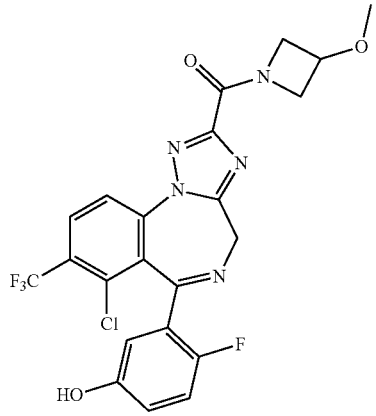 [SMILES: COC1CN(C(=O)c2nc3n(n2)-c2ccc(C(F)(F)F)c(Cl)c2C(c2cc(O)ccc2F)=NC3)C1]

a) 1-amino-6-chloro-5-(2-fluoro-5-methoxy-phenyl)-7-(trifluoromethyl)-3H-1,4-benzodiazepin-2-one In analogy to experiment of example 7 a, 6-chloro-5-(2-fluoro-5-methoxy-phenyl)-7-(trifluoromethyl)-1,3-dihydro-1,4-benzodiazepin-2-one (building block D) was converted into the title compound (264 mg, 74%) which was obtained as a yellow oil. MS: 402.2 ([{$^{35}$Cl}M+H]⁺), 404.2 ([{$^{37}$Cl}M+H]⁺), ESI pos.

b) ethyl 7-chloro-6-(2-fluoro-5-methoxy-phenyl)-8-(trifluoromethyl)-4H-[1,2,4]triazolo[1,5-a][1,4]benzodiazepine-2-carboxylate In analogy to experiment of example 7 b, 1-amino-6-chloro-5-(2-fluoro-5-methoxy-phenyl)-7-(trifluoromethyl)-3H-1,4-benzodiazepin-2-one was converted into the title compound (151 mg, 48%) which was obtained as a yellow oil. MS: 483.1 ([{$^{35}$Cl}M+H]$^+$), 485.1 ([{$^{37}$Cl}M+H]$^+$), ESI pos.

c) 7-chloro-6-(2-fluoro-5-hydroxy-phenyl)-8-(trifluoromethyl)-4H-[1,2,4]triazolo[1,5-a][1,4]benzodiazepine-2-carboxylic acid In analogy to experiment of example 15 b, ethyl 7-chloro-6-(2-fluoro-5-methoxy-phenyl)-8-(trifluoromethyl)-4H-[1,2,4]triazolo[1,5-a][1,4]benzodiazepine-2-carboxylate (149 mg, 0.309 mmol) was converted into the title compound (98 mg, 72%) which was obtained as a yellow solid. MS: 441.0 ([{$^{35}$Cl}M+H]$^+$), 443.0 ([{$^{37}$Cl}M+H]$^+$), ESI pos. This crude material was used as such for the next step without purification.

b) [7-chloro-6-(2-fluoro-5-hydroxy-phenyl)-8-(trifluoromethyl)-4H-[1,2,4]triazolo[1,5-a][1,4]benzodiazepin-2-yl]-(3-methoxyazetidin-1-yl)methanone In analogy to experiment of example 7 d, 7-chloro-6-(2-fluoro-5-hydroxy-phenyl)-8-(trifluoromethyl)-4H-[1,2,4]triazolo[1,5-a][1,4]benzodiazepine-2-carboxylic acid (98 mg, 0.22 mmol) using 3-methoxyazetidine hydrochloride was converted into the title compound (17.4 mg, 15%) which was obtained as a light yellow solid. MS: 510.1 ([{$^{35}$Cl}M+H]$^+$), 512.1 ([{$^{37}$Cl}M+H]$^+$), ESI pos.

Example 17

4-fluoro-3-[(4S)-7-chloro-1,4-dimethyl-8-(trifluoromethyl)-4H-[1,2,4]triazolo[4,3-a][1,4]benzodiazepin-6-yl]phenol

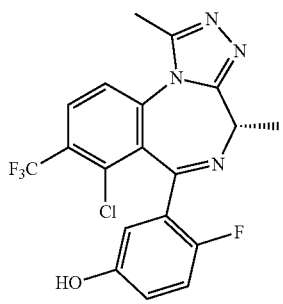 [SMILES: Cc1nnc2n1-c1ccc(C(F)(F)F)c(Cl)c1C(c1cc(O)ccc1F)=N[C@H]2C]

a) 6-chloro-5-(2-fluoro-5-methoxy-phenyl)-3-methyl-7-(trifluoromethyl)-1,3-dihydro-1,4-benzodiazepine-2-thione In analogy to experiment of example 3 c, 6-chloro-5-(2-fluoro-5-methoxy-phenyl)-3-methyl-7-(trifluoromethyl)-1,3-dihydro-1,4-benzodiazepin-2-one (building block F) was converted into the title compound (170 mg, 59%) which was obtained as a yellow solid. MS: 417.0 ([{$^{35}$Cl}M+H]$^+$), 419.0 ([{$^{37}$Cl}M+H]$^+$), ESI pos.

b) 7-chloro-6-(2-fluoro-5-methoxy-phenyl)-1,4-dimethyl-8-(trifluoromethyl)-4H-[1,2,4]triazolo[4,3-a][1,4]benzodiazepine In analogy to experiment of example 3 d, 6-chloro-5-(2-fluoro-5-methoxy-phenyl)-3-methyl-7-(trifluoromethyl)-1,3-dihydro-1,4-benzodiazepine-2-thione (160 mg, 0.384 mmol) was converted into the title compound (125 mg, 74%) which was obtained as a light yellow solid. MS: 439.0 ([{$^{35}$Cl}M+H]$^+$), 441.0 ([{$^{37}$Cl}M+H]$^+$), ESI pos.

c) 4-fluoro-3-[(4S)-7-chloro-1,4-dimethyl-8-(trifluoromethyl)-4H-[1,2,4]triazolo[4,3-a][1,4]benzodiazepin-6-yl]phenol In analogy to experiment of example 4 c, 7-chloro-6-(2-fluoro-5-methoxy-phenyl)-1,4-dimethyl-8-(trifluoromethyl)-4H-[1,2,4]triazolo[4,3-a][1,4]benzodiazepine was converted into the title compound (23 mg, 24%) which was obtained as a white solid. MS: 425.1 ([{$^{35}$Cl}M+H]$^+$), 427.1 ([{$^{37}$Cl}M+H]$^+$), ESI pos.

Example 18

(5S)-8,9-dichloro-7-(2,6-difluoro-3-hydroxy-phenyl)-5-methyl-5H-pyrimido[1,2-a][1,4]benzodiazepin-3-one

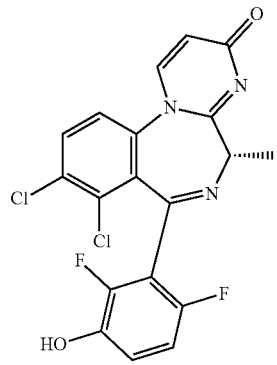 [SMILES: C[C@@H]1N=C(c2c(F)ccc(O)c2F)c2c(ccc(Cl)c2Cl)-n2ccc(=O)nc21]

a) 6,7-dichloro-5-(2,6-difluoro-3-methoxy-phenyl)-3-methyl-1,3-dihydro-1,4-benzodiazepine-2-thione In analogy to experiment of example 3 c, 6,7-dichloro-5-(2,6-difluoro-3-methoxy-phenyl)-3-methyl-1,3-dihydro-1,4-benzodiazepin-2-one (building block G) was converted into the title compound (680 mg, quantitative) which was obtained as a yellow solid. MS: 400.9 ([{$^{35}$Cl, $^{35}$Cl}M+H]$^+$), 402.9 ([{$^{35}$Cl, $^{37}$Cl}M+H]$^+$), ESI pos.

b) 6,7-dichloro-5-(2,6-difluoro-3-methoxy-phenyl)-3-methyl-3H-1,4-benzodiazepin-2-amine In analogy to experiment of example 5 a, 6,7-dichloro-5-(2,6-difluoro-3-methoxy-phenyl)-3-methyl-1,3-dihydro-1,4-benzodiazepine-2-thione was converted into the title compound (800 mg, quantitative) which was obtained as a yellow oil. This crude material was used as such in the next step without further characterisation.

c) 8,9-dichloro-7-(2,6-difluoro-3-methoxy-phenyl)-5-methyl-5H-pyrimido[1,2-a][1,4]benzodiazepin-3-one In analogy to experiment of example 5 b, 6,7-dichloro-5-(2,6-difluoro-3-methoxy-phenyl)-3-methyl-3H-1,4-benzodiazepin-2-amine was converted into the title compound (540 mg, 83%) which was obtained as a brown oil. MS: 435.9 ([{$^{35}$Cl, $^{35}$Cl}M+H]$^+$), 437.9 ([{$^{35}$Cl, $^{37}$Cl}M+H]$^+$), ESI pos.

d) (5S)-8,9-dichloro-7-(2,6-difluoro-3-hydroxy-phenyl)-5-methyl-5H-pyrimido[1,2-a][1,4]benzodiazepin-3-one In analogy to experiment of example 4 c, 8,9-dichloro-7-(2,6-difluoro-3-methoxy-phenyl)-5-methyl-5H-pyrimido [1,2-a][1,4]benzodiazepin-3-one was converted into the title compound (64 mg, 12%) as a light yellow solid. MS: 422.0 ([{$^{35}$Cl, $^{35}$Cl}M+H]$^+$), 424.0 ([{$^{35}$Cl, $^{37}$Cl}M+H]$^+$), ESI pos.

Example 19

2,4-difluoro-3-[(4S)-7,8-dichloro-1,4-dimethyl-4H-[1,2,4]triazolo[4,3-a][1,4]benzodiazepin-6-yl]phenol

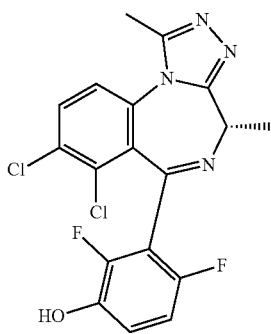 [SMILES: Cc1nnc2n1-c1ccc(Cl)c(Cl)c1C(c1c(F)ccc(O)c1F)=N[C@H]2C]

a) 7,8-dichloro-6-(2,6-difluoro-3-methoxy-phenyl)-1,4-dimethyl-4H-[1,2,4]triazolo[4,3-a][1,4]benzodiazepine In analogy to experiment of example 3 d, 6,7-dichloro-5-(2,6-difluoro-3-methoxy-phenyl)-3-methyl-1,3-dihydro-1,4-benzodiazepine-2-thione was converted into the title compound (220 mg, 67%) which was obtained as a light yellow solid. MS: 423.0 ([{$^{35}$Cl, $^{35}$Cl}M+H]$^+$), 425.0 ([{$^{35}$Cl, $^{37}$Cl}M+H]$^+$), ESI pos.

b) 2,4-difluoro-3-[(4S)-7,8-dichloro-1,4-dimethyl-4H-[1,2,4]triazolo[4,3-a][1,4]benzodiazepin-6-yl]phenol In analogy to experiment of example 4 c, 7,8-dichloro-6-(2,6-difluoro-3-methoxy-phenyl)-1,4-dimethyl-4H-[1,2,4]triazolo[4,3-a][1,4]benzodiazepine was converted into the title compound (39 mg, 19%) as a white solid. MS: 408.9 ([{$^{35}$Cl, $^{35}$Cl}M+H]$^+$), 410.9 ([{$^{35}$Cl, $^{37}$Cl}M+H]$^+$), ESI pos.

Example 20

6-[(4S)-7-chloro-1,4-dimethyl-8-(trifluoromethyl)-4H-[1,2,4]triazolo[4,3-a][1,4]benzodiazepin-6-yl]-5-fluoro-pyridin-2-ol

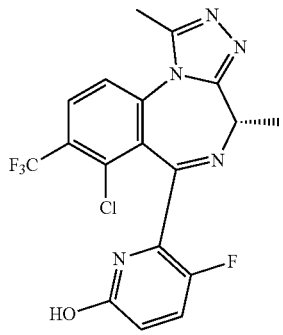

a) (4S)-7-chloro-6-(3-fluoro-6-methoxy-2-pyridyl)-1,4-dimethyl-8-(trifluoromethyl)-4H-[1,2,4]triazolo [4,3-a][1,4]benzodiazepine To a solution of (3S)-6-chloro-5-(3-fluoro-6-methoxy-2-pyridyl)-3-methyl-7-(trifluoromethyl)-1,3-dihydro-1,4-benzodiazepin-2-one (Building block H, 200 mg, 0.498 mmol) in tetrahydrofuran (10 mL) was added at 0° C. NaH (60% dispersion in mineral oil, 39.8 mg, 0.996 mmol) resulting in a light yellow suspension. After stirring for 10 min at 0° C. bis(2-oxo-3-oxazolidinyl)phosphinic chloride (253.5 mg, 0.996 mmol) was added and the reaction mixture was stirred at 0° C. for 2 h. Then acethydrazide (92.2 mg, 1.24 mmol) was added and the reaction mixture was stirred at room temperature for 60 min. More acethydrazide (92.2 mg, 1.24 mmol) was added and stirring continued at 50° C. for another 2 h resulting in a dark orange suspension. The reaction mixture was then diluted with 1,4-dioxane (10 mL) and stirred at 80° C. for 16 h, then quenched with water (10 mL) and extracted with ethyl acetate (2×30 mL). The organic layers were washed with water (30 mL) and brine (30 mL). The combined organic layers were dried over sodium sulfate, filtered and concentrated in vacuo. The residue was purified by flash column chromatography (silica, 0-50% ethyl acetate in heptane then 10% methanol in ethyl acetate) to afford the title compound (80 mg, 36%) as a colorless oil. MS: 440.1 ([{$^{35}$Cl}M+H]$^+$), 442.1 ([{$^{37}$Cl}M+H]$^+$), ESI pos.

b) 5-fluoro-6-[(4S)-7-chloro-1,4-dimethyl-8-(trifluoromethyl)-4H-[1,2,4]triazolo[4,3-a][1,4]benzodiazepin-6-yl]pyridin-2-ol In analogy to experiment of example 4 c, (4S)-7-chloro-6-(3-fluoro-6-methoxy-2-pyridyl)-1,4-dimethyl-8-(trifluoromethyl)-4H-[1,2,4]triazolo[4,3-a][1,4]benzodiazepine was converted into the enantiopure (+)-title compound (25 mg, 59%) which was obtained as an off-white solid. MS: 426.2 ([{$^{35}$Cl}M+H]$^+$), 428.2 ([{$^{37}$Cl}M+H]$^+$), ESI pos.

Example 21

[(4S)-7-chloro-6-(3-fluoro-6-hydroxy-2-pyridyl)-4-methyl-8-(trifluoromethyl)-4H-[1,2,4]triazolo[1,5-a][1,4]benzo diazepin-2-yl]-(3-fluoroazetidin-1-yl)methanone

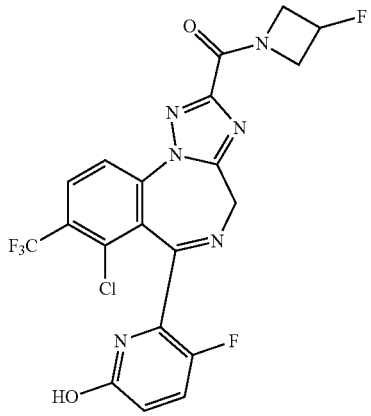 [SMILES: O=C(c1nc2n(n1)-c1ccc(C(F)(F)F)c(Cl)c1C(c1nc(O)ccc1F)=NC2)N1CC(F)C1]

a) (3S)-1-amino-6-chloro-5-(3-fluoro-6-methoxy-2-pyridyl)-3-methyl-7-(trifluoromethyl)-3H-1,4-benzodiazepin-2-one In analogy to experiment of example 7 a, (3S)-6-chloro-5-(3-fluoro-6-methoxy-2-pyridyl)-3-methyl-7-(trifluoromethyl)-1,3-dihydro-1,4-benzodiazepin-2-one (Building block H) was converted into the title compound (289 mg, 94%) which was obtained as a light yellow foam. MS: 417.2 ([{$^{35}$Cl}M+H]$^+$), 419.2 ([{$^{37}$Cl}M+H]$^+$), ESI pos.

b) ethyl (4S)-7-chloro-6-(3-fluoro-6-methoxy-2-pyridyl)-4-methyl-8-(trifluoromethyl)-4H-[1,2,4]triazolo[1,5-a][1,4]benzodiazepine-2-carboxylate In analogy to experiment of example 7 b, (3S)-1-amino-6-chloro-5-(3-fluoro-6-methoxy-2-pyridyl)-3-methyl-7-(trifluoromethyl)-3H-1,4-benzodiazepin-2-one was converted into the title compound (254 mg, 74%) which was obtained as a light yellow foam. MS: 498.3 ([{$^{35}$Cl}M+H]$^+$), 500.3 ([{$^{37}$Cl}M+H]$^+$), ESI pos.

c) (4S)-7-chloro-6-(3-fluoro-6-methoxy-2-pyridyl)-4-methyl-8-(trifluoromethyl)-4H-[1,2,4]triazolo[1,5-a][1,4]benzodiazepine-2-carboxylic acid In analogy to experiment of example 7 c, ethyl (4S)-7-chloro-6-(3-fluoro-6-methoxy-2-pyridyl)-4-methyl-8-(trifluoromethyl)-4H-[1,2,4]triazolo[1,5-a][1,4]benzodiazepine-2-carboxylate was converted into the title compound (242 mg, 95%) which was obtained as a white solid and was used as such in the following step without further purification. MS: 470.1 ([{$^{35}$Cl}M+H]$^+$), 472.1 ([{$^{37}$Cl}M+H]$^+$), ESI pos.

d) [(4S)-7-chloro-6-(3-fluoro-6-methoxy-2-pyridyl)-4-methyl-8-(trifluoromethyl)-4H-[1,2,4]triazolo[1,5-a][1,4]benzodiazepin-2-yl]-(3-fluoroazetidin-1-yl)methanone In analogy to experiment of example 7 d, (4S)-7-chloro-6-(3-fluoro-6-methoxy-2-pyridyl)-4-methyl-8-(trifluoromethyl)-4H-[1,2,4]triazolo[1,5-a][1,4]benzodiazepine-2-carboxylic acid using 3-fluoroazetidine hydrochloride and 1-propanephosphonic anhydride (50% in ethyl acetate) instead of T$_3$P was converted into the title compound (193 mg, 79%) which was obtained as a white foam. MS: 527.1 ([{$^{35}$Cl}M+H]$^+$), 529.1 ([{$^{37}$Cl}M+H]$^+$), ESI pos.

e) [(4S)-7-chloro-6-(3-fluoro-6-hydroxy-2-pyridyl)-4-methyl-8-(trifluoromethyl)-4H-[1,2,4]triazolo[1,5-a][1,4]benzodiazepin-2-yl]-(3-fluoroazetidin-1-yl)methanone In analogy to experiment of example 4 c, [(4S)-7-chloro-6-(3-fluoro-6-methoxy-2-pyridyl)-4-methyl-8-(trifluoromethyl)-4H-[1,2,4]triazolo[1,5-a][1,4]benzodiazepin-2-yl]-(3-fluoroazetidin-1-yl)methanone was converted into the enantiopure title compound (3 mg, 38%) which was obtained as a colorless oil. MS: 513.3 ([{$^{35}$Cl}M+H]$^+$), 515.3 ([{$^{37}$Cl}M+H]$^+$), ESI pos.

Example 22

5-chloro-6-[(4S)-7-chloro-1,4-dimethyl-8-(trifluoromethyl)-4H-[1,2,4]triazolo[4,3-a][1,4]benzodiazepin-6-yl]pyridin-2-ol

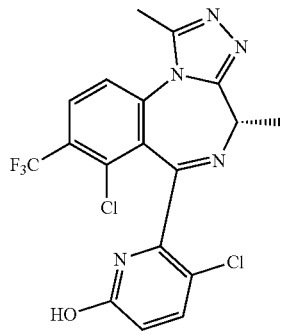 [SMILES: Cc1nnc2n1-c1ccc(C(F)(F)F)c(Cl)c1C(c1nc(O)ccc1Cl)=N[C@H]2C]

a) (4S)-7-chloro-6-(3-chloro-6-methoxy-2-pyridyl)-1,4-dimethyl-8-(trifluoromethyl)-4H-[1,2,4]triazolo[4,3-a][1,4]benzodiazepine In analogy to experiment of example 20 a, (3S)-6-chloro-5-(3-chloro-6-methoxy-2-pyridyl)-3-methyl-7-(trifluoromethyl)-1,3-dihydro-1,4-benzodiazepin-2-one (Building block I) was converted into the title compound (61 mg, 36%) which was obtained as a light yellow foam. MS: 456.1 ([{$^{35}$Cl, $^{35}$Cl}M+H]$^+$), 458.1 ([{$^{35}$Cl, $^{37}$Cl}M+H]$^+$), ESI pos.

b) 5-chloro-6-[(4S)-7-chloro-1,4-dimethyl-8-(trifluoromethyl)-4H-[1,2,4]triazolo[4,3-a][1,4]benzodiazepin-6-yl]pyridin-2-ol In analogy to experiment of example 4 c, (4S)-7-chloro-6-(3-chloro-6-methoxy-2-pyridyl)-1,4-dimethyl-8-(trifluoromethyl)-4H-[1,2,4]triazolo[4,3-a][1,4]benzodiazepine was converted into the enantiopure (+)-title compound (18 mg, 56%) which was obtained as a light yellow foam. MS: 442.2 ([{$^{35}$Cl}M+H]$^+$), 444.2 ([{$^{37}$Cl}M+H]$^+$), ESI pos.

Example 23

6-[(4S)-7-chloro-1,4-dimethyl-8-(trifluoromethyl)-4H-imidazo[1,2-a][1,4]benzodiazepin-6-yl]-5-fluoro-pyridin-2-ol

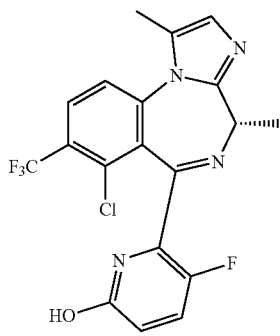

a) (3S)-5-(6-benzyloxy-3-fluoro-2-pyridyl)-6-chloro-3-methyl-7-(trifluoromethyl)-1,3-dihydro-1,4-benzodiazepine-2-thione In analogy to experiment of example 3 c, (3S)-5-(6-benzoxy-3-fluoro-2-pyridyl)-6-chloro-3-methyl-7-(trifluoromethyl)-1,3-dihydro-1,4-benzodiazepin-2-one (Building block J) was converted into the title compound (478 mg, 81%) which was obtained as a yellow solid. MS: 494.2 ([{$^{35}$Cl}M+H]$^+$), 496.2 ([{$^{37}$Cl}M+H]$^+$), ESI pos.

b) (3S)-5-(6-benzyloxy-3-fluoro-2-pyridyl)-6-chloro-3-methyl-7-(trifluoromethyl)-1,3-dihydro-1,4-benzodiazepin-2-imine In analogy to experiment of example 5 a, (3S)-5-(6-benzyloxy-3-fluoro-2-pyridyl)-6-chloro-3-methyl-7-(trifluoromethyl)-1,3-dihydro-1,4-benzodiazepine-2-thione was converted into the title compound (165 mg, 84%) which was obtained as a brown oil. MS: 477.3 ([{$^{35}$Cl}M+H]$^+$), 479.2 ([{$^{37}$Cl}M+H]$^+$), ESI pos.

c) (4S)-6-(6-benzyloxy-3-fluoro-2-pyridyl)-7-chloro-1,4-dimethyl-8-(trifluoromethyl)-4H-imidazo[1,2-a][1,4]benzodiazepine To a solution of (3S)-5-(6-benzyloxy-3-fluoro-2-pyridyl)-6-chloro-3-methyl-7-(trifluoromethyl)-1,3-dihydro-1,4-benzodiazepin-2-imine (103 mg, 0.247 mmol) in 1-butanol (3 mL) was added at room temperature propargylamine (108.8 mg, 0.126 mL, 1.98 mmol) and p-toluenesulfonic acid monohydrate (9.4 mg, 0.049 mmol). The reaction mixture was stirred in a sealed tube at 120° C. for 4 h, then concentrated in vacuo. The residue was diluted with DCM and washed with saturated aqueous NaHCO$_3$. The organic layer was dried over sodium sulfate and concentrated in vacuo. The residue was purified by flash column chromatography (silica, 1% methanol in DCM) to afford the title compound (137 mg, 73%) as an orange oil. MS: 515.3 ([{$^{35}$Cl}M+H]$^+$), 517.3 ([{$^{37}$Cl}M+H]$^+$), ESI pos.

d) 6-[(4S)-7-chloro-1,4-dimethyl-8-(trifluoromethyl)-4H-imidazo[1,2-a][1,4]benzodiazepin-6-yl]-5-fluoro-pyridin-2-ol To a solution of (4S)-6-(6-benzyloxy-3-fluoro-2-pyridyl)-7-chloro-1,4-dimethyl-8-(trifluoromethyl)-4H-imidazo[1,2-a][1,4]benzodiazepine (137 mg, 0.253 mmol) in dichloromethane (7 ml) at 25° C. was added N,N-dimethylaniline (612.6 mg, 0.64 mL, 5.06 mmol) dropwise and aluminium chloride (505.6 mg, 3.79 mmol) in one portion. The reaction mixture was stirred at room temperature for 1 h, then filtered through a pad of celite and washed with MeOH/DCM 1:1. The filtrate was concentrated in vacuo. The residue was partionated between Dublecco's Phosphate Buffered and DCM. The aqueous phase was extracted twice with DCM. The combined organic layers were washed with brine, dried over Na$_2$SO$_4$ and concentrated in vacuo. The residue was purified by flash column chromatography (silica gel, 0-100% ethyl acetate in heptane, then 0-5% methanol in ethyl acetate), then by chiral SFC (Daicel Chiralcel OJ-H, 15% methanol) to afford the enantiopure (+)-title compound (17 mg, 33%) as a light yellow solid. MS: 425.2 ([{$^{35}$Cl}M+H]$^+$), 427.2 ([{$^{37}$Cl}M+H]$^+$), ESI pos.

Example 24

6-[(10S)-6-chloro-10-methyl-5-(trifluoromethyl)-1,9,12-triazatetracyclo[9.6.0.0.2,7.0.13,17]heptadeca-2(7),3,5,8,11,13(17)-hexaen-8-yl]-5-fluoro-pyridin-2-ol

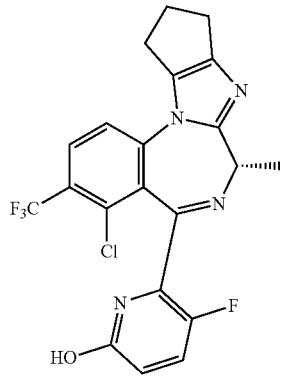 [SMILES: C[C@@H]1N=C(c2nc(O)ccc2F)c2c(ccc(C(F)(F)F)c2Cl)-n2c1nc1c2CCC1]

a) (1S)-2-[(E/Z)-[(3S)-5-(6-benzyloxy-3-fluoro-2-pyridyl)-6-chloro-3-methyl-7-(trifluoromethyl)-1,3-dihydro-1,4-benzodiazepin-2-ylidene]amino]cyclopentanol To a mixture of (3S)-5-(6-benzyloxy-3-fluoro-2-pyridyl)-6-chloro-3-methyl-7-(trifluoromethyl)-1,3-dihydro-1,4-benzodiazepine-2-thione (example 23 a, 455 mg, 0.737 mmol) in ethanol (5.4 mL) and water (2.7 mL) was added sodium carbonate (242 mg, 2.28 mmol) followed by trans-2-aminocyclopentanol hydrochloride (305 mg, 2.22 mmol). The reaction mixture was stirred at 80° C. overnight, cooled to room temperature and concentrated in vacuo. The residue was partitioned between ethyl acetate (60 mL) and water (10 mL). The aqueous layer was extracted with ethyl acetate (60 mL). The combined organic layers were washed with brine (10 mL), dried over sodium sulfate, filtered and concentrated in vacuo. The residue was purified by flash column chromatography (silica, 0-50% ethyl acetate in heptane) to afford the title compound (300 mg, 69%) as an off-white foam. MS: 561.3 ([{$^{35}$Cl}M+H]$^+$), 563.2 ([{$^{37}$Cl}M+H]$^+$), ESI pos.

b) (10S)-8-(6-benzyloxy-3-fluoro-2-pyridyl)-6-chloro-10-methyl-5-(trifluoromethyl)-1,9,12-triazatetracyclo[9.6.0.02,7.013,17]heptadeca-2(7),3,5,8,11,13(17)-hexaene To a solution of (1S)-2-[(E/Z)-[(3S)-5-(6-benzyloxy-3-fluoro-2-pyridyl)-6-chloro-3-methyl-7-(trifluoromethyl)-1,3-dihydro-1,4-benzodiazepin-2-ylidene]amino]cyclopentanol (296 mg, 0.501 mmol) in dichloromethane (3.6 mL) at 0° C. was added Dess-Martin periodinane (256 mg, 0.604 mmol). The reaction mixture was stirred at 0° C. for 1.5 h. Another portion of Dess-Martin periodinane (255 mg, 0.602 mmol) was added at 0° C. The reaction mixture was stirred at room temperature for 2.5 h, then quenched with saturated aqueous NaHCO$_3$ (5 mL) and aqueous Na$_2$S$_2$O$_3$ (5 mL) and stirred vigorously for 15 min at room temperature. The biphasic mixture was then extracted with dichloromethane (2×60 mL). The combined organic layers were washed with saturated aqueous NaHCO$_3$ (10 mL), dried over sodium sulfate, filtered and concentrated in vacuo. The residue was adsorbed on ISOLUTE HM-N and purified by flash column chromatography (silica, 0-5% methanol in dichloromethane) to afford the title compound (134 mg, 49%) as a light yellow oil. MS: 541.2 ([{$^{35}$Cl}M+H]$^+$), 543.2 ([{$^{37}$Cl}M+H]$^+$), ESI pos.

c) 6-[(10S)-6-chloro-10-methyl-5-(trifluoromethyl)-1,9,12-triazatetracyclo[9.6.0.02,7.013,17]heptadeca-2(7),3,5,8,11,13(17)-hexaen-8-yl]-5-fluoro-pyridin-2-ol In analogy to experiment of example 23 d, (10S)-8-(6-benzyloxy-3-fluoro-2-pyridyl)-6-chloro-10-methyl-5-(trifluoromethyl)-1,9,12-triazatetracyclo[9.6.0.02,7.013,17]heptadeca-2(7),3,5,8,11,13(17)-hexaene was converted into the enantiopure (+)-title compound (19 mg, 46%) which was obtained as a brown foam. MS: 451.2 ([{$^{35}$Cl}M+H]$^+$), 453.2 ([{$^{37}$Cl}M+H]$^+$), ESI pos.

Example 25

6-[(4S)-7-chloro-2,4-dimethyl-8-(trifluoromethyl)-4H-[1,2,4]triazolo[1,5-a][1,4]benzodiazepin-6-yl]-5-fluoro-pyridin-2-ol

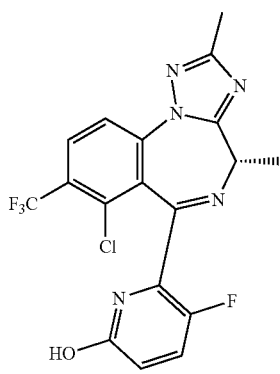 [SMILES: Cc1nc2n(n1)-c1ccc(C(F)(F)F)c(Cl)c1C(c1nc(O)ccc1F)=N[C@H]2C]

a) (3S)-1-amino-5-(6-benzyloxy-3-fluoro-2-pyridyl)-6-chloro-3-methyl-7-(trifluoromethyl)-3H-1,4-benzodiazepin-2-one In analogy to experiment of example 7 a, (3S)-5-(6-benzoxy-3-fluoro-2-pyridyl)-6-chloro-3-methyl-7-(trifluoromethyl)-1,3-dihydro-1,4-benzodiazepin-2-one (Building block J) was converted into the title compound (817 mg, 85%) which was obtained as a yellow foam. MS: 493.3 ([{$^{35}$Cl}M+H]$^+$), 495.2 ([{$^{37}$Cl}M+H]$^+$), ESI pos.

b) (4S)-6-(6-benzyloxy-3-fluoro-2-pyridyl)-7-chloro-2,4-dimethyl-8-(trifluoromethyl)-4H-[1,2,4]triazolo[1,5-a][1,4]benzodiazepine In analogy to experiment of example 7 b, (3S)-1-amino-5-(6-benzyloxy-3-fluoro-2-pyridyl)-6-chloro-3-methyl-7-(trifluoromethyl)-3H-1,4-benzodiazepin-2-one using ethyl acetimidate hydrochloride instead of ethyl 2-ethoxy-2-imino-acetate was converted into the title compound (617 mg, 58%) which was obtained as a light yellow waxy solid. MS: 516.3 ([{$^{35}$Cl}M+H]$^+$), 518.3 ([{$^{37}$Cl}M+H]$^+$), ESI pos.

c) 6-[(4S)-7-chloro-2,4-dimethyl-8-(trifluoromethyl)-4H-[1,2,4]triazolo[1,5-a][1,4]benzodiazepin-6-yl]-5-fluoro-pyridin-2-ol In analogy to experiment of example 23 d, (4S)-6-(6-benzyloxy-3-fluoro-2-pyridyl)-7-chloro-2,4-dimethyl-8-(trifluoromethyl)-4H-[1,2,4]triazolo[1,5-a][1,4]benzodiazepine was converted into the enantiopure (+)-title compound (83 mg, 42%) which was obtained as a light yellow solid. MS: 426.2 ([{$^{35}$Cl}M+H]$^+$), 428.2 ([{$^{37}$Cl}M+H]$^+$), ESI pos.

Example 26

5-chloro-6-[(4S)-7-chloro-1,4-dimethyl-8-(trifluoromethyl)-4H-imidazo[1,2-a][1,4]benzodiazepin-6-yl]pyridin-2-ol

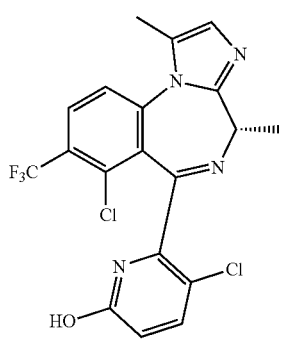 [SMILES: Cc1cnc2n1-c1ccc(C(F)(F)F)c(Cl)c1C(c1nc(O)ccc1Cl)=N[C@H]2C]

a) (3S)-6-chloro-5-(3-chloro-6-methoxy-2-pyridyl)-3-methyl-7-(trifluoromethyl)-1,3-dihydro-1,4-benzodiazepine-2-thione In analogy to experiment of example 3 c, (3S)-6-chloro-5-(3-chloro-6-methoxy-2-pyridyl)-3-methyl-7-(trifluoromethyl)-1,3-dihydro-1,4-benzodiazepin-2-one (Building block I) was converted into the title compound (531 mg, 74%) which was obtained as a yellow solid. MS: 434.2 ([{$^{35}$Cl, $^{35}$Cl}M+H]$^+$), 436.2 ([{$^{35}$Cl, $^{37}$Cl}M+H]$^+$), ESI pos.

b) (3S)-6-chloro-5-(3-chloro-6-methoxy-2-pyridyl)-3-methyl-7-(trifluoromethyl)-1,3-dihydro-1,4-benzodiazepin-2-imine In analogy to experiment of example 5 a, (3S)-6-chloro-5-(3-chloro-6-methoxy-2-pyridyl)-3-methyl-7-(trifluoromethyl)-1,3-dihydro-1,4-benzodiazepine-2-thione was converted into the title compound (541 mg, 94%) which was obtained as a yellow foam. MS: 417.2 ([{$^{35}$Cl, $^{35}$Cl}M+H]$^+$), 419.2 ([{$^{35}$Cl, $^{37}$Cl}M+H]$^+$), ESI pos.

c) (4S)-7-chloro-6-(3-chloro-6-methoxy-2-pyridyl)-1,4-dimethyl-8-(trifluoromethyl)-4H-imidazo[1,2-a][1,4]benzodiazepine In analogy to experiment of example 23 c, (3S)-6-chloro-5-(3-chloro-6-methoxy-2-pyridyl)-3-methyl-7-(trifluoromethyl)-1,3-dihydro-1,4-benzodiazepin-2-imine was converted into the title compound (389 mg, 70%) which was obtained as a light yellow foam. MS: 455.2 ([{$^{35}$Cl, $^{35}$Cl}M+H]$^+$), 457.2 ([{$^{35}$Cl, $^{37}$Cl}M+H]$^+$), ESI pos.

d) 5-chloro-6-[(4S)-7-chloro-1,4-dimethyl-8-(trifluoromethyl)-4H-imidazo[1,2-a][1,4]benzodiazepin-6-yl]pyridin-2-ol In analogy to experiment of example 23 d, (4S)-7-chloro-6-(3-chloro-6-methoxy-2-pyridyl)-1,4-dimethyl-8-(trifluoromethyl)-4H-imidazo[1,2-a][1,4]benzodiazepine was converted into the enantiopure (+)-title compound (132 mg, 44%) which was obtained as a light brown foam. MS: 441.2 ([{$^{35}$Cl}M+H]$^+$), 443.2 ([{$^{37}$Cl}M+H]$^+$), ESI pos.

Example 27

5-chloro-6-[(4S)-7-chloro-2,4-dimethyl-8-(trifluoromethyl)-4H-imidazo[1,2-a][1,4]benzodiazepin-6-yl]pyridin-2-ol

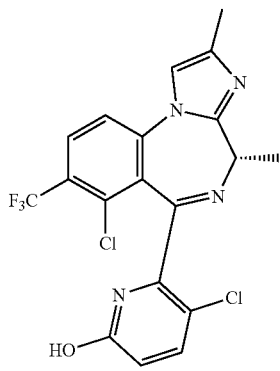 [SMILES: Cc1cn2c(n1)[C@H](C)N=C(c1nc(O)ccc1Cl)c1c-2ccc(C(F)(F)F)c1Cl]

a) 2-[(E/Z)-[(3S)-6-chloro-5-(3-chloro-6-methoxy-2-pyridyl)-3-methyl-7-(trifluoromethyl)-1,3-dihydro-1,4-benzodiazepin-2-ylidene]amino]propan-1-ol To a solution of (3S)-6-chloro-5-(3-chloro-6-methoxy-2-pyridyl)-3-methyl-7-(trifluoromethyl)-1,3-dihydro-1,4-benzodiazepin-2-one (Building block I, 203 mg, 0.485 mmol) in tetrahydrofuran (9.7 mL) was added at 0° C. sodium hydride (60% dispersion in mineral oil, 58.3 mg, 1.46 mmol). After stirring for 10 min at 10° C. bis(2-oxo-3-oxazolidinyl) phosphinic chloride (247.1 mg, 0.97 mmol) was added and the reaction mixture was stirred at 0° C. for 2 h. Then dl-alaninol (182 mg, 0.19 mL, 2.43 mmol) was added and the reaction mixture was stirred at 23° C. for 1 h, then quenched with water and aqueous NH$_4$Cl (20 mL) and extracted with ethyl acetate (2×60 mL). The combined organic layers were washed with water (30 mL) and brine (30 mL), dried over sodium sulfate, filtered and concentrated in vacuo. The residue was purified by flash column chromatography (silica, 0-50% ethyl acetate in heptane, then 0-10% methanol in ethyl acetate) to afford the title compound (91 mg, 38%) as a light yellow oil. MS: 475.1 ([{$^{35}$Cl, $^{35}$Cl}M+H]$^+$), 477.1 ([{$^{35}$Cl, $^{37}$Cl}M+H]$^+$), ESI pos.

b) (4S)-7-chloro-6-(3-chloro-6-methoxy-2-pyridyl)-2,4-dimethyl-8-(trifluoromethyl)-4H-imidazo[1,2-a][1,4]benzodiazepine In analogy to experiment of example 24 b, 2-[(E/Z)-[(3S)-6-chloro-5-(3-chloro-6-methoxy-2-pyridyl)-3-methyl-7-(trifluoromethyl)-1,3-dihydro-1,4-benzodiazepin-2-ylidene]amino]propan-1-ol was converted into the title compound (77 mg, 86%) which was obtained as a light yellow oil. MS: 455.1 ([{$^{35}$Cl, $^{35}$Cl}M+H]$^+$), 457.1 ([{$^{35}$Cl, $^{37}$Cl}M+H]$^+$), ESI pos.

c) 5-chloro-6-[(4S)-7-chloro-2,4-dimethyl-8-(trifluoromethyl)-4H-imidazo[1,2-a][1,4]benzodiazepin-6-yl]pyridin-2-ol In analogy to experiment of example 4 c, (4S)-7-chloro-6-(3-chloro-6-methoxy-2-pyridyl)-2,4-dimethyl-8-(trifluoromethyl)-4H-imidazo[1,2-a][1,4]benzodiazepine was converted into the enantiopure (−)-title compound (13 mg, 44%) which was obtained as a white solid. MS: 441.2 ([{$^{35}$Cl}M+H]$^+$), 443.1 ([{$^{37}$Cl}M+H]$^+$), ESI pos.

Example 28

6-[(4S)-7-chloro-2,4-dimethyl-8-(trifluoromethyl)-4H-imidazo[1,2-a][1,4]benzodiazepin-6-yl]-5-fluoro-pyridin-2-ol

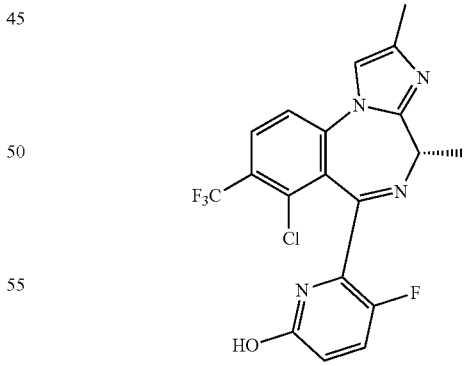

a) 2-[(E/Z)-[(3S)-5-(6-benzyloxy-3-fluoro-2-pyridyl)-6-chloro-3-methyl-7-(trifluoromethyl)-1,3-dihydro-1,4-benzodiazepin-2-ylidene]amino]propan-1-ol In analogy to experiment of example 27 a, (3S)-5-(6-benzoxy-3-fluoro-2-pyridyl)-6-chloro-3-methyl-7-(trifluoromethyl)-1,3-dihydro-1,4-benzodiazepin-2-one (Building block J) was converted into the title compound (269 mg, 40%) which was obtained as an orange foam. MS: 535.3 ([{$^{35}$Cl}M+H]$^+$), 537.3 ([{$^{37}$Cl}M+H]$^+$), ESI pos.

b) (4S)-6-(6-benzyloxy-3-fluoro-2-pyridyl)-7-chloro-2,4-dimethyl-8-(trifluoromethyl)-4H-imidazo[1,2-a][1,4]benzodiazepine In analogy to experiment of example 24 b, 2-[(E/Z)-[(3S)-5-(6-benzyloxy-3-fluoro-2-pyridyl)-6-chloro-3-methyl-7-(trifluoromethyl)-1,3-dihydro-1,4-benzodiazepin-2-ylidene]amino]propan-1-ol was converted into the title compound (154 mg, 59%) which was obtained as a light yellow foam. MS: 515.4 ([{$^{35}$Cl}M+H]$^+$), 517.3 ([{$^{37}$Cl}M+H]$^+$), ESI pos.

c) 6-[(4S)-7-chloro-2,4-dimethyl-8-(trifluoromethyl)-4H-imidazo[1,2-a][1,4]benzodiazepin-6-yl]-5-fluoro-pyridin-2-ol In analogy to experiment of example 4 c, (4S)-6-(6-benzyloxy-3-fluoro-2-pyridyl)-7-chloro-2,4-dimethyl-8-(trifluoromethyl)-4H-imidazo[1,2-a][1,4]benzodiazepine was converted into the enantiopure (+)-title compound (75 mg, 47%) which was obtained as a light brown solid. MS: 425.3 ([{$^{35}$Cl}M+H]$^+$), 427.2 ([{$^{37}$Cl}M+H]$^+$), ESI pos.

Example 29

5-chloro-6-[(4S)-7-chloro-2,4-dimethyl-8-(trifluoromethyl)-4H-[1,2,4]triazolo[1,5-a][1,4]benzodiazepin-6-yl]pyridin-2-ol

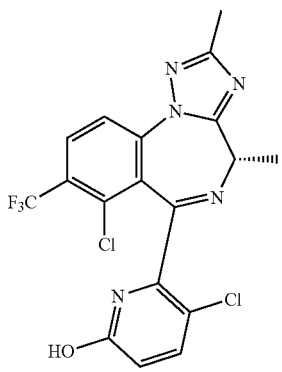 [SMILES: Cc1nc2n(n1)-c1ccc(C(F)(F)F)c(Cl)c1C(c1nc(O)ccc1Cl)=N[C@H]2C]

a) (3S)-1-amino-6-chloro-5-(3-chloro-6-methoxy-2-pyridyl)-3-methyl-7-(trifluoromethyl)-3H-1,4-benzodiazepin-2-one In analogy to experiment of example 7 a, (3S)-6-chloro-5-(3-chloro-6-methoxy-2-pyridyl)-3-methyl-7-(trifluoromethyl)-1,3-dihydro-1,4-benzodiazepin-2-one (Building block I) was converted into the title compound (267 mg, 91%) which was obtained as a white foam. MS: 433.2 ([{$^{35}$Cl, $^{35}$Cl}M+H]$^+$), 435.1 ([{$^{35}$Cl, $^{37}$Cl}M+H]$^+$), ESI pos.

b) (4S)-7-chloro-6-(3-chloro-6-methoxy-2-pyridyl)-2,4-dimethyl-8-(trifluoromethyl)-4H-[1,2,4]triazolo[1,5-a][1,4]benzodiazepine In analogy to experiment of example 7 b, (3S)-1-amino-6-chloro-5-(3-chloro-6-methoxy-2-pyridyl)-3-methyl-7-(tri-fluoromethyl)-3H-1,4-benzodiazepin-2-one was converted into the title compound (193 mg, 67%) which was obtained as a white foam. MS: 456.1 ([{$^{35}$Cl, $^{35}$Cl}M+H]$^+$), 458.1 ([{$^{35}$Cl, $^{37}$Cl}M+H]$^+$), ESI pos.

c) 5-chloro-6-[(4S)-7-chloro-2,4-dimethyl-8-(trifluoromethyl)-4H-[1,2,4]triazolo[1,5-a][1,4]benzodiazepin-6-yl]pyridin-2-ol In analogy to experiment of example 23 d, (4S)-7-chloro-6-(3-chloro-6-methoxy-2-pyridyl)-2,4-dimethyl-8-(trifluoromethyl)-4H-[1,2,4]triazolo[1,5-a][1,4]benzodiazepine was converted into the enantiopure (+)-title compound (32 mg, 44%) which was obtained as a light brown foam. MS: 442.1 ([{$^{35}$Cl}M+H]$^+$), 444.1 ([{$^{37}$Cl}M+H]$^+$), ESI pos.

Example 30 azetidin-1-yl-[(4S)-7-chloro-6-(3-fluoro-6-hydroxy-2-pyridyl)-4-methyl-8-(trifluoromethyl)-4H-imidazo[1,2-a][1,4]benzodiazepin-2-yl]methanone

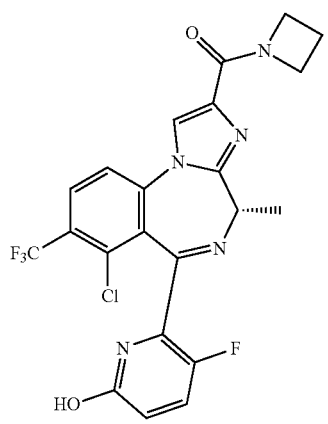 [SMILES: C[C@@H]1N=C(c2nc(O)ccc2F)c2c(ccc(C(F)(F)F)c2Cl)-n2cc(C(=O)N3CCC3)nc21]

a) 3-[(3S)-5-(6-benzyloxy-3-fluoro-2-pyridyl)-6-chloro-2-imino-3-methyl-7-(trifluoromethyl)-3H-1,4-benzodiazepin-1-yl]-2-oxo-propanoic acid A mixture of (3S)-5-(6-benzyloxy-3-fluoro-2-pyridyl)-6-chloro-3-methyl-7-(trifluoromethyl)-1,3-dihydro-1,4-benzodiazepin-2-imine (473 mg, 0.893 mmol), K$_2$CO$_3$ (370.2 mg, 2.68 mmol) and ethyl bromopyruvate (580.3 mg, 0.374 mL, 2.68 mmol) was stirred at room temperature for 3 d. The reaction mixture was concentrated in vacuo to afford. The residue was heated in ethanol (1 mL) for 4 h at 90° C., then concentrated in vacuo to afford the title compound (0.8 g, 78%) as a dark brown viscous oil. MS: 561.2 ([{$^{35}$Cl}M−H]$^+$), 563.1 ([{$^{37}$Cl}M−H]$^+$), ESI neg.

b) azetidin-1-yl-[(4S)-6-(6-benzyloxy-3-fluoro-2-pyridyl)-7-chloro-4-methyl-8-(trifluoromethyl)-4H-imidazo[1,2-a][1,4]benzodiazepin-2-yl]methanone A mixture of 3-[(3S)-5-(6-benzyloxy-3-fluoro-2-pyridyl)-6-chloro-2-imino-3-methyl-7-(trifluoromethyl)-3H-1,4-benzodiazepin-1-yl]-2-oxo-propanoic acid (319 mg, 0.340 mmol), HATU (193.9 mg, 0.510 mmol), azetidine (58.2 mg, 1.02 mmol) and N,N-diisopropylethylamine (219.7 mg, 0.29 mL, 1.7 mmol) N,N-dimethylformamide (3.2 mL) was stirred at 25° C. for 90 min. The reaction mixture was quenched with water and extracted with ethyl acetate. The organic layer was washed with brine and dried over Na₂SO₄ and concentrated in vacuo. The residue was purified by flash column chromatography (silica, 0-70% ethyl acetate in heptane) to afford the title compound (41 mg, 21%) as a light yellow powder. MS: 584.3 ([{³⁵Cl}M+H]⁺), 586.2 ([{³⁷Cl}M+H]⁺), ESI pos.

c) azetidin-1-yl-[(4S)-7-chloro-6-(3-fluoro-6-hydroxy-2-pyridyl)-4-methyl-8-(trifluoromethyl)-4H-imidazo[1,2-a][1,4]benzodiazepin-2-yl]methanone To a mixture of azetidin-1-yl-[(4S)-6-(6-benzyloxy-3-fluoro-2-pyridyl)-7-chloro-4-methyl-8-(trifluoromethyl)-4H-imidazo[1,2-a][1,4]benzodiazepin-2-yl]methanone (41 mg, 0.070 mmol) in acetonitrile (1.1 mL) was added trimethyliodosilane (43.5 mg, 30 uL, 0.211 mmol) at room temperature. The mixture was stirred at 80° C. for 3 h, then concentrated in vacuo. Th residue was purified by flash column chromatography (silica, 0-10% MeOH in DCM), then by chiral SFC (Daicel Chiralcel IH, 15-30% methanol containing 0.2% DEA) to afford the enantiopure (+)-title compound (2 mg, 12%) as a white viscous oil. MS: 494.3 ([{³⁵Cl}M+H]⁺), 496.2 ([{³⁷Cl}M+H]⁺), ESI pos.

Example 31

(4S)-7-chloro-N-cyclopropyl-6-(3-fluoro-6-hydroxy-2-pyridyl)-4-methyl-8-(trifluoromethyl)-4H-imidazo[1,2-a][1,4]benzodiazepine-2-carboxamide

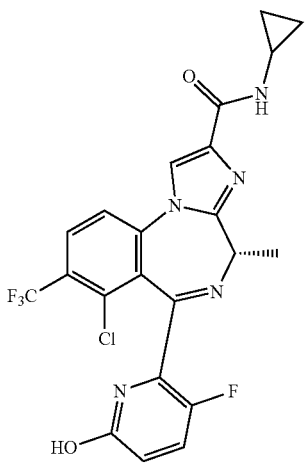 [SMILES: C[C@@H]1N=C(c2nc(O)ccc2F)c2c(ccc(C(F)(F)F)c2Cl)-n2cc(C(=O)NC3CC3)nc21]

a) tert-butyl N-[(1S)-2-(cyclopropylamino)-1-(hydroxymethyl)-2-oxo-ethyl]carbamate To a solution of (2R)-2-(tert-butoxycarbonylamino)-3-hydroxy-propanoic acid (1.5 g, 7.31 mmol) in anhydrous tetrahydrofuran (37 ml) was added cyclopropylamine (1.28 g, 1.58 mL, 21.93 mmol), N,N-diisopropylethylamine (2.83 g, 3.74 mL, 21.93 mmol) and T₃P (11.63 g, 10.77 mL, 18.27 mmol). The reaction mixture was stirred at room temperature for 2 h. Saturated aqueous sodium bicarbonate (10 mL) was added and the mixture was stirred for 5 min. The aqueous phase was extracted with ethyl acetate (3×10 mL). The combined organic layers were washed with brine, dried over sodium sulfate and concentrated in vacuo. The residue was purified by flash column chromatography (silica, 0-2% MeOH in DCM) to afford the title compound (618 mg, 31%) as a white powder which was used as such in the following step without further characterization.

b) (2S)-2-amino-N-cyclopropyl-3-hydroxy-propanamide hydrochloride

To a solution of tert-butyl N-[(1S)-2-(cyclopropylamino)-1-(hydroxymethyl)-2-oxo-ethyl]carbamate (618 mg, 2.28 mmol) in ethyl acetate (15 mL) at 0° C. was added HCl (4 M in dioxane, 5.7 mL, 22.77 mmol) dropwise and the mixture was stirred at 0° C. to room temperature overnight. The reaction mixture was filtered and the solid was dried in vacuo to afford the title compound (380 mg, 92%) as a white powder which was used as such in the following step without further purification. ¹H NMR (D₂O, 300 MHz) δ ppm: 0.40-0.56 (m, 2H), 0.61-0.81 (m, 2H), 2.51-2.64 (m, 1H), 3.77-4.00 (m, 3H).

c) 2-[(E/Z)-[(3S)-5-(6-benzyloxy-3-fluoro-2-pyridyl)-6-chloro-3-methyl-7-(trifluoromethyl)-1,3-dihydro-1,4-benzodiazepin-2-ylidene]amino]-N-cyclopropyl-3-hydroxy-propanamide To a solution of (3S)-5-(6-benzoxy-3-fluoro-2-pyridyl)-6-chloro-3-methyl-7-(trifluoromethyl)-1,3-dihydro-1,4-benzodiazepin-2-one (Building block J, 120 mg, 0.251 mmol) in anhydrous tetrahydrofuran (4 mL) was added at 0° C. NaH (60% dispersion in mineral oil, 30.1 mg, 0.753 mmol). After stirring for 10 min at 10° C. bis(2-oxo-3-oxazolidinyl) phosphinic chloride (127.9 mg, 0.502 mmol) was added and the reaction mixture was stirred at 0° C. for 1 h. Finally (2S)-2-amino-N-cyclopropyl-3-hydroxy-propanamide hydrochloride (164.2 mg, 0.753 mmol) and DIPEA (129.8 mg, 0.172 mL, 1. mmol) were added and the reaction mixture was stirred at room temperature for 60 min. The reaction mixture was quenched with water and saturated aqueous NH₄Cl (10 ml) and extracted with ethylacetate (2×10 ml). The combined organic layers were washed with water (10 ml) and brine (10 ml), dried over sodium sulfate, filtered and concentrated in vacuo. The residue was purified by flash column chromatography (silica, 0-80%, ethyl acetate in heptane) to afford the title compound (48 mg, 32%) as a light yellow powder. MS: 604.5 ([{³⁵Cl}M+H]⁺), 606.4 ([{³⁷Cl}M+H]⁺), ESI pos.

d) (4S)-6-(6-benzyloxy-3-fluoro-2-pyridyl)-7-chloro-N-cyclopropyl-4-methyl-8-(trifluoromethyl)-4H-imidazo[1,2-a][1,4]benzodiazepine-2-carboxamide In analogy to experiment of example 24 b, 2-[(E/Z)-[(3S)-5-(6-benzyloxy-3-fluoro-2-pyridyl)-6-chloro-3-methyl-7-(trifluoromethyl)-1,3-dihydro-1,4-benzodiazepin-2-ylidene]amino]-N-cyclopropyl-3-hydroxy-propanamide was converted into the title compound (26 mg, 45%) which was obtained as a light yellow powder. MS: 584.4 ([{³⁵Cl}M+H]⁺), 586.3 ([{³⁷Cl}M+H]⁺), ESI pos.

e) (4S)-7-chloro-N-cyclopropyl-6-(3-fluoro-6-hydroxy-2-pyridyl)-4-methyl-8-(trifluoromethyl)-4H-imidazo[1,2-a][1,4]benzodiazepine-2-carboxamide In analogy to experiment of example 23 d, (4S)-6-(6-benzyloxy-3-fluoro-2-pyridyl)-7-chloro-N-cyclopropyl-4- methyl-8-(trifluoromethyl)-4H-imidazo[1,2-a][1,4]benzodi-azepine-2-carboxamide was converted into the enantiopure (+)-title compound (5 mg, 39%) which was obtained as a light grey powder. MS: 494.3 ([{$^{35}$Cl}M+H]$^+$), 496.2 ([{$^{37}$Cl}M+H]$^+$), ESI pos.

Example 32

(4S)-7-chloro-6-(3-fluoro-6-hydroxy-2-pyridyl)-N-isopropyl-4-methyl-8-(trifluoromethyl)-4H-imidazo[1,2-a][1,4]benzodiazepine-2-carboxamide

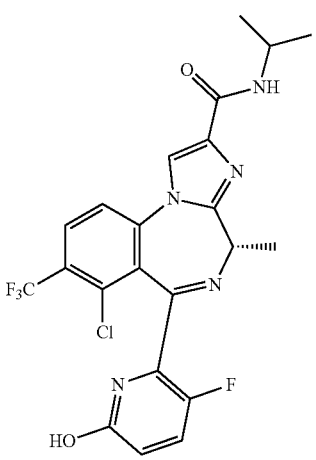 [SMILES: CC(C)NC(=O)c1cn2c(n1)[C@H](C)N=C(c1nc(O)ccc1F)c1c-2ccc(C(F)(F)F)c1Cl]

a) tert-butyl N-[(1S)-1-(hydroxymethyl)-2-(isopropylamino)-2-oxo-ethyl]carbamate In analogy to experiment of example 31 a, (2R)-2-(tert-butoxycarbonylamino)-3-hydroxy-propanoic acid, using isopropylamine instead of cyclopropylamine, was converted into the title compound (139 mg, 12%) which was obtained as an off-white viscous oil which was used as such in the following step without further characterization.

b) (2S)-2-amino-3-hydroxy-N-isopropyl-propanamide hydrochloride

In analogy to experiment of example 31 b, tert-butyl N-[(1S)-1-(hydroxymethyl)-2-(isopropylamino)-2-oxo-ethyl]carbamate was converted into the title compound (144 mg, 95%) which was obtained as a white powder which was used as such in the following step without further purification. $^1$H NMR (DMSO-d$_6$, 300 MHz) δ ppm: 1.04-1.14 (m, 6H), 3.23-3.56 (m, 2H), 3.64-3.77 (m, 2H), 3.86 (dd, J=13.90, 6.65 Hz, 1H), 5.30-5.70 (m, 1H), 8.17 (br s, 2H), 8.37 (br d, J=7.05 Hz, 1H).

c) 2-[(E/Z)-[(3S)-5-(6-benzyloxy-3-fluoro-2-pyridyl)-6-chloro-3-methyl-7-(trifluoromethyl)-1,3-dihydro-1,4-benzodiazepin-2-ylidene]amino]-3-hydroxy-N-isopropyl-propanamide In analogy to experiment of example 31 c, (3S)-5-(6-benzyloxy-3-fluoro-2-pyridyl)-6-chloro-3-methyl-7-(trifluoromethyl)-1,3-dihydro-1,4-benzodiazepin-2-one (Building block J), using (2S)-2-amino-3-hydroxy-N-isopropyl-propanamide hydrochloride instead of (2S)-2-amino-N-cyclopropyl-3-hydroxy-propanamide hydrochloride, was converted into the title compound (88 mg, 42%) which was obtained as an orange viscous oil. MS: 606.4 ([{$^{35}$Cl}M+H]$^+$), 608.4 ([{$^{37}$Cl}M+H]$^+$), ESI pos.

d) (4S)-6-(6-benzyloxy-3-fluoro-2-pyridyl)-7-chloro-N-isopropyl-4-methyl-8-(trifluoromethyl)-4H-imidazo[1,2-a][1,4]benzodiazepine-2-carboxamide In analogy to experiment of example 24 b, 2-[(E/Z)-[(3S)-5-(6-benzyloxy-3-fluoro-2-pyridyl)-6-chloro-3-methyl-7-(trifluoromethyl)-1,3-dihydro-1,4-benzodiazepin-2-ylidene]amino]-3-hydroxy-N-isopropyl-propanamide was converted into the title compound (42 mg, 55%) which was obtained as a light yellow powder. MS: 586.4 ([{$^{35}$Cl}M+H]$^+$), 588.3 ([{$^{37}$Cl}M+H]$^+$), ESI pos.

e) (4S)-7-chloro-6-(3-fluoro-6-hydroxy-2-pyridyl)-N-isopropyl-4-methyl-8-(trifluoromethyl)-4H-imidazo[1,2-a][1,4]benzodiazepine-2-carboxamide In analogy to experiment of example 23 d, (4S)-6-(6-benzyloxy-3-fluoro-2-pyridyl)-7-chloro-N-isopropyl-4-methyl-8-(trifluoromethyl)-4H-imidazo[1,2-a][1,4]benzodiazepine-2-carboxamide was converted into the enantiopure (+)-title compound (9 mg, 36%) which was obtained as a light pink powder. MS: 496.3 ([{$^{35}$Cl}M+H]$^+$), 498.3 ([{$^{37}$Cl}M+H]$^+$), ESI pos.

Reference Compound RE-A 7-chloro-5-(2-chloro-5-hydroxy-phenyl)-1-methyl-3H-1,4-benzodiazepin-2-one

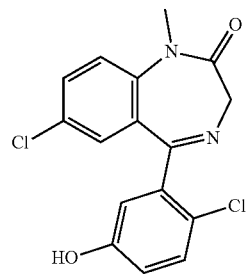 [SMILES: CN1C(=O)CN=C(c2cc(O)ccc2Cl)c2cc(Cl)ccc21]

a) 6-chloro-1-[(4-methoxyphenyl)methyl]-3,1-benzoxazine-2,4-dione

To a mixture of 6-chloro-1H-3,1-benzoxazine-2,4-dione (1.00 g, 5.06 mmol) in tetrahydrofuran (15 mL) was added 1-(chloromethyl)-4-methoxy-benzene (832 mg, 0.746 mL, 5.31 mmol) and tetra-n-butylammonium iodide (935 mg, 2.53 mmol). The mixture was stirred at room temperature for 5 min, before addition of sodium hydride (60% dispersion in mineral oil, 223 mg, 5.57 mmol). The reaction mixture was stirred for 19 h, then quenched by a dropwise addition of acetic acid (1.05 g, 1 mL, 17.5 mmol). The reaction mixture was stirred for 30 min, filtered over Dicalite®, washed with tetrahydrofuran and the filtrate was concentrated in vacuo. The residue was purified by flash column chromatography (silica, 0 to 40% ethyl acetate in heptane) to afford the title compound (1.28 g, 80%) as a light yellow solid. $^1$H NMR (CDCl$_3$, 300 MHz) δ ppm: 3.79 (3H, s, OCH$_3$), 5.23 (2H, s, ArCH$_2$N), 6.86-6.91 (2H, m, ArH), 7.11 (1H, d, J=8.87 Hz, ArH), 7.20-7.25 (2H, m, ArH), 7.57 (1H, dd, J=8.87, 2.62 Hz, ArH), 8.11 (1H, d, J=2.62 Hz, ArH).

b) 7-chloro-1-[(4-methoxyphenyl)methyl]-3,4-dihydro-1,4-benzodiazepine-2,5-dione To a mixture of 6-chloro-1-[(4-methoxyphenyl)methyl]-3,1-benzoxazine-2,4-dione (4.80 g, 15.1 mmol) and glycine (1.36 g, 18.1 mmol) was added acetic acid (50 mL). The reaction mixture was stirred at 130° C. for 43 h, allowed to cool, and concentrated in vacuo. The residue was partitioned between dichloromethane (50 mL) and water (40 mL). The aqueous layer was buffered to pH~8 with saturated aqueous sodium hydrogen carbonate. The phases were separated and the aqueous layer was extracted with dichloromethane (2×75 mL) and ethyl acetate (2×50 mL). The organic layers were separately washed with brine (2×100 mL), dried (Na$_2$SO$_4$), filtered, combined and concentrated in vacuo. The residue was purified by flash column chromatography (silica, 0 to 70% ethyl acetate in heptane) to afford the title compound (3.59 g, 72%) as a white solid. MS: 331.1 [{$^{35}$Cl} M+H]$^+$, 333.1 [{$^{37}$Cl} M+H]$^+$, ESI pos.

c) 5,7-dichloro-1-[(4-methoxyphenyl)methyl]-3H-1,4-benzodiazepin-2-one

To a solution of 7-chloro-1-[(4-methoxyphenyl)methyl]-3,4-dihydro-1,4-benzodiazepine-2,5-dione (211 mg, 0.638 mmol) in toluene (3 mL) was added N,N-dimethylaniline (155 mg, 0.162 mL, 1.28 mmol) and phosphoryl trichloride (127 mg, 0.077 mL, 0.829 mmol). The reaction mixture was stirred at 80° C. for 18 h, allowed to cool, then quenched with ice-cold water (5 mL). The mixture was stirred for 15 min and then partitioned between ice-cold water (5 mL) and ethyl acetate (10 mL). The phases were separated and the organic layer was quickly washed with ice-cold water (2×10 mL) and ice-cold brine (2×10 mL), dried (Na$_2$SO$_4$), filtered and concentrated in vacuo to afford the title compound (193 mg, 90% purity, 78%) as a brown waxy solid. The residue was used as such in the following step without further purification. MS: 349.1 [{$^{35}$Cl} M+H]$^+$, 351.1 [{$^{37}$Cl} M+H]f, ESI pos.

d) 7-chloro-5-(2-chloro-5-methoxy-phenyl)-1-[(4-methoxyphenyl)methyl]-3H-1,4-benzodiazepin-2-one To a mixture of 5,7-dichloro-1-[(4-methoxyphenyl) methyl]-3H-1,4-benzodiazepin-2-one (40.0 mg, 0.115 mmol) in 1,2-dimethoxyethane (0.400 mL) was added (2-chloro-5-methoxyphenyl)boronic acid (21.4 mg, 0.115 mmol), tetrakis(triphenylphosphane)palladium(0) (2.65 mg, 2.29 µmol) and aqueous sodium carbonate (2 M, 0.172 mL, 0.344 mmol). The reaction mixture was stirred at 80° C. for 3 h, allowed to cool and then partitioned between ethyl acetate (10 mL) and water (10 mL). The phases were separated and the aqueous layer was extracted with ethyl acetate (2×10 mL). The combined organic layers were washed with brine (2×20 mL), dried (Na$_2$SO$_4$), filtered and concentrated in vacuo. The residue was purified by flash column chromatography (silica, 0 to 50% ethyl acetate in heptane) to afford the title compound (46.0 mg, 88%) as a white solid. MS: 455.1 [{$^{35}$Cl, $^{35}$Cl} M+H]$^+$, 457.1 [{$^{35}$Cl, $^{37}$Cl} M+H]$^+$, 459.1 [{$^{37}$Cl, $^{37}$Cl} M+H]$^+$, ESI pos.

e) 7-chloro-5-(2-chloro-5-methoxy-phenyl)-1,3-dihydro-1,4-benzodiazepin-2-one To a mixture of 7-chloro-5-(2-chloro-5-methoxy-phenyl)-1-[(4-methoxyphenyl)methyl]-3H-1,4-benzodiazepin-2-one (320 mg, 0.703 mmol) in acetonitrile (20.1 mL) and water (3.35 mL) was added diammonium cerium(IV) nitrate (1.35 g, 2.46 mmol) by portions. The reaction mixture was stirred at room temperature for 6.5 h, then partitioned between water (50 mL) and ethyl acetate (50 mL). The phases were separated and the aqueous layer was extracted with ethyl acetate (3×50 mL). The combined organic layers were washed with brine (2×100 mL), dried (Na$_2$SO$_4$), filtered and concentrated in vacuo. The residue was purified by flash column chromatography (silica, 0 to 50% ethyl acetate in heptane) to afford the title compound (187 mg, 79%) as an off-white solid. MS: 335.1 [{$^{35}$Cl, $^{35}$Cl} M+H]$^+$, 337.1 [{$^{35}$Cl, $^{37}$Cl} M+H]$^+$, 339.1 [{$^{37}$Cl, $^{37}$Cl} M+H]$^+$, ESI pos.

f) 7-chloro-5-(2-chloro-5-methoxy-phenyl)-1-methyl-3H-1,4-benzodiazepin-2-one To a mixture of 7-chloro-5-(2-chloro-5-methoxy-phenyl)-1,3-dihydro-1,4-benzodiazepin-2-one (30.0 mg, 89.5 µmol) in N,N-dimethylformamide (0.500 mL) was added methyl iodide (22.9 mg, 10.1 µL, 0.161 mmol) and sodium hydride (60% dispersion in mineral oil, 4.3 mg, 0.107 mmol).

The mixture was stirred at room temperature for 5 h, then partitioned between water (20 mL) and ethyl acetate (20 mL). The phases were separated and the aqueous layer was extracted with ethyl acetate (2×15 mL). The combined organic layers were washed with brine (2×50 mL), dried (Na$_2$SO$_4$), filtered and concentrated in vacuo. The residue was purified by flash column chromatography (silica, 0 to 5% ethyl acetate in heptane) to afford the title compound (17.0 mg, 54%) as a light brown waxy solid. MS: 349.1 [{$^{35}$Cl, $^{35}$Cl} M+H]$^+$, 351.1 [{$^{35}$Cl, $^{37}$Cl} M+H]$^+$, 353.1 [{$^{37}$Cl, $^{37}$Cl} M+H]$^+$, ESI pos.

g) 7-chloro-5-(2-chloro-5-hydroxy-phenyl)-1-methyl-3H-1,4-benzodiazepin-2-one To a mixture of 7-chloro-5-(2-chloro-5-methoxy-phenyl)-1-methyl-3H-1,4-benzodiazepin-2-one (10.0 mg, 0.0286 mmol) in dichloromethane (0.130 mL) at −20° C., was added boron tribromide (1 M in dichloromethane, 0.100 mL, 0.100 mmol). The mixture was allowed to warm up to room temperature and stirred for 1 h, then quenched by a careful addition of methanol (0.100 mL) and aqueous sodium hydroxide (2 M, 0.100 mL) and stirred for 30 min. The mixture was then partitioned between water (10 mL) and dichloromethane (10 mL). The phases were separated and the aqueous layer was extracted with dichloromethane (2×10 mL). The combined organic layers were washed with water (20 mL) and brine (20 mL), dried (Na$_2$SO$_4$), filtered and concentrated in vacuo. The residue was purified by preparative HPLC to afford the title compound (6.60 mg, 69%) as an off-white solid. MS: 335.1 [{$^{35}$Cl, $^{35}$Cl} M+H]$^+$, 337.1 [{$^{35}$Cl, $^{37}$Cl} M+H]$^+$, 339.1 [{$^{37}$Cl, $^{37}$Cl} M+H]$^+$, ESI pos. $^1$H NMR (CDCl$_3$, 300 MHz) δ ppm: 3.44 (3H, s, NCH$_3$), 3.83 (1H, br d, J=10.7 Hz, COCH$_2$N), 4.85 (1H, br d, J=10.7 Hz, COCH$_2$N), 6.80 (1H, dd, J=8.7, 3.0 Hz, ArH), 7.03 (1H, d, J=3.0 Hz, ArH), 7.09 (1H, d, J=2.4 Hz, ArH), 7.12 (1H, d, J=8.7 Hz, ArH), 7.29 (1H, d, J=8.9 Hz, ArH), 7.50 (1H, dd, J=8.9, 2.4 Hz, ArH), 7.72 (1H, br s, ArOH).

Reference Compound RE-B 7-chloro-5-(2-fluoro-5-hydroxy-phenyl)-1-methyl-3H-1,4-benzodiazepin-2-one

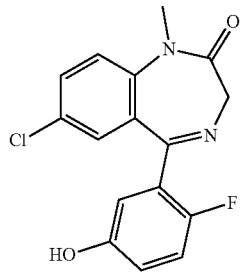 [SMILES: CN1C(=O)CN=C(c2cc(O)ccc2F)c2cc(Cl)ccc21]

a)
2-amino-5-chloro-N-methoxy-N-methyl-benzamide

To a mixture of 2-amino-5-chloro-benzoic acid (4.0 g, 23.3 mmol) in tetrahydrofuran (50 mL) was added N,N-carbonyldiimidazole (4.16 g, 25.6 mmol) followed by triethylamine (4.42 mL, 35.0 mmol). The mixture was stirred for 2 h at rt, then O,N-dimethylhydroxylamine hydrochloride (2.5 g, 25.6 mmol) was added. The reaction mixture was stirred for 16 h at room temperature, then diluted with ethyl acetate (200 mL). The organic layer was washed with saturated aqueous solution of sodium carbonate (100 mL) and brine (100 mL), dried ($Na_2SO_4$), filtered and concentrated in vacuo. The residue was purified by flash column chromatography (silica, 30% ethyl acetate in heptane) to afford the title compound (3.4 g, 54%) as a white solid. MS: 215.1 [{$^{35}$Cl} M+H]$^+$, ESI pos.

b) (2-amino-5-chloro-phenyl)-(2-fluoro-5-methoxy-phenyl)methanone

To a mixture of 2-amino-5-chloro-N-methoxy-N-methyl-benzamide (1.57 g, 7.32 mmol) and 2-bromo-1-fluoro-4-methoxy-benzene (1.5 g, 7.32 mmol) in anhydrous tetrahydrofuran (40 mL) at −78° C. under nitrogen was added n-butyllithium (1.6 M in hexane, 9.15 mL, 14.63 mmol). The resulting solution was stirred for 30 min, then quenched with diluted aqueous hydrochloric acid (50 mL) and extracted with ethyl acetate (3×100 mL). The combined organic layers were washed with brine (50 mL), dried ($Na_2SO_4$), filtered and concentrated in vacuo. The residue was purified by flash column chromatography (silica, 60% ethyl acetate in heptane) to afford the title compound (800 mg, 30%) as a yellow oil. MS: 279.8 [{$^{35}$Cl} M+H]$^+$, 281.8 ([{$^{37}$Cl}M+H]$^+$), ESI pos.

c) 7-chloro-5-(2-fluoro-5-methoxy-phenyl)-1,3-dihydro-1,4-benzodiazepin-2-one

To a mixture of (2-amino-5-chloro-phenyl)-(2-fluoro-5-methoxy-phenyl)methanone (250 mg, 0.89 mmol) in pyridine (15 mL) was added glycine methyl ester hydrochloride (997 mg, 8.94 mmol). The reaction mixture was stirred at 110° C. for 16 h, then concentrated in vacuo. The residue was purified by flash column chromatography (silica, 50% ethyl acetate in heptane) to afford the title compound (30 mg, 11%) as a light yellow solid. MS: 318.9 [{$^{35}$Cl} M+H]$^+$, 320.8 ([{$^{37}$Cl}M+H]$^+$), ESI pos.

d) 7-chloro-5-(2-fluoro-5-methoxy-phenyl)-1-methyl-3H-1,4-benzodiazepin-2-one

To a mixture of 7-chloro-5-(2-fluoro-5-methoxy-phenyl)-1,3-dihydro-1,4-benzodiazepin-2-one (300 mg, 0.94 mmol) in N,N-dimethylformamide (10 mL) was added iodomethane (2672 mg, 18.82 mmol) and potassium carbonate (195 mg, 1.41 mmol). The reaction mixture was stirred at 25° C. for 1 h, then quenched with water (50 mL) and extracted with ethyl acetate (2×50 mL). The combined organic layers were dried ($Na_2SO_4$), filtered and concentrated in vacuo. The residue was purified by flash column chromatography (silica, 50% ethyl acetate in heptane) to afford the title compound (160 mg, 44%) as a light yellow solid. MS: 332.9 [{$^{35}$Cl} M+H]$^+$, 334.8 ([{$^{37}$Cl}M+H]$^+$), ESI pos.

e) 7-chloro-5-(2-fluoro-5-hydroxy-phenyl)-1-methyl-3H-1,4-benzodiazepin-2-one

To a mixture of 7-chloro-5-(2-fluoro-5-methoxy-phenyl)-1-methyl-3H-1,4-benzodiazepin-2-one (160 mg, 0.48 mmol) in dichloromethane (10 mL) at 0° C. was added $BBr_3$ (1 M in dichloromethane, 2.4 mL, 2.4 mmol) dropwise. The reaction mixture was stirred at 0° C. for 1 h, allowed to warm to room temperature and stirred for an additional 5 h. The reaction was quenched with ice water (10 mL) and extracted with dichloromethane (2×20 mL). The combined organic layers were dried ($Na_2SO_4$), filtered and concentrated in vacuo. The residue was purified by preparative HPLC (X-Select CSH C18, water containing 0.1% formic acid/acetonitrile) to afford the title compound (40 mg, 25%) as a white solid. MS: 319.3 [{$^{35}$Cl} M+H]f, ESI pos. $^1$H NMR (DMSO-$d_6$, 400 MHz) δ ppm: 3.31 (3H, s, NCH$_3$), 3.84 (1H, br d, J=9.6 Hz, COCH$_2$N), 4.65 (1H, br d, J=10.5 Hz, COCH$_2$N), 6.93-6.97 (1H, m), 7.00 (1H, br s), 7.07 (1H, br d, J=8.3 Hz), 7.64 (1H, br s), 9.68 (1H, br s).

Assay Procedures

Membrane Preparation and Binding Assay for γ1-Containing $GABA_A$ Subtypes

The affinity of compounds at $GABA_A$ γ1 subunit-containing receptors was measured by competition for [$^3$H] RO7239181 (67.3 Ci/mmol; Roche) binding to membranes from HEK293F cells (ThermoFisher R79007) expressing human (transiently transfected) receptors of composition α5β2γ1, α2β2γ1, α1β2γ1. For better protein expression of the α2 subunit-containing receptors, the 28 amino acid long signal peptide (Met1 to Ala28) of the human $GABA_A$ α2 subunit was substituted by the 31 amino acid long signal peptide (Met1 to Ser31) of human $GABA_A$ α5 subunit.

Harvested pellets from HEK293F cells expressing the different $GABA_A$ receptor subtypes were resuspended in Mannitol Buffer pH 7.2-7.4 (Mannitol 0.29M, Triethylamine 10 mM, Acetic acid 10 mM, EDTA 1 mM plus protease inhibitors (20 tablets Complete, Roche Diagnostics Cat. No. 05 056 489 001 per liter)), washed two times and then resuspended at 1:10 to 1:15 dilution in the same buffer. Cell disruption was performed by stirring the suspension in a Parr vessel #4637 at 435 psi for 15 minutes, and then the suspensions were centrifuged at 1000×g for 15 minutes at 4° C. (Beckman Avanti J-HC; rotor JS-4.2). The supernatant (S1) was transferred in a 2l Schott flask and the pellet (P1) was resuspended with Mannitol Buffer up to 175 ml. The resuspended pellet was transferred into a 250 ml Corning centrifugal beaker and centrifuged at 1500×g for 10 minutes at 4° C. (Beckman Avanti J-HC; rotor JS-4.2). The supernatant (S1) was then transferred in the 21 Schott flask and the pellet was discarded. The supernatants (S1) were centrifuged in 500 ml Beckman polypropylene centrifugal beaker at 15'000×g for 30 minutes at 4° C. (Beckman Avanti J-20 XP; rotor JLA-10.500). The pellet (P2) was resuspended with Mannitol Buffer 1:1 and frozen at −80° C. The supernatant (S2) was centrifuged in 100 ml Beckman polypropylene centrifugal tubes at 48000×g for 50 minutes at 4° C. (Beckman Avanti J-20 XP; rotor JA-18). The supernatant (S3) was discarded and the pellet (P3) was resuspended with 1:1 Mannitol Buffer. The P2 and P3 protein concentration was determined with the BIORAD Standard assay method with bovine serum albumin as standard and measured on the NANO-Drop 1000. The membrane suspension was aliquots (500 µl per tube) and stored at −80° C. until required.

Membrane homogenates were resuspended and polytronised (Polytron PT1200E Kinematica AG) in Potassium Phosphate 10 mM, KCl 100 mM binding buffer at pH 7.4 to a final assay concentration determined with a previous experiment.

Radioligand binding assays were carried out in a volume of 200 µL (96-well plates) which contained 100 µL of cell membranes, [$^3$H]RO7239181 at a concentration of 1.5 nM (α5β2γ1) or 20-30 nM (α1β2γ1, α2β2γ1) and the test compound in the range of [0.3-10000]×10$^{-9}$ M. Nonspecific binding was defined by 10×10$^{-6}$ (α5β2γ1) and 30×10$^{-6}$ M RO7239181 and typically represented less than 5% (α5β2γ1) and less than 20% (α1β2γ1, α2β2γ1) of the total binding. Assays were incubated to equilibrium for 1 hour at 4° C. and then, membranes were filtered onto unifilter (96-well white microplate with bonded GF/C filters preincubated 20-50 minutes in 0.3% Polyethylenimine) with a Filtermate 196 harvester (Packard BioScience) and washed 4 times with cold Potassium Phosphate 10 mM pH 7.4, KCl 100 mM binding buffer. After anhydrousing, filter-retained radioactivity was detected by liquid scintillation counting. $K_i$ values were calculated using Excel-Fit (Microsoft) and are the means of two determinations.

The compounds of the accompanying examples were tested in the above described assays, and the preferred compounds were found to possess a $K_i$ value for the displacement of [$^3$H]RO7239181 from GABA$_A$ γ1 subunit-containing receptors (e.g. α5β2γ1, α2β2γ1, α1β2γ1) of 100 nM or less. Most preferred are compounds with a Ki (nM)<50. Representative test results, obtained by the above described assay measuring binding affinity to HEK293 cells expressing human (h) receptors, are shown in the Table 1.

Preparation of [$^3$H]RO7239181, 6-chloro-5-(2,6-difluorophenyl)-7-methyl-1-(tritritiomethyl)-3H-1,4-benzodiazepin-2-one

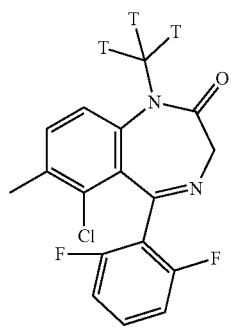

a) 6-chloro-5-(2,6-difluorophenyl)-7-methyl-1,3-dihydro-1,4-benzodiazepin-2-one

A microwave tube was charged with 7-bromo-6-chloro-5-(2,6-difluorophenyl)-1,3-dihydro-1,4-benzodiazepin-2-one (building block A (see infra), 450 mg, 1.17 mmol), trimethylboroxine (205 mg, 228 µL, 1.63 mmol), potassium carbonate (242 mg, 1.75 mmol) and tetrakis(triphenylphosphine)palladium (0) (67.4 mg, 58.4 µmol). Degassed 1,4-dioxane (8.1 mL) and H$_2$O (2.7 ml) were added then the vial was capped. The suspension was reacted in microwave at 130° C. for 30 min to give complete conversion. The mixture was evaporated, treated with sat. aq. NaHCO$_3$ (20 mL) and extracted with EtOAc (2×20 mL). The organic layers were dried (Na$_2$SO$_4$), filtered and solvents were evaporated. The residue was purified by flash column chromatography (silica, 40 g, CH$_2$Cl$_2$/EtOAc in heptane 10% to 40% to 70%) to give the title compound (344 mg, 92%) as light yellow solid. MS (ESI): 321.1 ([M+H]$^+$).

b) 6-chloro-5-(2,6-difluorophenyl)-7-methyl-1-(tritritiomethyl)-3H-1,4-benzodiazepin-2-one To a solution of [$^3$H]methyl nosylate (1.85 GBq, 50 mCi, 0.61 µmol) in THF (200 µL) were added the N-desmethyl precursor 6-chloro-5-(2,6-difluorophenyl)-7-methyl-1,3-dihydro-1,4-benzodiazepin-2-one (0.43 mg, 1.34 µmol) dissolved in THF (200 µL) and 10 equivalents of sodium tert-butylate (0.5 M in THF, 13.4 µmol). After stirring for 4 h at room temperature the reaction mixture was treated with H$_2$O, evaporated, and the crude product was purified by HPLC (X-Terra Prep RP-18, 10×150 mm, MeCN/H$_2$O (containing 5% of MeCN) 40:60, 4 ml/min, 230 nm). The pure tritium-labeled compound was isolated by solid phase extraction (Sep-Pak Plus C18) and eluted from the cartridge as ethanolic solution to yield 1.6 GBq (43.2 mCi) of the target compound in >99% radio-chemical purity and a specific activity of 2.49 TBq/mmol (67.3 Ci/mmol) as determined by mass spectrometry (MS). The identity of the labeled compound was confirmed by HPLC (by co-injecting the unlabeled reference standard) and by MS.

MS: m/z=335 [M(H)+H]$^+$ (16%), 337 [M($^3$H)+H]$^+$ (0%), 339 [M($^3$H$_2$)+H]$^+$ (16%), 341 [M($^3$H$_3$)+H]$^+$ (68%).

Membrane Preparation and Binding Assay for γ2-Containing GABA$_A$ Subtypes

The affinity of compounds at GABA$_A$ γ2 subunit-containing receptors was measured by competition for [$^3$H]Flumazenil (81.1 Ci/mmol; Roche) binding to HEK293F cells expressing human (transiently transfected) receptors of composition α1β3γ2.

Harvested pellets from HEK293F cells expressing the different GABA$_A$ γ2 receptor subtypes were resuspended in Mannitol Buffer pH 7.2-7.4 and processed as described above for the cells expressing the GABA$_A$ γ1 subunit-containing receptors.

Radioligand binding assays were carried out in a volume of 200 µL (96-well plates) which contained 100 µL of cell membranes, [$^3$H]Flumazenil at a concentration of 1 nM and the test compound in the range of [0.1-10$^{-3}$-10]×10$^{-6}$ M. Nonspecific binding was defined by 10$^{-5}$ M Diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After anhydrousing, filter-retained radioactivity was detected by liquid scintillation counting.

$K_i$ values were calculated using Excel-Fit (Microsoft) and are the means of two determinations.

The compounds of the accompanying examples were tested in the above described assay, and the preferred compounds were found to possess large $K_i$ value for displacement of [$^3$H]Flumazenil from the α1β3γ2 subtype of the human GABA$_A$ receptor of 100 nM or above. Most preferred are compounds with a $K_i$ α1β3γ2 (nM)>300. In a preferred embodiment the compounds of the invention are binding selectively for the γ1 subunit-containing GABA$_A$ receptors relative to γ2 subunit-containing GABA$_A$ receptors. In particular, compounds of the present invention have γ2/γ1 selectivity ratio defined as "$K_i$ α1β3γ2 (nM)/$K_i$ α2β2γ1 (nM)" above 10-fold, or LogSel defined as "Log[$K_i$ α1β3γ2 (nM)/$K_i$ α2β2γ1 (nM)]" above 1. Representative test results, obtained by the above described assay measuring binding affinity to HEK293 cells expressing human (h) receptors, are shown in the Table 1 below.

subunits of the desired GABA$_A$ receptor subtype was injected into each oocyte. RNA concentrations ranged between 20 and 200 pg/μL/subunit and were adjusted in pilot experiments to obtain GABA responses of a suitable size and a maximal effect of Flunitrazepam, Triazolam and Midazolam, reference benzodiazepine positive allosteric modulators (PAM) at the GABA$_A$ receptor benzodiazepine (BZD) binding site. Oocytes were kept in modified Barth's medium (composition in mM: NaCl 88, KCl 1, NaHCO$_3$ 4, HEPES 10, MgSO$_4$ 0.82, CaNO$_3$ 0.33, CaCl, 0.33, pH=7.5) at 20° C. until the experiment.

Electrophysiology

Electrophysiological experiments were performed using the Roboocyte instrument (MultiChannelSystems, Reutlingen, Germany) on days 3 to 5 after the micro-injection of mRNA. During the experiment the oocytes were constantly superfused by a solution containing (in mM) NaCl 90, KCl 1, HEPES 5, MgCl$_2$ 1, CaCl$_2$ 1 (pH 7.4). Oocytes were

TABLE 1

| Example | Ki h-GABA$_A$ α5β2γ1 (nM) | Ki h-GABA$_A$ α2β2γ1 (nM) | Ki h-GABA$_A$ α1β2γ1 (nM) | Ki h-GABA$_A$ α1β3γ2 (nM) | γ2/γ1 Selectivity Ratio | LogSel |
|---|---|---|---|---|---|---|
| 1 | 0.34 | 2.27 | 2.90 | 28.7 | 12.7 | 1.10 |
| 2 | 0.53 | 1.49 | 3.49 | 58.2 | 39.0 | 1.59 |
| 3 | 0.36 | 1.45 | 5.44 | 34.3 | 23.7 | 1.37 |
| 4 | 0.38 | 1.99 | 3.35 | 81.7 | 41.1 | 1.61 |
| 5 | 0.39 | 1.40 | 3.30 | 255.4 | 182.4 | 2.26 |
| 6 | 0.39 | 2.18 | ND | 46.7 | 21.4 | 1.33 |
| 7 | 1.40 | 2.22 | ND | 34.6 | 15.6 | 1.19 |
| 8 | 0.44 | 2.35 | 5.43 | 80.9 | 34.4 | 1.54 |
| 9 | 0.86 | 3.25 | 8.45 | 105.8 | 32.6 | 1.51 |
| 10 | 0.27 | 1.04 | ND | 89.9 | 86.5 | 1.94 |
| 11 | 1.54 | 1.88 | 5.17 | 358.9 | 191.3 | 2.28 |
| 12 | 0.46 | 2.12 | ND | 371.3 | 175.4 | 2.24 |
| 13 | 0.40 | 3.85 | ND | 72.6 | 18.8 | 1.28 |
| 14 | 0.85 | 4.67 | ND | 74.6 | 16.0 | 1.20 |
| 15 | 0.85 | 4.18 | ND | 120.7 | 28.9 | 1.46 |
| 16 | 1.04 | 3.60 | 11.4 | 164.1 | 45.6 | 1.66 |
| 17 | 0.99 | 1.75 | ND | 68.8 | 39.3 | 1.59 |
| 18 | 1.30 | 6.60 | ND | 255.4 | 38.7 | 1.59 |
| 19 | 2.12 | 3.12 | ND | 33.0 | 10.6 | 1.02 |
| 20 | 5.02 | 40.1 | 68.1 | 11227.4 | 279.6 | 2.45 |
| 21 | 5.51 | 11.8 | ND | >30000.0 | 2538.6 | 3.40 |
| 22 | 20.9 | 13.7 | 42.5 | 9691.6 | 704.8 | 2.85 |
| 23 | 3.08 | 8.88 | ND | 8012.4 | 902.4 | 2.96 |
| 24 | 8.6 | 6.61 | ND | 4191.9 | 634.3 | 2.80 |
| 25 | 2.32 | 10.9 | 25.3 | 10638.0 | 977.2 | 2.99 |
| 26 | 3.25 | 7.88 | 20.5 | 6730.7 | 853.7 | 2.93 |
| 27 | 2.80 | 5.22 | ND | 3546.7 | 679.2 | 2.83 |
| 28 | 2.07 | 5.28 | 19.9 | 4081.9 | 772.7 | 2.89 |
| 29 | 3.63 | 7.70 | ND | 11991.7 | 1557.5 | 3.19 |
| 30 | 8.77 | 46.3 | ND | 13005.9 | 280.8 | 2.45 |
| 31 | 4.40 | 15.6 | ND | 12481.9 | 800.9 | 2.90 |
| 32 | 4.70 | 10.8 | ND | 8596.6 | 796.0 | 2.90 |

Functional Expression of GABA$_A$ Receptors:

*Xenopus* Oocytes Preparation

*Xenopus laevis* oocytes at maturation stages V-VI were used for the expression of cloned mRNA encoding GABA$_A$ receptor subunits. Oocytes ready for RNA micro-injection were bought from Ecocyte, Castrop-Rauxel, Germany and stored in modified Barth's medium (composition in mM: NaCl 88, KCl 1, NaHCO$_3$ 2.4, HEPES 10, MgSO$_4$ 0.82, CaNO$_3$ 0.33, CaCl$_2$ 0.33, pH=7.5) at 20° C. until the experiment.

*Xenopus* Oocytes Microinjection

Oocytes were plated in 96-well plates for microinjection using the Roboinject automated instrument (MultiChannelSystems, Reutlingen, Germany). Approximately 50 nL of an aqueous solution containing the RNA transcripts for the impaled by two glass microelectrodes (resistance: 0.5-0.8 MΩ) which were filled with a solution containing KCl 1M+K-acetate 1.5 M and voltage-clamped to −80 mV. The recordings were performed at room temperature using the Roboocyte two-electrode voltage clamp system (Multichannelsystem). After an initial equilibration period of 1.5 min GABA was added for 1.5 min at a concentration evoking approximately 20% of a maximal current response (EC$_2$0). After another rest interval of 2.5 min GABA was again added evoking a response of similar amplitude and shape. 0.5 min after the onset of this second GABA application the test compound, at a concentration corresponding to approximatively 30-fold its $K_i$ α2β2γ1, was added while GABA was still present. Current traces were recorded at a digitization rate of 10 Hz during and shortly before and after the GABA application.

Each compound and concentration was tested on at least 3 oocytes. Different oocytes were used for different compound concentrations. The reference PAMs, Flunitrazepam, Triazolam and Midazolam, potentiated the GABA-induced current in α2β2γ1 GABA$_A$ receptor subtype expressing oocytes by approximatively 60%.

Data Analysis

For the analysis, the digitized current traces of the first and second GABA response were superimposed and, if necessary, rescaled to equal maximal amplitudes. The ratio between the two responses during the time interval of test compound application was calculated point by point. The extremum of the resulting "ratio trace" was taken as the efficacy ("Fold increase") of the compound expressed as "% modulation of GABA EC$_{20}$" (100*(Fold increase−1)).

The results are shown in Table 2.

TABLE 2

| Example | Ki h-GABA$_A$ α2β2γ1 (nM) | Fold increase h-GABA-A α2β2γ1 oocyte @ 30-fold Ki | Efficacy (GABA) % |
|---|---|---|---|
| 1 | 2.27 | 1.90 | 90 |
| 2 | 1.49 | 1.70 | 70 |
| 3 | 1.45 | 1.67 | 67 |
| 4 | 1.99 | 1.33 | 33 |
| 5 | 1.40 | 1.46 | 46 |
| 6 | 2.18 | 1.92 | 92 |
| 7 | 2.22 | 1.65 | 65 |
| 8 | 2.35 | 1.75 | 75 |
| 9 | 3.25 | 1.69 | 69 |
| 10 | 1.04 | 1.73 | 73 |
| 11 | 1.88 | 1.68 | 68 |
| 12 | 2.12 | 1.99 | 99 |
| 13 | 3.85 | 1.72 | 72 |
| 14 | 4.67 | 1.68 | 68 |
| 15 | 4.18 | 1.80 | 80 |
| 16 | 3.60 | 1.48 | 48 |
| 17 | 1.75 | 1.77 | 77 |
| 18 | 6.60 | 1.57 | 57 |
| 19 | 3.12 | ND | — |
| 20 | 40.1 | 2.20 | 120 |
| 21 | 11.8 | 1.73 | 73 |
| 22 | 13.7 | 1.84 | 84 |
| 23 | 8.88 | 1.68 | 68 |
| 24 | 6.61 | 1.64 | 64 |
| 25 | 10.9 | 1.45 | 45 |
| 26 | 7.88 | 1.79 | 79 |
| 27 | 5.22 | ND | — |
| 28 | 5.28 | 1.68 | 68 |
| 29 | 7.70 | 1.70 | 70 |
| 30 | 46.3 | 2.20 | 120 |
| 31 | 15.6 | ND | — |
| 32 | 10.8 | ND | — |

Reference Compounds

Benzodiazepines reference compounds (classical marketed benzodiazepines) and their structural analogues listed below were tested for their affinity towards the GABA$_A$ receptor α1β2γ1 and α2β2γ1 subtypes as well as in the GABA$_A$ receptor α1β3γ2 subtype. The results are shown in Table 3. Reference examples RE-A and RE-B have been prepared as described herein.

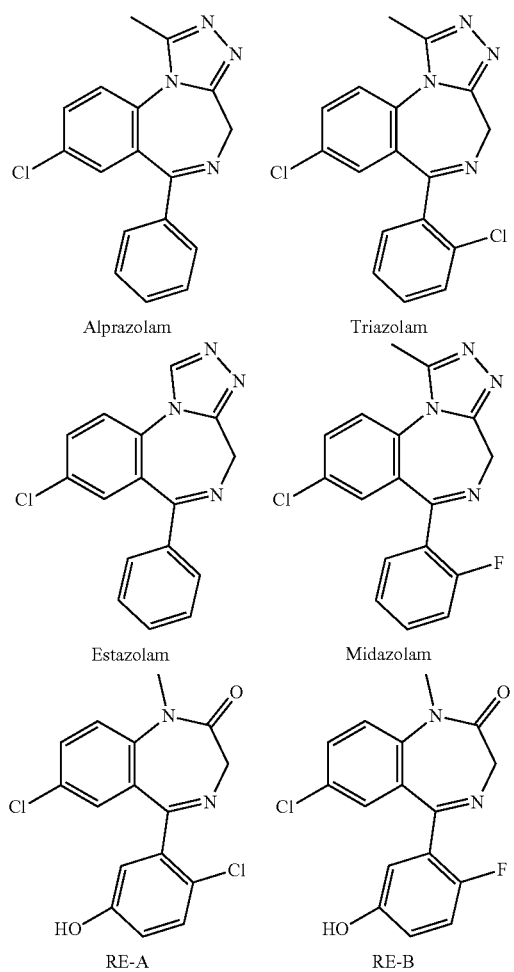

Alprazolam   Triazolam
Estazolam   Midazolam
RE-A   RE-B

TABLE 3

| Example | Ki h-GABA$_A$ α1β2γ1 (nM) | Ki h-GABA$_A$ α2β2γ1 (nM) | Ki h-GABA$_A$ α1β3γ2 (nM) | γ2/γ1 Selectivity Ratio | LogSel |
|---|---|---|---|---|---|
| Alprazolam | 5923 | 3945 | 19.6 | 0.0050 | −2.3 |
| Triazolam | 44.2 | 46.2 | 1.5 | 0.032 | −1.5 |
| Estazolam | ND | 3182 | 28.4 | 0.0089 | −2.0 |
| Midazolam | 1153.2 | 737.7 | 5.0 | 0.0068 | −2.2 |
| RE-A | 6.84 | 2.8 | 1.5 | 0.54 | −0.27 |
| RE-B | ND | 1.9 | 1.1 | 0.58 | −0.24 |
| Example 1 | 2.90 | 2.27 | 28.7 | 12.7 | 1.1 |

Preparation of Pharmaceutical Compositions Comprising Compounds of the Invention Tablets comprising compounds of formula (I) are manufactured as follows:

| Ingredient | mg/tablet | | | |
|---|---|---|---|---|
| | 5 | 25 | 100 | 500 |
| Compound of formula I or II | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |

-continued

| Ingredient | mg/tablet | | | |
|---|---|---|---|---|
| | 5 | 25 | 100 | 500 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules comprising compounds of formula (I) are manufactured as follows:

| Ingredient | mg/capsule | | | |
|---|---|---|---|---|
| | 5 | 25 | 100 | 500 |
| Compound of formula I or II | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoapproximatively. The mixture is filled by machine into suitable capsules, e.g. hard gelatin capsules.

Injection solutions comprising compounds of formula (I) are manufactured as follows:

| Ingredient | mg/injection solution. |
|---|---|
| Compound of formula I or II | 3 |
| Polyethylene Glycol 400 | 150 |
| acetic acid | q.s. ad pH 5.0 |
| water for injection solutions | ad 1.0 ml |

What is claimed is:
1. A compound selected from:
6,7-dichloro-5-(2-fluoro-5-hydroxyphenyl)-1-methyl-1,3-dihydro-2H-benzo[e][1,4]diazepin-2-one;
6-chloro-5-(2-fluoro-5-hydroxyphenyl)-1,7-dimethyl-1,3-dihydro-2H-benzo[e][1,4]diazepin-2-one;
3-(7,8-dichloro-1-methyl-4H-[1,2,4]triazolo[4,3-a][1,4]benzodiazepin-6-yl)-4-fluoro-phenol;
3-[(4S)-7,8-dichloro-1,4-dimethyl-4H-[1,2,4]triazolo[4,3-a][1,4]benzodiazepin-6-yl]-4-fluorophenol;
(5S)-8,9-dichloro-7-(2-fluoro-5-hydroxyphenyl)-5-methyl-5H-pyrimido[1,2-a][1,4]benzodiazepin-3-one;
8,9-dichloro-7-(2-fluoro-5-hydroxy-phenyl)-5H-pyrimido[1,2-a][1,4]benzodiazepin-3-one;
[7,8-dichloro-6-(2-fluoro-5-hydroxy-phenyl)-4H-[1,2,4]triazolo[1,5-a][1,4]benzodiazepin-2-yl]-(3-methoxyazetidin-1-yl)methanone;
6-chloro-5-(2-fluoro-5-hydroxy-phenyl)-1-methyl-7-(trifluoromethyl)-3H-1,4-benzodiazepin-2-one;
3-[7-chloro-1-methyl-8-(trifluoromethyl)-4H-[1,2,4]triazolo[4,3-a][1,4]benzodiazepin-6-yl]-4-fluoro-phenol;
3-[7-chloro-8-(trifluoromethyl)-4H-[1,2,4]triazolo[4,3-a][1,4]benzodiazepin-6-yl]-4-fluoro-phenol;
3-[(4S)-7-chloro-1,4-dimethyl-8-(trifluoromethyl)-4H-[1,2,4]triazolo[4,3-a][1,4]benzodiazepin-6-yl]-4-fluoro-phenol;
8-chloro-7-(2-fluoro-5-hydroxy-phenyl)-9-(trifluoromethyl)-5H-pyrimido[1,2-a][1,4]benzodiazepin-3-one;
6,7-dichloro-5-(2,6-difluoro-3-hydroxy-phenyl)-1-methyl-3H-1,4-benzodiazepin-2-one;
3-(7,8-dichloro-1-methyl-4H-[1,2,4]triazolo[4,3-a][1,4]benzodiazepin-6-yl)-2,4-difluoro-phenol;
8,9-dichloro-7-(2,6-difluoro-3-hydroxy-phenyl)-5H-pyrimido[1,2-a][1,4]benzodiazepin-3-one;
3-[(4S)-7,8-dichloro-1,4-dimethyl-4H-[1,2,4]triazolo[4,3-a][1,4]benzodiazepin-6-yl]-2,4-difluoro-phenol;
[7-chloro-6-(2-fluoro-5-hydroxy-phenyl)-8-(trifluoromethyl)-4H-[1,2,4]triazolo[1,5-a][1,4]benzodiazepin-2-yl]-(3-methoxyazetidin-1-yl)methanone;
(5S)-8,9-dichloro-7-(2,6-difluoro-3-hydroxy-phenyl)-5-methyl-5H-pyrimido[1,2-a][1,4]benzodiazepin-3-one;
[7-chloro-6-(2-fluoro-5-hydroxy-phenyl)-8-(trifluoromethyl)-4H-imidazo[1,5-a][1,4]benzodiazepin-3-yl]-(3-methoxyazetidin-1-yl)methanone;
6-[(4S)-7-chloro-1,4-dimethyl-8-(trifluoromethyl)-4H-[1,2,4]triazolo[4,3-a][1,4]benzodiazepin-6-yl]-5-fluoro-pyridin-2-ol;
[(4S)-7-chloro-6-(3-fluoro-6-hydroxy-2-pyridyl)-4-methyl-8-(trifluoromethyl)-4H-[1,2,4]triazolo[1,5-a][1,4]benzodiazepin-2-yl]-(3-fluoroazetidin-1-yl)methanone;
5-chloro-6-[(4S)-7-chloro-1,4-dimethyl-8-(trifluoromethyl)-4H-[1,2,4]triazolo[4,3-a][1,4]benzodiazepin-6-yl]pyridin-2-ol;
6-[(4S)-7-chloro-1,4-dimethyl-8-(trifluoromethyl)-4H-imidazo[1,2-a][1,4]benzodiazepin-6-yl]-5-fluoro-pyridin-2-ol;
6-[(10S)-6-chloro-10-methyl-5-(trifluoromethyl)-1,9,12-triazatetracyclo[9.6.0.02,7.013,17]heptadeca-2,4,6,8,11,13(17)-hexaen-8-yl]-5-fluoro-pyridin-2-ol; 6-[(4S)-7-chloro-2,4-dimethyl-8-(trifluoromethyl)-4H-[1,2,4]triazolo[1,5-a][1,4]benzodiazepin-6-yl]-5-fluoropyridin-2-ol;
5-chloro-6-[(4S)-7-chloro-1,4-dimethyl-8-(trifluoromethyl)-4H-imidazo[1,2-a][1,4]benzodiazepin-6-yl]pyridin-2-ol;
5-chloro-6-[(4S)-7-chloro-2,4-dimethyl-8-(trifluoromethyl)-4H-imidazo[1,2-a][1,4]benzodiazepin-6-yl]pyridin-2-ol;
6-[(4S)-7-chloro-2,4-dimethyl-8-(trifluoromethyl)-4H-imidazo[1,2-a][1,4]benzodiazepin-6-yl]-5-fluoro-pyridin-2-ol;
5-chloro-6-[(4S)-7-chloro-2,4-dimethyl-8-(trifluoromethyl)-4H-[1,2,4]triazolo[1,5-a][1,4]benzodiazepin-6-yl]pyridin-2-ol; azetidin-1-yl-[(4S)-7-chloro-6-(3-fluoro-6-hydroxypyridin-2-yl)-4-methyl-8-(trifluoromethyl)-4H-imidazo[1,2-a][1,4]benzodiazepin-2-yl]methanone;
(4S)-7-chloro-N-cyclopropyl-6-(3-fluoro-6-hydroxy-2-pyridyl)-4-methyl-8-(trifluoromethyl)-4H-imidazo[1,2-a][1,4]benzodiazepine-2-carboxamide; and
(4S)-7-chloro-6-(3-fluoro-6-hydroxy-2-pyridyl)-N-isopropyl-4-methyl-8-(trifluoromethyl)-4H-imidazo[1,2-a][1,4]benzodiazepine-2-carboxamide.

2. The compound according to claim 1, or a pharmaceutically acceptable salt thereof, wherein said compound is selected from:
- 6,7-dichloro-5-(2-fluoro-5-hydroxyphenyl)-1-methyl-1,3-dihydro-2H-benzo[e][1,4]diazepin-2-one;
- 6-chloro-5-(2-fluoro-5-hydroxyphenyl)-1,7-dimethyl-1,3-dihydro-2H-benzo[e][1,4]diazepin-2-one;
- 6-chloro-5-(2-fluoro-5-hydroxy-phenyl)-1-methyl-7-(trifluoromethyl)-3H-1,4-benzodiazepin-2-one;
- [7-chloro-6-(2-fluoro-5-hydroxy-phenyl)-8-(trifluoromethyl)-4H-[1,2,4]triazolo[1,5-a][1,4]benzodiazepin-2-yl]-(3-methoxyazetidin-1-yl)methanone;
- 6-[(4S)-7-chloro-1,4-dimethyl-8-(trifluoromethyl)-4H-imidazo[1,2-a][1,4]benzodiazepin-6-yl]-5-fluoro-pyridin-2-ol; and
- 5-chloro-6-[(4S)-7-chloro-1,4-dimethyl-8-(trifluoromethyl)-4H-imidazo[1,2-a][1,4]benzodiazepin-6-yl]pyridin-2-ol.

3. A pharmaceutical composition comprising the compound according to 1, or a pharmaceutically acceptable salt thereof, and a therapeutically inert carrier.

4. A method for treating or preventing autism spectrum disorder (ASD), said method comprising administering an effective amount of the compound according to claim 1, or a pharmaceutically acceptable salt thereof.

5. A compound 6-chloro-5-(2-fluoro-5-hydroxyphenyl)-1,7-dimethyl-1,3-dihydro-2H-benzo[e][1,4]diazepin-2-one, or a pharmaceutically acceptable salt thereof.

6. A compound (4S)-7-chloro-6-(3-fluoro-6-hydroxy-2-pyridyl)-N-isopropyl-4-methyl-8-(trifluoromethyl)-4H-imidazo[1,2-a][1,4]benzodiazepine-2-carboxamide, or a pharmaceutically acceptable salt thereof.

7. A compound 6-[(4S)-7-chloro-1,4-dimethyl-8-(trifluoromethyl)-4H-imidazo[1,2-a][1,4]benzodiazepin-6-yl]-5-fluoro-pyridin-2-ol, or a pharmaceutically acceptable salt thereof.

8. A compound 5-chloro-6-[(4S)-7-chloro-1,4-dimethyl-8-(trifluoromethyl)-4H-imidazo[1,2-a][1,4]benzodiazepin-6-yl]pyridin-2-ol, or a pharmaceutically acceptable salt thereof.

* * * * *